US012589087B2

(12) United States Patent
Montine et al.

(10) Patent No.: US 12,589,087 B2
(45) Date of Patent: Mar. 31, 2026

(54) ENANTIOMER SELECTIVE ACTION ON NEUROTRANSMISSION

(71) Applicant: The Board of Trustees of the Leland Stanford Junior University, Stanford, CA (US)

(72) Inventors: Thomas J. Montine, Palo Alto, CA (US); Adam Wawro, Jozefoslaw (PL)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 392 days.

(21) Appl. No.: 18/284,226

(22) PCT Filed: Apr. 1, 2022

(86) PCT No.: PCT/US2022/023063
§ 371 (c)(1),
(2) Date: Sep. 26, 2023

(87) PCT Pub. No.: WO2022/216543
PCT Pub. Date: Oct. 13, 2022

(65) Prior Publication Data
US 2024/0115539 A1 Apr. 11, 2024

Related U.S. Application Data

(60) Provisional application No. 63/170,773, filed on Apr. 5, 2021.

(51) Int. Cl.
| | |
|---|---|
| *A61K 31/223* | (2006.01) |
| *A61K 31/197* | (2006.01) |
| *A61P 25/16* | (2006.01) |
| *A61P 25/28* | (2006.01) |

(52) U.S. Cl.
CPC .......... *A61K 31/223* (2013.01); *A61K 31/197* (2013.01); *A61P 25/16* (2018.01); *A61P 25/28* (2018.01)

(58) Field of Classification Search
CPC .................................................... A61K 31/223
See application file for complete search history.

(56) References Cited

U.S. PATENT DOCUMENTS

2011/0190276 A1 8/2011 Alvaro et al.

OTHER PUBLICATIONS

Mcbean (1994) "Inhibition of the glutamate transporter and glial enzymes in rat striatum by the gliotoxin, alpha aminoadipate" *British journal of pharmacology*, 113(2), pp. 536-540.
Selmer et al. (2000) "The Biosynthesis of methylated Amino Acids in the active site region of methyl-coenzyme M reductase." *Journal of Biological Chemistry*. 275(6), pp. 3775-3760.
Frye. (2014) "Clinical potential, safety, and tolerability of arbaclofen in the treatment of autism spectrum disorder" Drug, Healthcare and Patient Safety, 6; 69-76.
Selmer. (2000) "The Biosynthesis of Methylated Amino Acids in the Active Site Region of Methyl-coenzyme M Reductase" vol. 275, No. 6, pp. 3755-3760.
Wawro (2021) "Enantiomers of 2-methylglu.tamate and 2-methylglutamine selectively impact mouse brain .metabolism and behavior" Nature Portfolio; 11:8138 abstract; p. 5, paragraph 1-2; p. 9, paragraph 1-2; DOI: 10.1038/s41598-021-87569-1.

*Primary Examiner* — Golam M Shameem
(74) *Attorney, Agent, or Firm* — Pamela J. Sherwood; Bozicevic, Field & Francis LLP

(57) ABSTRACT

Methods of use, pharmaceutical formulations, and labeled versions of compounds are provided of compounds that penetrate the blood-brain barrier and influence the balance of excitatory versus inhibitory neurotransmission by enantiomer selective modulation of glutamate and GABA metabolism. In some embodiments, a glutamatergic false neurotransmitter is S-2-methylglutamate (S-2MeGlu). In some embodiments a GABAergic false neurotransmitters is R-4 aminopentanomic acid (4APA) or S-4 aminopentanomic acid (S-4APA), with high penetration of the blood brain barrier and low toxicity, therein providing useful pharmacologic or imaging agents.

15 Claims, 26 Drawing Sheets

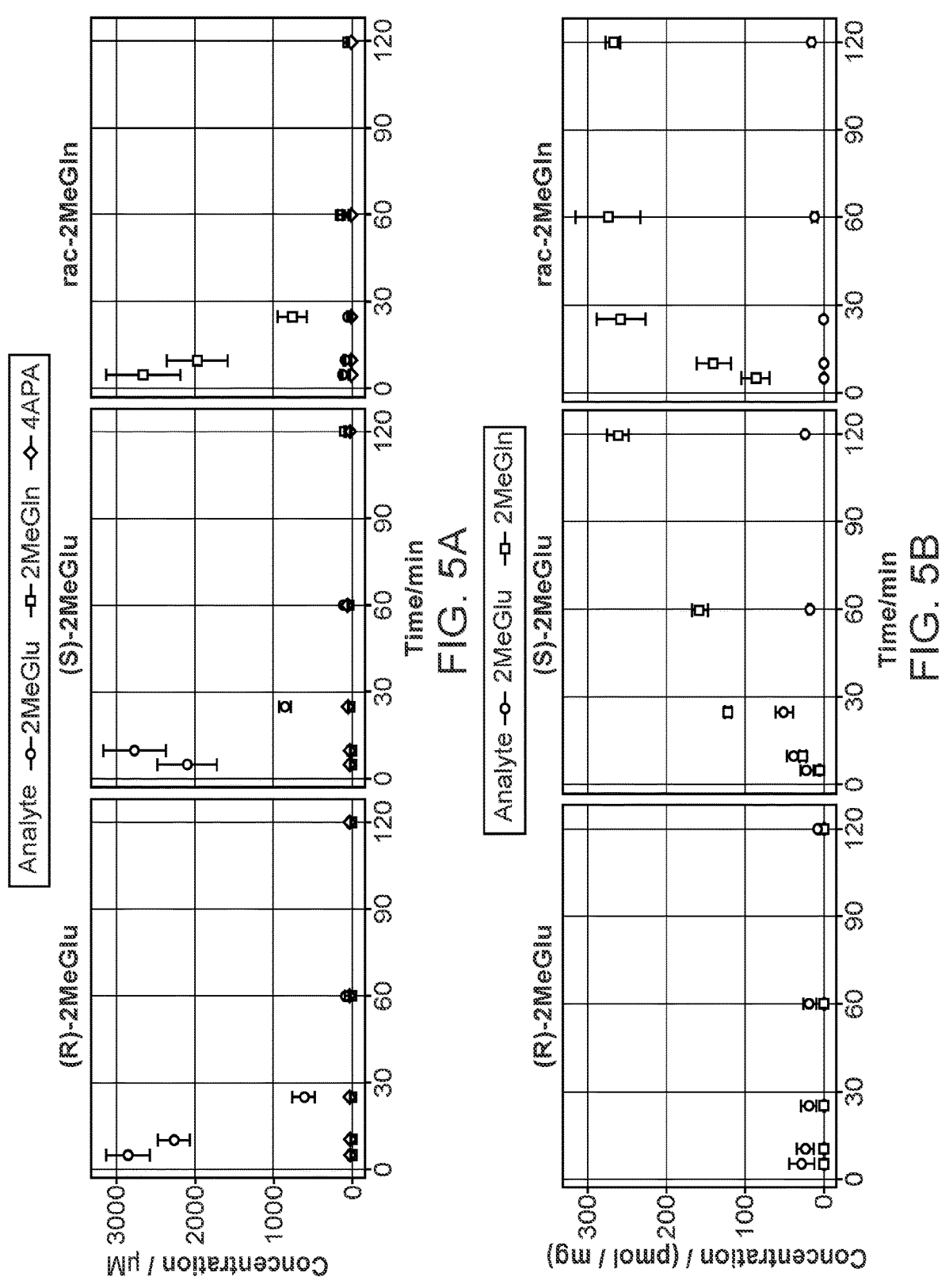

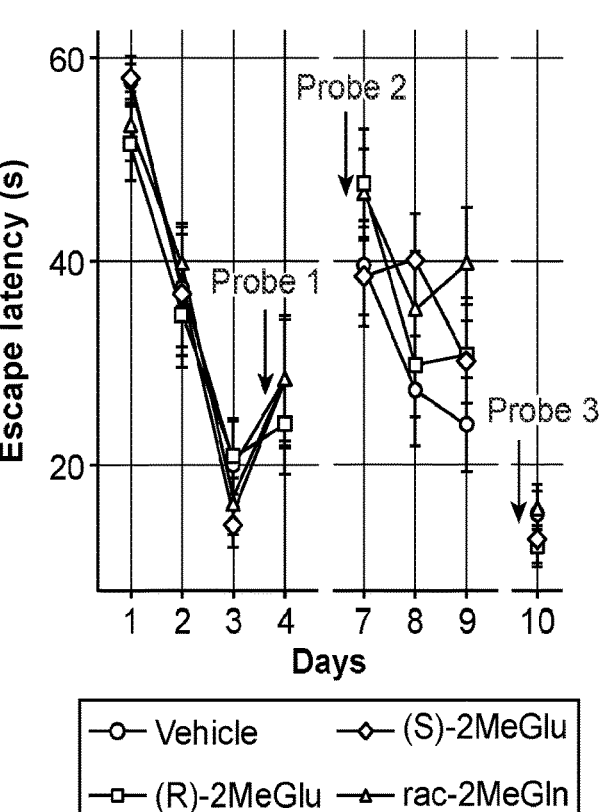
FIG. 14A
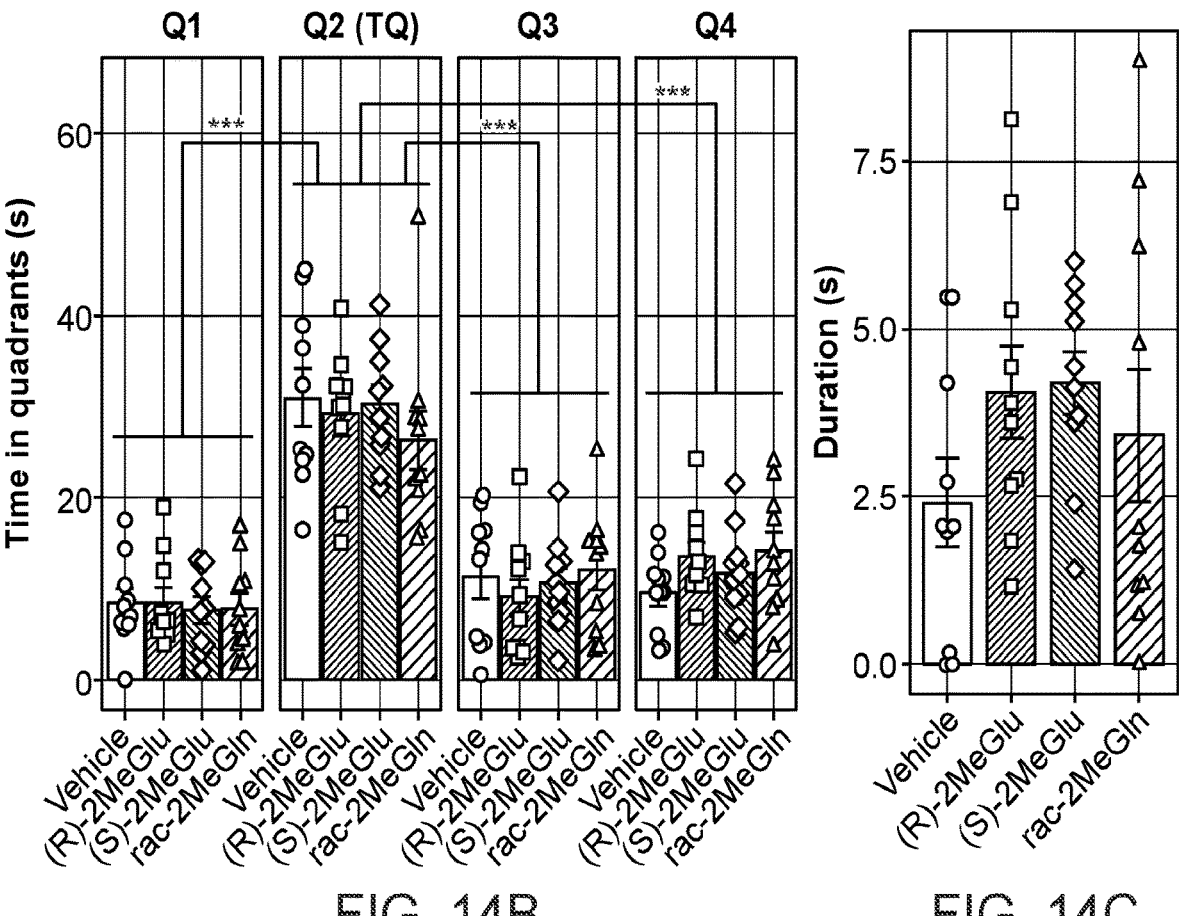
FIG. 14B                    FIG. 14C

Figures 20A, 20B:
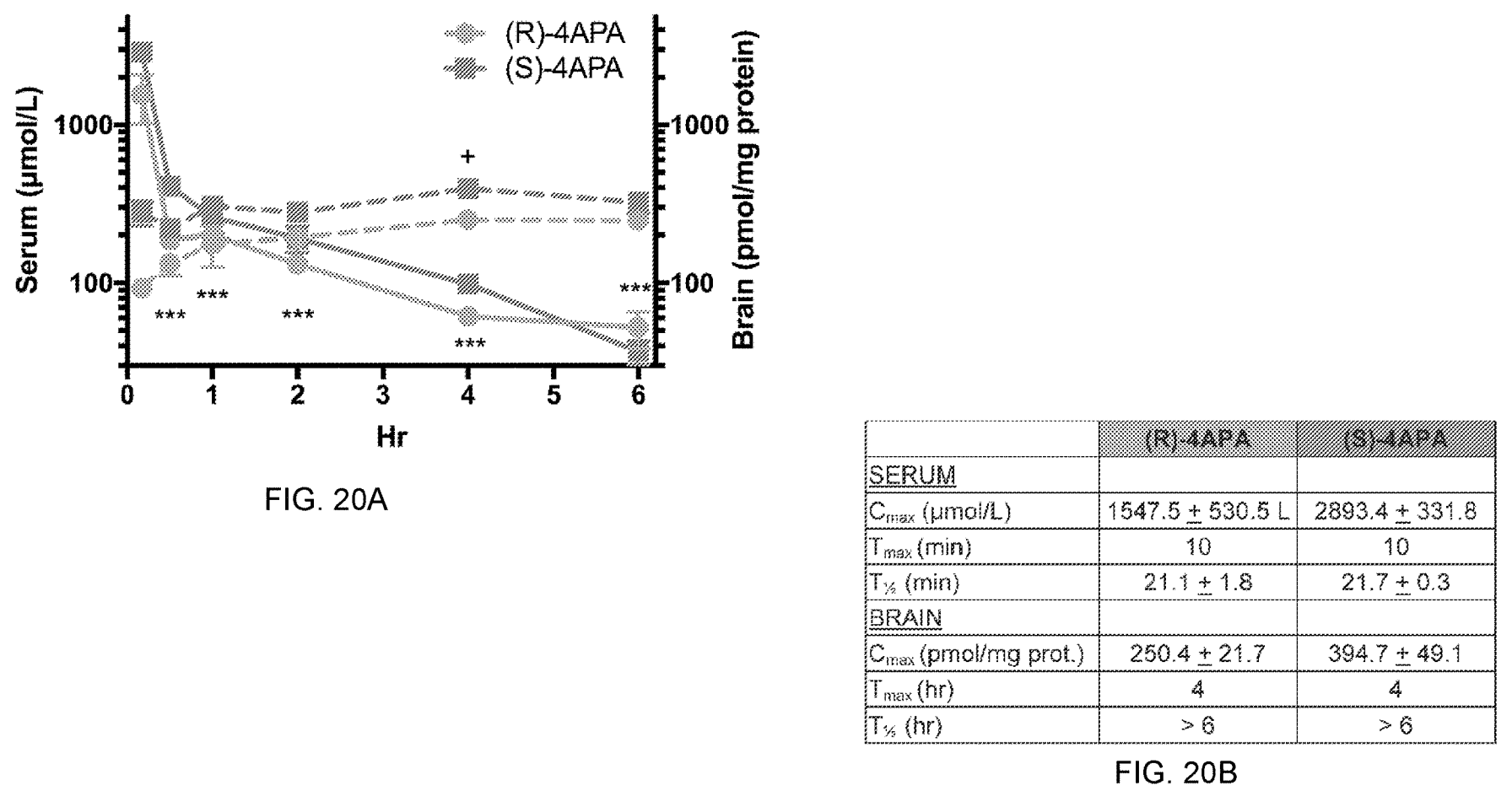

| SERUM | (R)-4APA | (S)-4APA |
|---|---|---|
| $C_{max}$ (μmol/L) | 1547.5 ± 530.5 L | 2893.4 ± 331.8 |
| $T_{max}$ (min) | 10 | 10 |
| $T_{½}$ (min) | 21.1 ± 1.8 | 21.7 ± 0.3 |
| BRAIN | | |
| $C_{max}$ (pmol/mg prot.) | 250.4 ± 21.7 | 394.7 ± 49.1 |
| $T_{max}$ (hr) | 4 | 4 |
| $T_{½}$ (hr) | > 6 | > 6 |

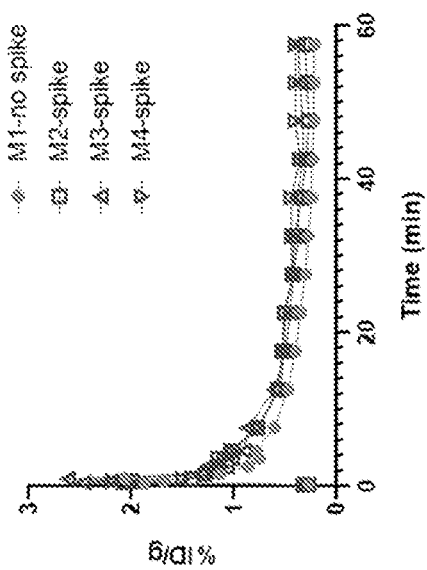
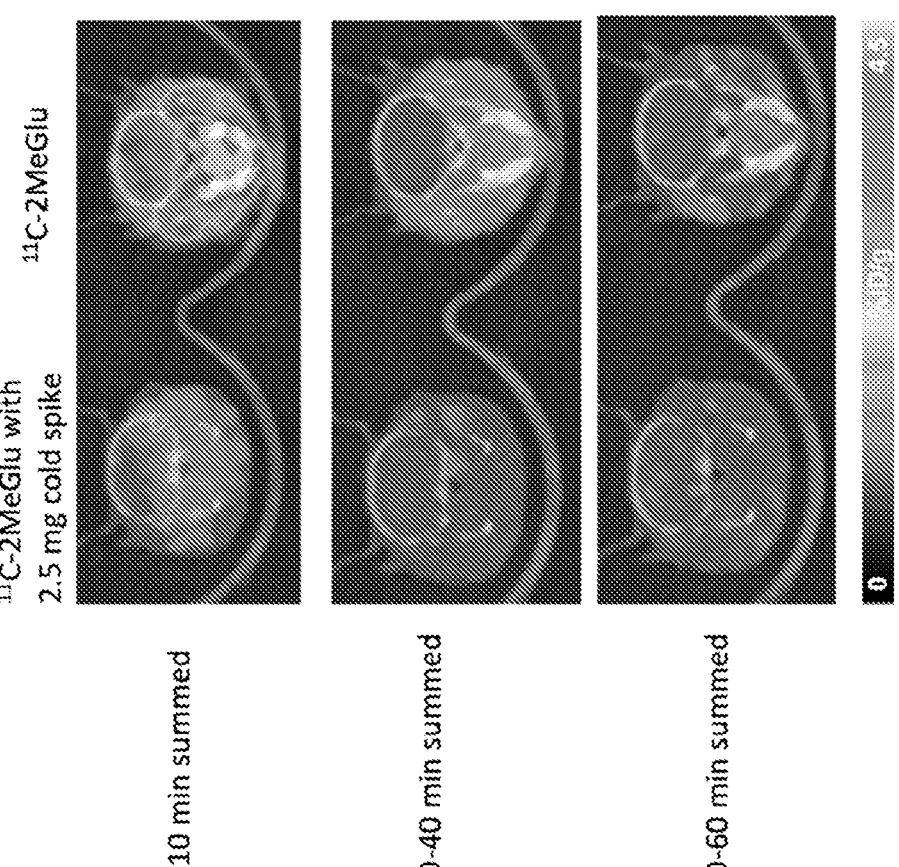
FIG. 26

ENANTIOMER SELECTIVE ACTION ON NEUROTRANSMISSION

CROSS REFERENCE TO RELATED APPLICATION

The present application claims the benefit of and priority to U.S. Provisional Patent Application No. 63/170,773 filed Apr. 5, 2021, the entire disclosure of which is hereby incorporated by reference in its entirety.

BACKGROUND

The amino acid L-glutamine and the neurotransmitters L-glutamate and γ-aminobutyric acid (GABA) are linked metabolically via the glutamate-glutamine cycle and the GABA shunt. Imbalance of the complex metabolic interplay between excitatory (mostly glutamatergic) and inhibitory (mostly GABAergic) neurotransmission has been implicated in a wide range of psychiatric and neurologic disorders. Inherited deficiencies in the glutamate-glutamine cycle, either glutamine synthetase (GS) deficiency or glutaminase deficiency, yield neonatal-infantile epileptic encephalopathy and early death. Inherited deficiencies within the GABA shunt include SSADH deficiency and GABA-transaminase deficiency that are characterized by language and motor delay, cognitive impairment, ataxia, autistic behaviors, hallucinations, and epilepsy in both children and adults, with elevated γ-hydroxybutyrate (GHB) and/or GABA. Prevalent diseases are proposed to derive at least in part from an imbalance of excitatory and inhibitory neurotransmission, including mood disorders, some forms of psychosis, epilepsy, Alzheimer's disease, and Parkinson's disease. The prospect of restoring balance to these opposing systems has been the focus of many candidate therapeutics, some of which have gone on to wide-spread clinical application: receptor specific agonists, antagonists, and allosteric modulators, transporter inhibitors, gene transfer, and most recently cell therapy.

Existing approaches fail to target the metabolic balance of the GABA shunt or the glutamate-glutamine cycle, and as yet none has had a major impact on alleviating the common psychiatric or neurodegenerative diseases listed above.

SUMMARY

Imbalance of glutamate (excitatory) versus GABAergic (inhibitory) neurotransmission contributes to a range of neurodevelopmental, psychiatric/behavioral, and neurodegenerative diseases. Methods of use, pharmaceutical formulations, and labeled versions of compounds are provided, relating to compounds that penetrate the blood-brain barrier and influence the balance of excitatory versus inhibitory neurotransmission by enantiomer selective modulation of glutamate and GABA metabolism.

In some embodiments, compounds for use in the methods of the disclosure are isolated enantiomers of 2-methylglutamate (2MeGlu) or 2-methylglutamine (2MeGln), which are demonstrated to be enantiomeric selective metabolism modulators in the GABA shunt or glutamate-glutamine cycle, with high penetration of the blood brain barrier and low toxicity, therein providing useful pharmacologic or imaging agents. In some embodiments the compound of interest is (S)-2MeGlu, which is shown herein to be a glutamatergic false neurotransmitter, or (S)-2MeGln, which is shown herein to be a metabolic precursor of (S)-2MeGlu.

In other embodiments, compounds for use in the methods of the disclosure are enantiomers of 4-aminopentanoic acid (4APA). Enantiomers of 4APA selectively replace GABA in synaptosomes, but have little or no activity on a broad panel GABA and glutamate receptors. In some embodiments the compound of interest is (S)-4APA or (R)-4APA, which are shown herein to be GABAergic false neurotransmitters.

In some embodiments, a composition is provided, comprising an effective dose of a compound: (S)-2MeGlu, (S)-2MeGln, (S)-4APA, (R)-4APA and a pharmaceutically acceptable excipient. In some embodiments, the compounds in the formulation are enantiomerically pure, e.g. at least about 80%, at least about 90%, at least about 95%, at least about 99% of the selected enantiomer. In other embodiments, a racemic composition is used, e.g. racemic 2MeGln, racemic 4APA. In some embodiments the composition is configured for delivery as a pharmacologic agent. The dose may be effective for treatment of diseases that derive in part from imbalance of excitatory vs. inhibitory neurotransmission, including epilepsy, autism, mood disorders, psychosis, Alzheimer's disease, and Parkinson's disease. In some embodiments the disease is Parkinsons disease, where the dose may be effective to improve movement in the patient. In some embodiments the disease is Alzheimers disease, where the dose may be effective to improve cognitive function.

In some embodiments a method is provided for altering the excitatory/inhibitory balance of neurons, the method comprising administering an effective dose of one or more of: (S)-2MeGlu, (S)-2MeGln, (S)-4APA, (R)-4APA, racemic 2MeGln, racemic 4APA. In some embodiments (S)-2MeGlu is administered. Administration of (S)-2MeGlu decreases excitatory neural activity by acting as a false neurotransmitter and competing for glutamate in the neurotransmitter pool without having significant activity on glutamate and GABA receptors. Administration of (S)-2MeGln decreases excitatory neural activity by acting as a metabolic precursor of (S)-2MeGlu. Administration of 4APA enantiomers decreases inhibitory neural activity by acting as a false neurotransmitter and competing for GABA in the neurotransmitter pool without having significant activity on glutamate and GABA receptors.

Acute, high doses of these compounds is shown to have minimal mortality. (R)-2MeGlu or (S)-2MeGlu cause temporary, marked reduction in response to novelty/locomotor activity while remaining alert and responsive to ambient noise and touch. The usefulness of such impaired response to novelty/locomotor activity has utility in the management of patients undergoing procedures or imaging sessions, and in the treatment of neurological and psychiatric disorders that derive in part from imbalance of excitatory and inhibitory neurotransmission. S-2MeGlu dose-dependently rescues motor function in two different animal models of PD and cognitive improvement in an animal model of AD. R-4APA rescues motor function in a transgenic animal model of PD.

In some embodiments, an imaging composition is provided, comprising an effective dose of a compound: (S)-2MeGlu, (S)-2MeGln, (S)-4APA, or (R)-4APA, comprising an imaging label, e.g. $^{18}$F, $^{11}$C, $^{15}$O for positron emission tomography, and a pharmaceutically acceptable excipient. In some embodiments the composition is configured for delivery as an imaging agent.

In some embodiments, a method is provided for molecular imaging of glutamine producing and/or transporting cells, the method comprising administering (S)-2MeGlu or 2MeGln comprising an imaging label, e.g. $^{18}$F, $^{11}$C, $^{15}$O; and detecting the presence of the imaging label by PET or other means. A major application of PET ligands for glutamine transport is in detection of several forms of cancer. Enantiomer-specific access to brain and metabolism of (S)-2MeGlu and (S)-2MeGln makes them ideal candidates for labeling and for molecular imaging of glutamine producing and/or transporting cells.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

4 hydrolyzed counterpart 2MeGlu. Total intra- and extracellular amounts of 2MeGln (—CONH$_2$) and 2MeGlu (—COOH) were determined in cells and media. Primary neuron cell cultures were incubated in the presence of 1 mM 2MeGln for 2 h at 37° C. along with cell-free controls.

FIGS. 5A-5B. Pharmacokinetics of 2Me compounds and their metabolites measured in mouse serum (A) and brain (B) after IP injection of 100 mg/kg of test compounds (in columns). Concentrations are expressed per volume in the serum samples and per protein content in the brain samples. Data are shown as mean±SEM, n=3.

FIGS. 6A-6D. Exploratory and locomotor behavior in 2 month-old male C57Bl/6 mice was assessed by total distance moved in the novel cage test (A) or in the activity chamber (B-D). Mice were either injected and then immediately tested (acute groups in A-C), or injected daily for one week prior to testing (chronic groups in D). Data are shown as mean±SEM. (A) Dose-response for each of the three compounds vs. total distance moved from 0 to 60 minutes in the novel cage test expressed as % of vehicle exposed mice (n=3 mice per group). Two-way ANOVA had $F_{Interaction}$ (4, 18)=9.068, P=0.0003; $F_{Dose}$ (2, 18)=14.91, P=0.0002; and $F_{Compound}$ (2, 18)=21.89, P<0.0001. Tukey's multiple comparison test was significantly different for rac-2MeGln vs. (R)-2MeGlu (**P<0.0001) and vs. (S)-2MeGlu (*P=0.0002). (B) Time course of activity chamber distance moved following acute 100 mg/kg had two-way repeated measures ANOVA with $F_{Interaction}$ (87, 580)=1.879, P<0.0001; $F_{Time}$ (29, 580)=11.44, P<0.0001; and $F_{Exposure}$ (3, 20)=2.906, P=0.0600 (n=6 mice per group). Dunnett's multiple comparisons test had multiple early time points that were significantly different between vehicle and (R)-2MeGlu or between vehicle and (S)-2MeGlu (*P<0.05, P<0.01, *P<0.001, ****P<0.0001); vehicle was not significantly different from rac-2MeGln at any time point. (C) Time course of activity chamber distance moved following acute 30 mg/kg had two-way repeated measures ANOVA with $F_{Interaction}$ (87, 580)=0.9328, P=0.6493; $F_{Time}$ (29, 580)=20.13, P<0.0001; and $F_{Exposure}$ (3, 20)=1.805, P=0.1786 (n=6 mice per group). Dunnett's multiple comparisons test had one time point that was significantly different between vehicle and (R)-2MeGlu (*P<0.05) or between vehicle and rac-2MeGln (#P<0.05); vehicle was not significantly different from (S)-2MeGlu at any time point. (D) Time course of activity chamber distance moved following chronic 10 mg/kg per day for one week had two-way repeated measures ANOVA with $F_{Interaction}$ (87, 986)=1.22, P=0.0912; $F_{Time}$ (29, 986)=62.35, P<0.0001; and $F_{Exposure}$ (3, 34)=1.122, P=0.3536; (n=6 mice per group). One vehicle group mouse and one (S)-2MeGlu group mouse were outliers using the ROUT method; they were removed from analysis.

Figures 7A, 7B:
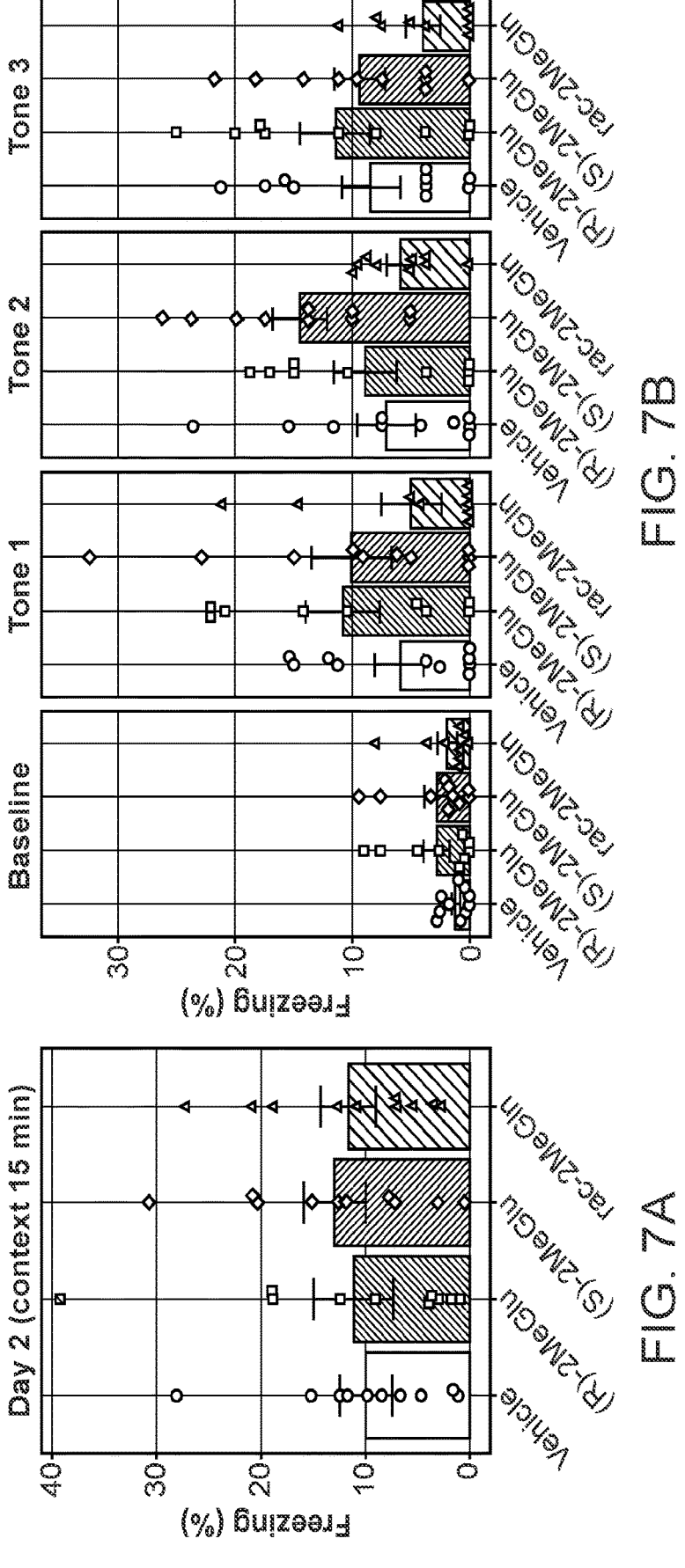

FIGS. 7A-7B. Behavioral effects of chronic 10 mg/kg/day IP dosing in 2 month-old male C57Bl/6 mice in fear conditioning tests on the fourth week of chronic exposure. (A) Freezing by the treatment group on Day 2 during contextual memory testing over 15 min. Data was not normally distributed. Kruskal-Wallis test had P approximately 0.7819. (B) Freezing at baseline and during each tone presentation on Day 3. Two-way repeated measures ANOVA had $F_{Interaction}$ (9, 102)=1.313, P=0.24; $F_{Tone}$ (3, 102)=13.95, P<0.0001; and $F_{Exposure}$ (3, 34)=2.015, P=0.13. All bars represent mean±SEM, n=10 mice per group.

Figures 8A, 8B, 8C:
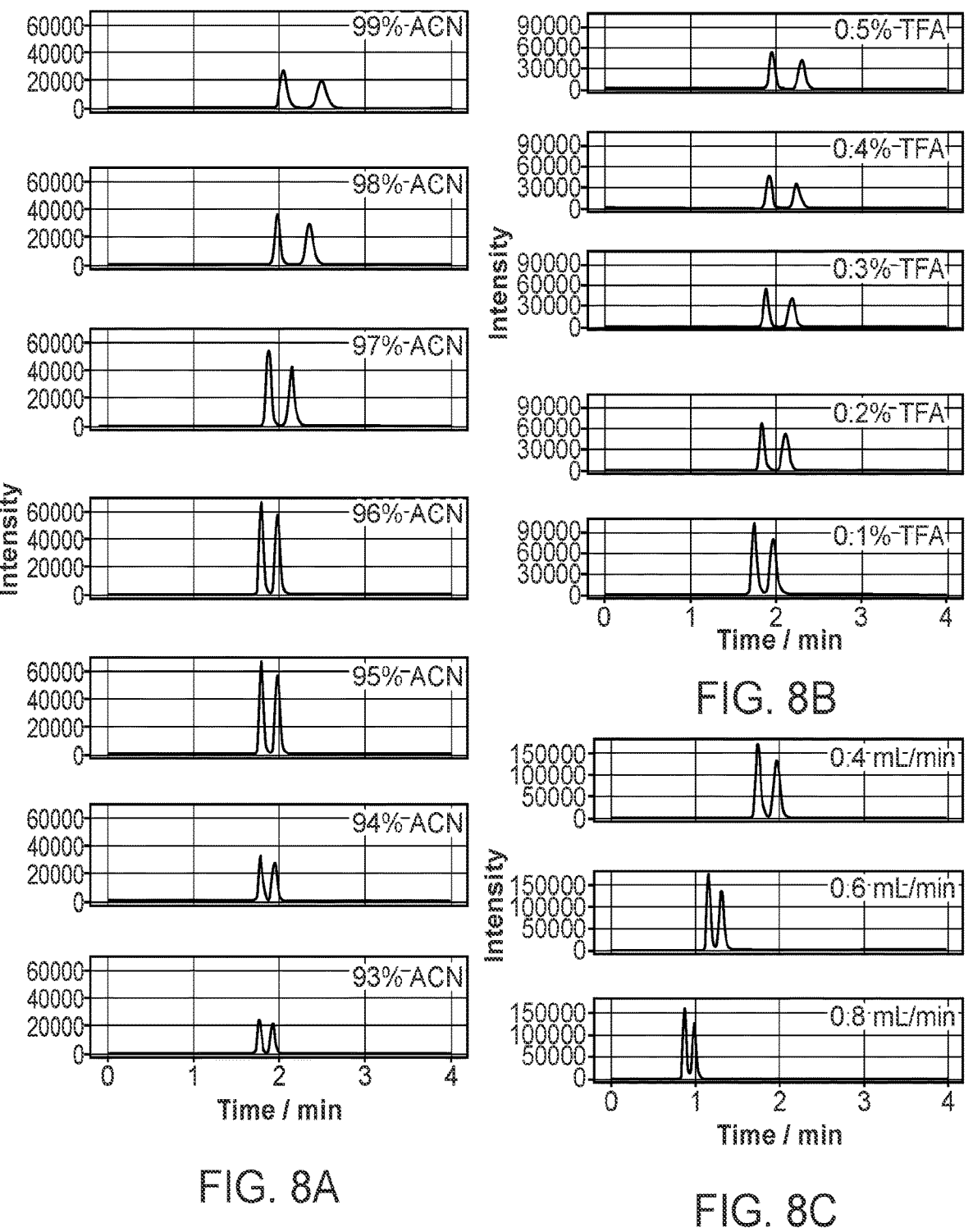

FIGS. 8A-8C. Optimization of 2MeGlu chiral separation. LC-MS/MS system was equipped with a chiral CROWN-PAK CR-I(+) column. Acetonitrile (A), trifluoroacetic acid (B) and mobile phase flow (C) were adjusted to achieve the optimum resolution in the minimum time and at the lowest acid concentration. Final conditions: 96% acetonitrile, 0.1% trifluoroacetic acid, flow 0.4 mL/min.

Figures 9A, 9B, 9C:
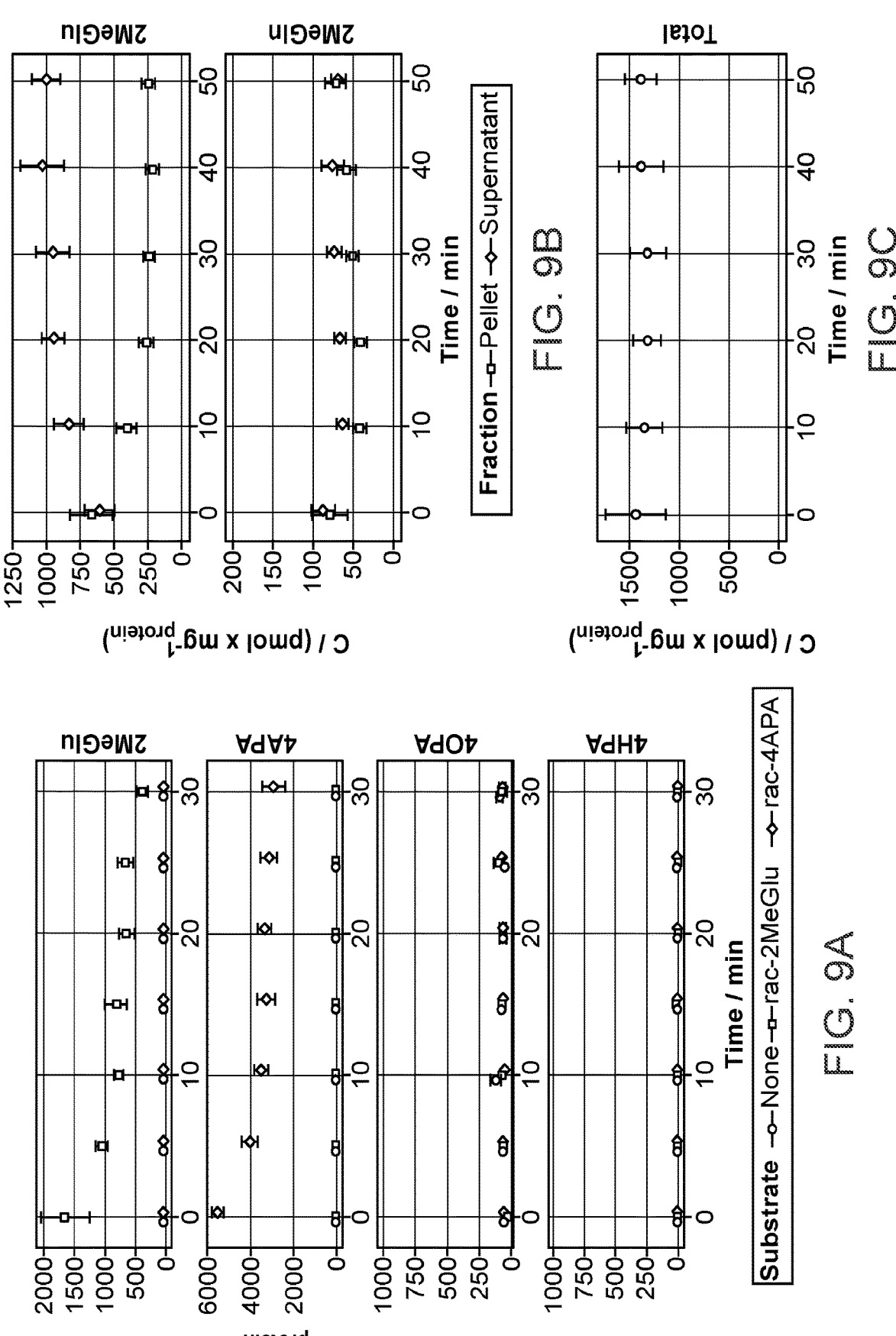

FIGS. 9A-9C. Synaptosomal metabolism of 2MeGlu and 4APA. (A) Synaptosomes were preincubated with 100 μM substrate for 15 min at 37° C. The pellet was washed, resuspended in normal KRP buffer and incubated at 37° C. as the levels of potential metabolites were monitored at 5 min intervals. 4OPA and 4HPA signals were below the limit of quantification. Data are mean±SEM, n=3. (B) Synaptosomal metabolism and retention of 2MeGlu. Synaptosomes preincubated with 100 μM 2MeGlu were resuspended in normal KRP buffer and intra- and extrasynaptosomal levels of 2MeGlu and 2MeGln were monitored. (C) Total concentration of intra- and extrasynaptrosomal 2MeGlu and 2MeGln in the monitored samples. Data are shown as mean±SEM, n=5.

Figures 10A, 10B:
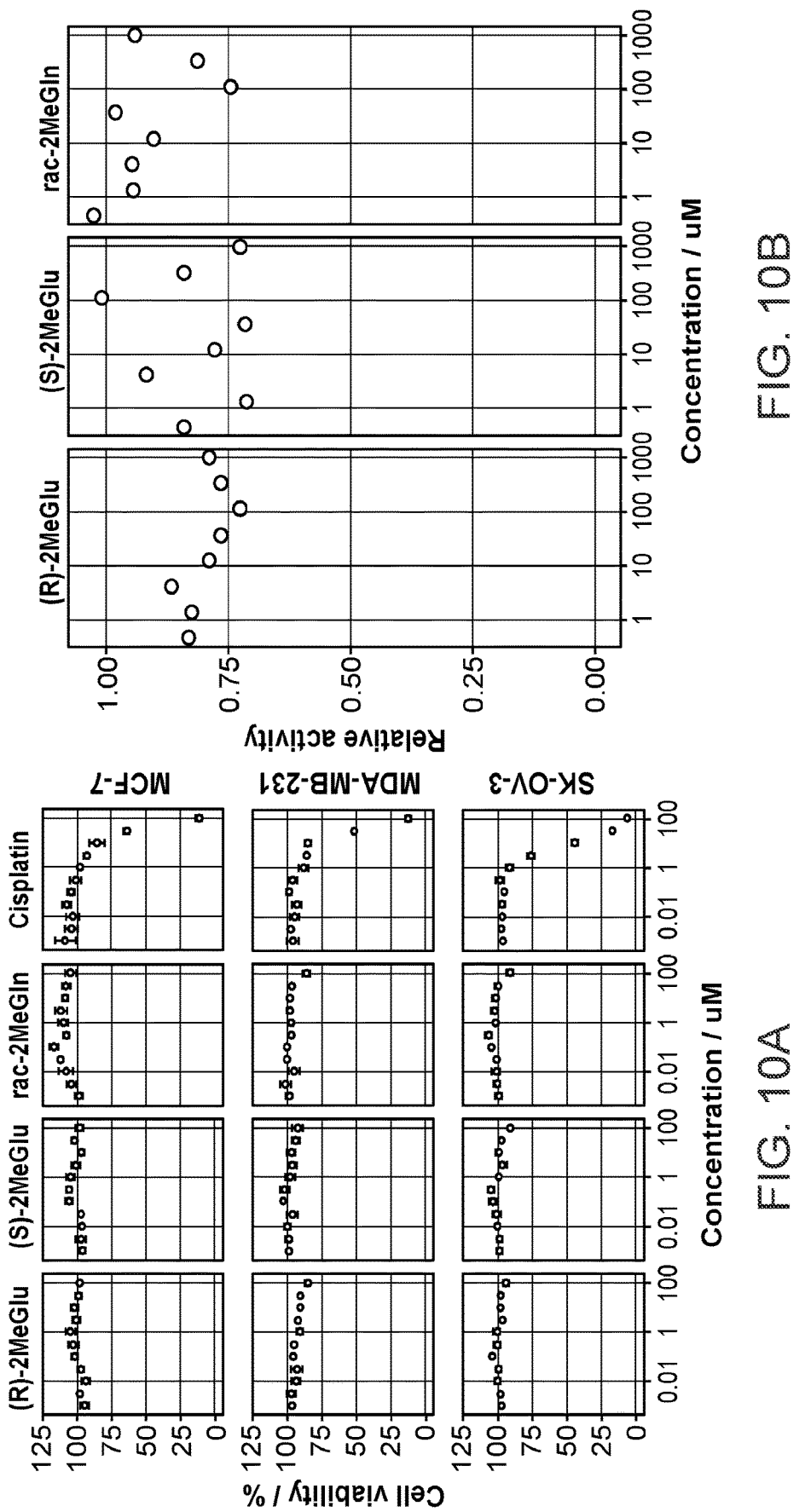

FIGS. 10A-10B. (A) Cell viability assay using 2MeGlu and 2MeGln on MCF-7, MDA-MB-231 and SK-OV-3 cancer cell lines. Compounds were tested at 1 nM-100 μM range in triplicate with cisplatin as a positive control. (B) GLS1 inhibitor assay using 2MeGlu and 2MeGln in the 0.5 μM-1 mM range. Data are shown as mean±SEM, n=3.

Figure 11:
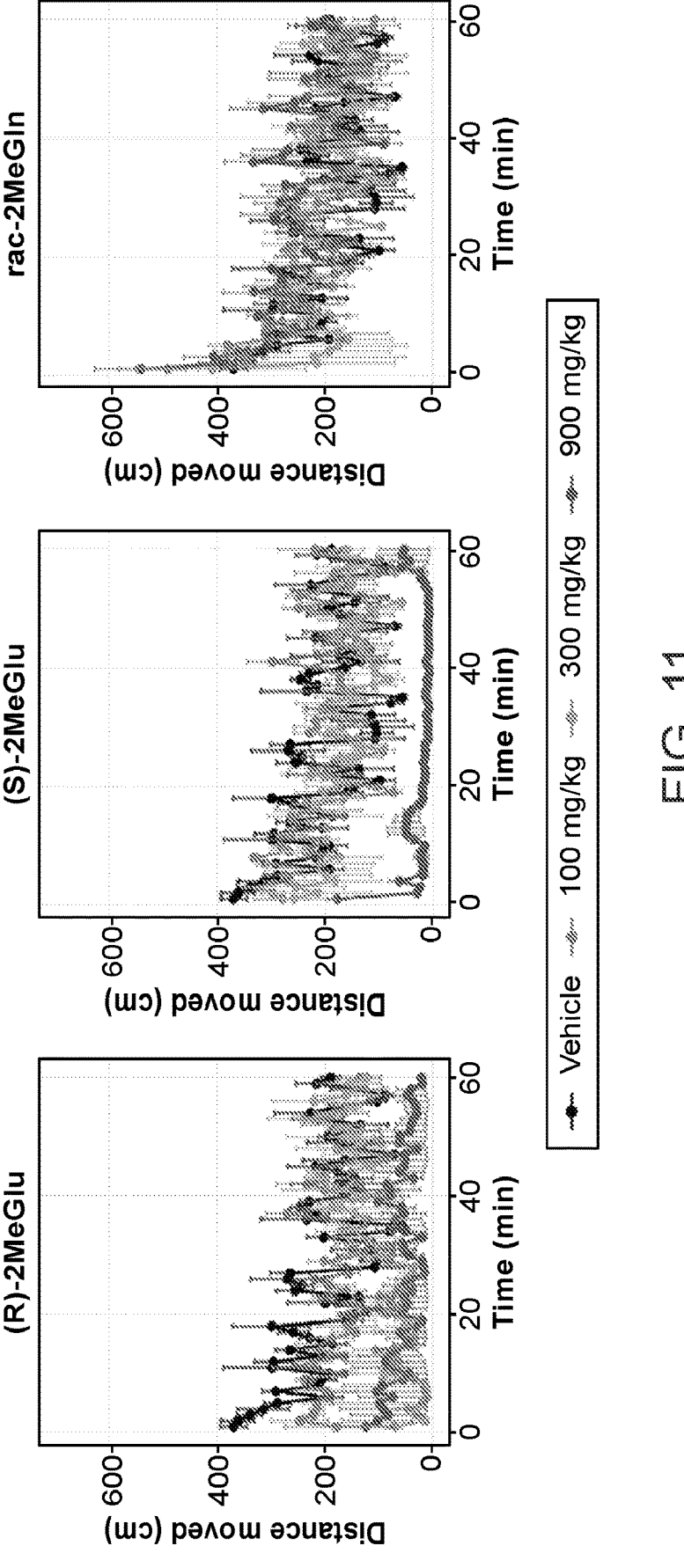

FIG. 11. Exploratory and locomotor behavior in 2 month-old male C57Bl/6 mice was assessed by total distance moved in the novel cage test. Data are shown as mean±SEM (n=3 mice per group) for distance (cm) moved each minute over 1 to 60 minutes following injection. These data were used to create the dose-response graph in FIG. 6A.

Figure 12B:
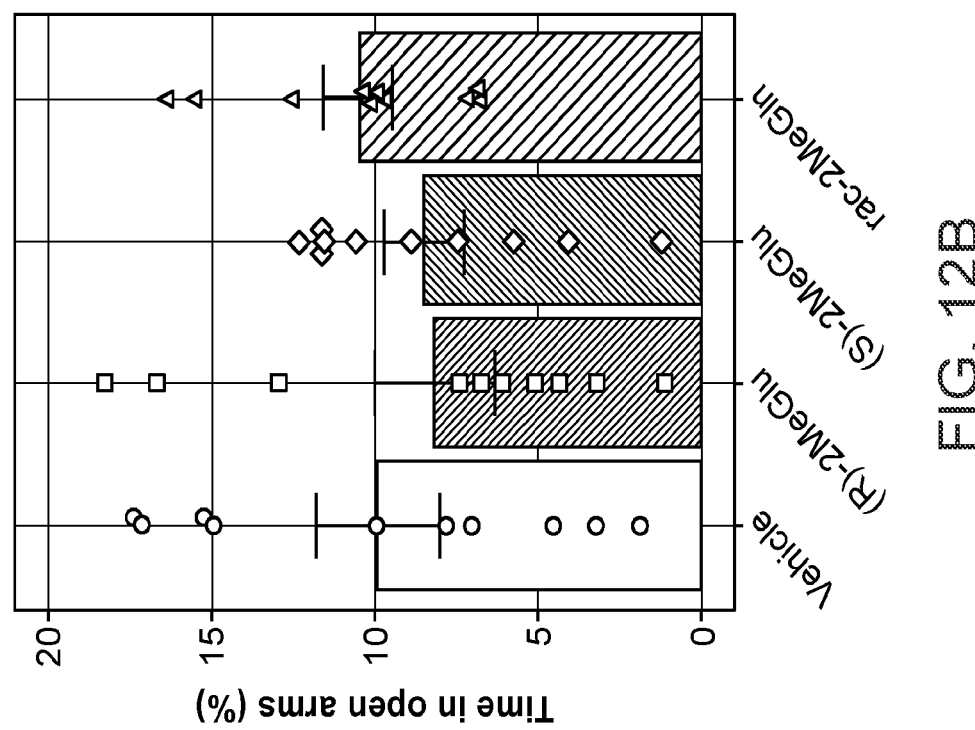
Figure 12A:
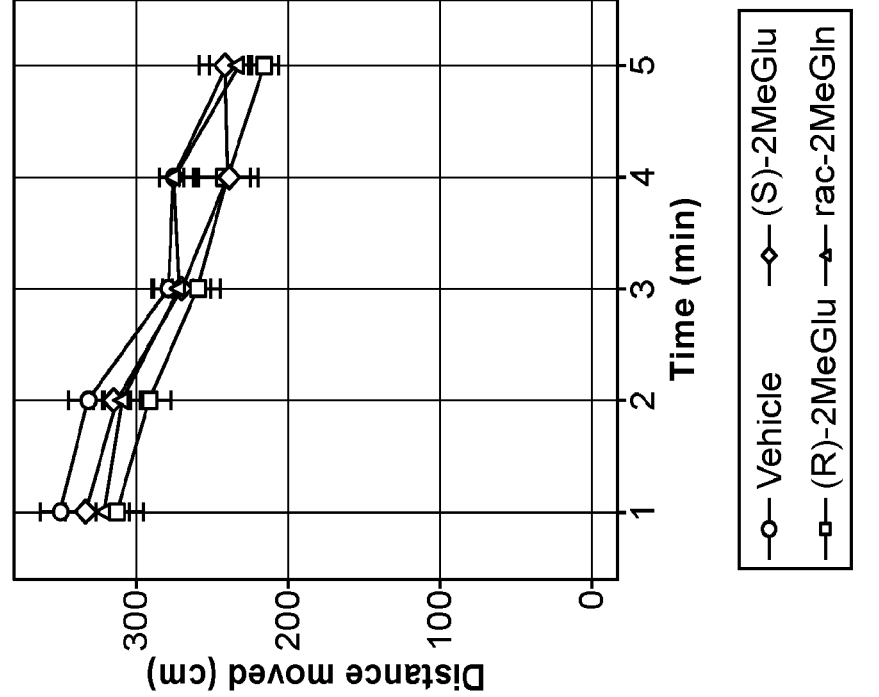

FIGS. 12A-12B. Behavioral effects of chronic 10 mg/kg/day IP dosing in 2 month-old male C57Bl/6 mice. Elevated Plus maze was performed after the first week of chronic exposure. Data are shown as mean±SEM, n=10 mice per group. (A) Two-way repeated measures ANOVA for distance moved (cm) had $F_{Interaction}$ (12, 144)=0.9112, P=0.5375; $F_{Time}$ (4, 144)=66.01, P<0.0001; and $F_{Treatment}$ (3, 36)=1.076, P=0.3713. (B) One-way ANOVA for percentage of time spent in the open arms of the maze vs. treatment measured over 5 minutes had $F_{Treatment}$=0.531, P=0.664.

Figure 13:
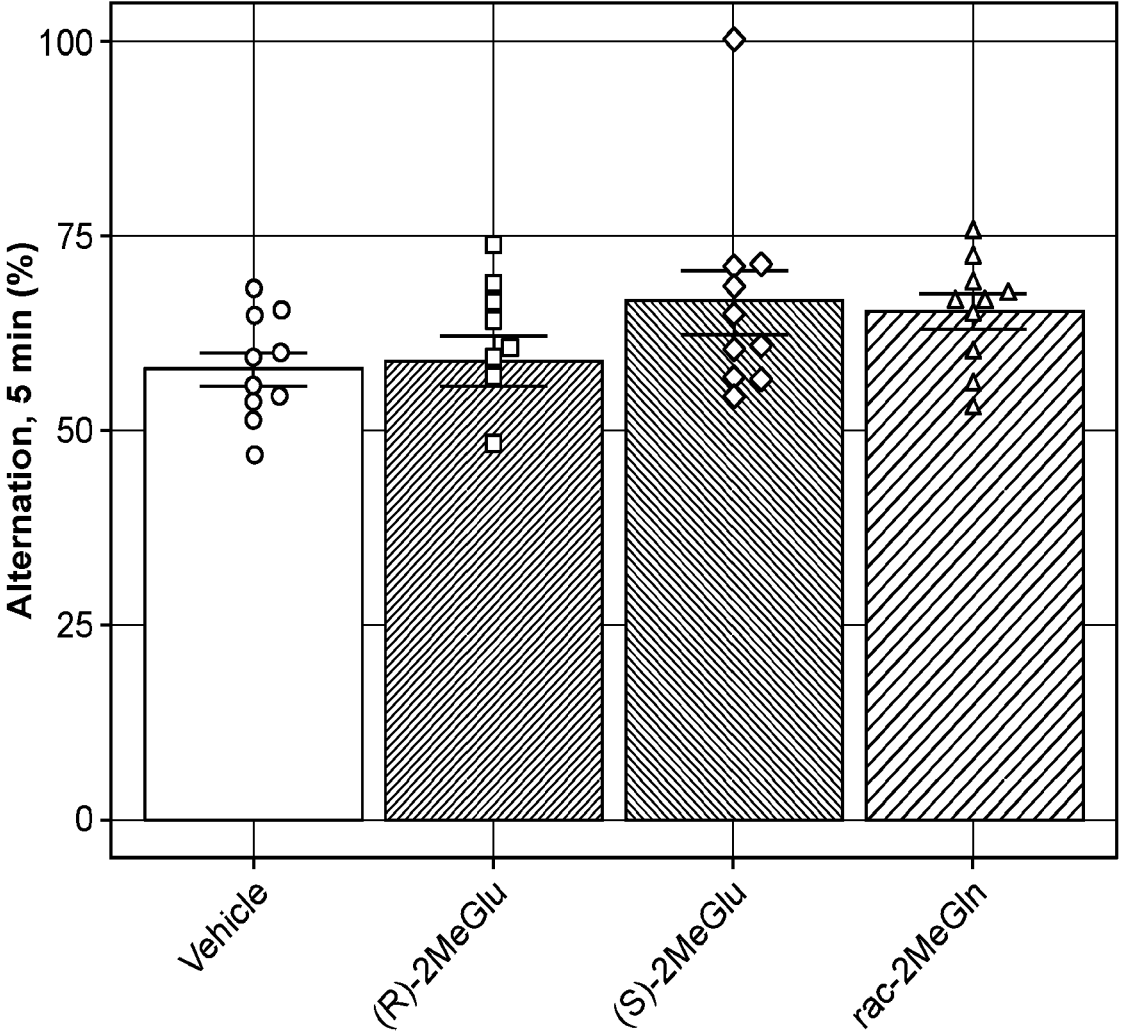

FIG. 13. Behavioral effects of chronic 10 mg/kg/day IP dosing in 2 month-old male C57Bl/6 mice. Y maze was performed during the second week of chronic exposure. Percent alternation over 5 minutes is shown as scatter plot as well as mean±SEM, n=10 mice per group. One-way ANOVA had F(3, 36)=2.018, P>0.05.

FIGS. 14A-14C. Behavioral effects of chronic 10 mg/kg/day IP dosing in 2 month-old male C57Bl/6 mice. Morris water maze was performed during the second and third weeks of chronic exposure. Data are shown as scatter plot as well as mean±SEM, n=10 mice per group. (A) Two-way repeated measures ANOVA for escape latency (seconds) had $F_{Interaction}$ (21, 252)=0.8483, P=0.6582; $F_{Time}$ (7, 252)= 37.39, P<0.0001; and $F_{Treatment}$ (3, 36)=0.4551, P=0.7153. (B) Two-way ANOVA for probe 1 time (seconds) in quadrants had $F_{Interaction}$ (3, 36)=0.844, P=0.577; $F_{Quadrants}$ (1, 36)=87.6, ***P<0.0001; and $F_{Treatment}$ (3, 36)=0.000, P=1.000. (C) One-way ANOVA of probe 1 duration in virtual platform (seconds) had P=0.3066.

Figures 15A, 15B:
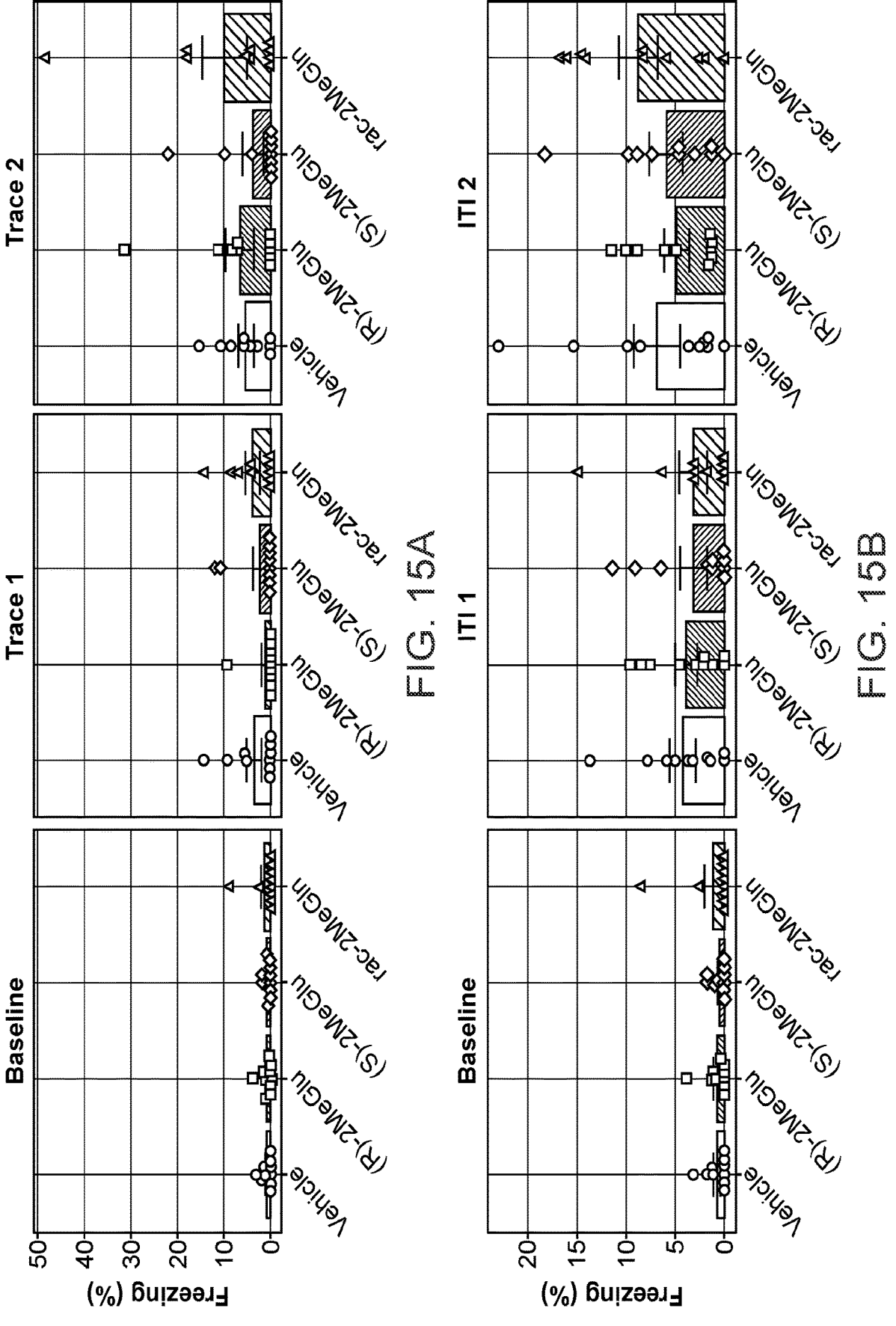

FIGS. 15A-15B. Behavioral effects of chronic 10 mg/kg/day IP dosing in 2 month-old male C57Bl/6 mice in fear conditioning tests on the fourth week of chronic exposure. Fear conditioning paradigm Day 1; training day, all treatment groups showed equivalent learning of the tone-shock association on Day 1. There was no difference between the experimental groups in (A) trace learning or (B) intertrial interval (ITI) freezing during the training day suggesting comparable learning of the task among all experimental groups. All bars represent mean±SEM, n=10 mice per group.

Figures 16A, 16B:
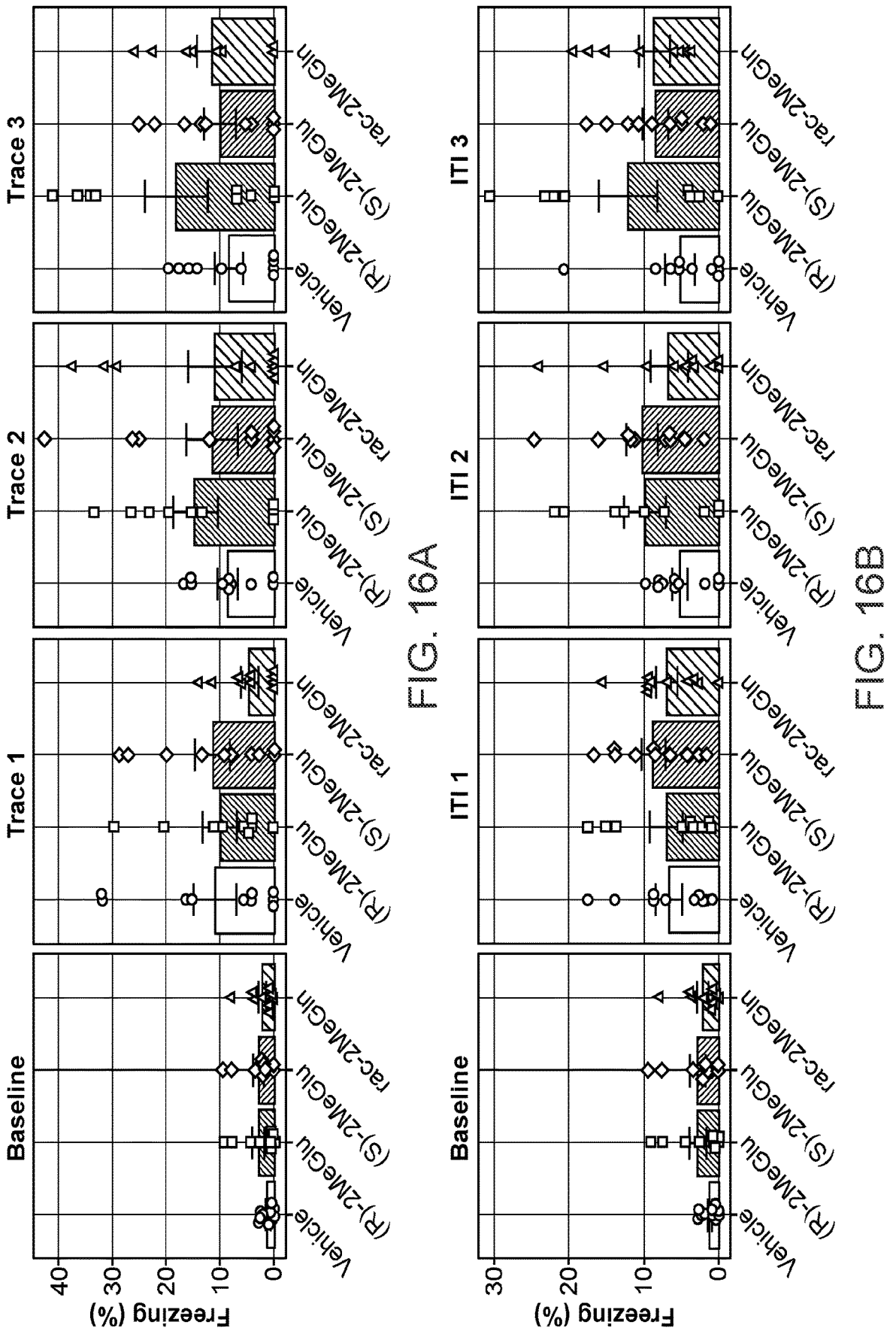

FIGS. 16A-16B. Behavioral effects of chronic 10 mg/kg/day IP dosing in 2 month-old male C57Bl/6 mice in fear conditioning tests on the fourth week of chronic exposure. Fear conditioning paradigm Day 3; Cued recall: there was no significant difference detected in freezing on Day 3 between experimental groups over the three tone presentations as shown in FIG. 7B. In addition, no significant difference was observed between the 18 seconds trace periods following 3 tone presentation on Day 3 (A). Finally, no significant difference in freezing was detected between experimental groups during the intertrial interval (ITI) on Day 3 following tone presentation, indicating comparable cued recall among experimental groups on day 3 (Figure B). All bars represent mean±SEM, n=10 mice per group.

Figure 17:
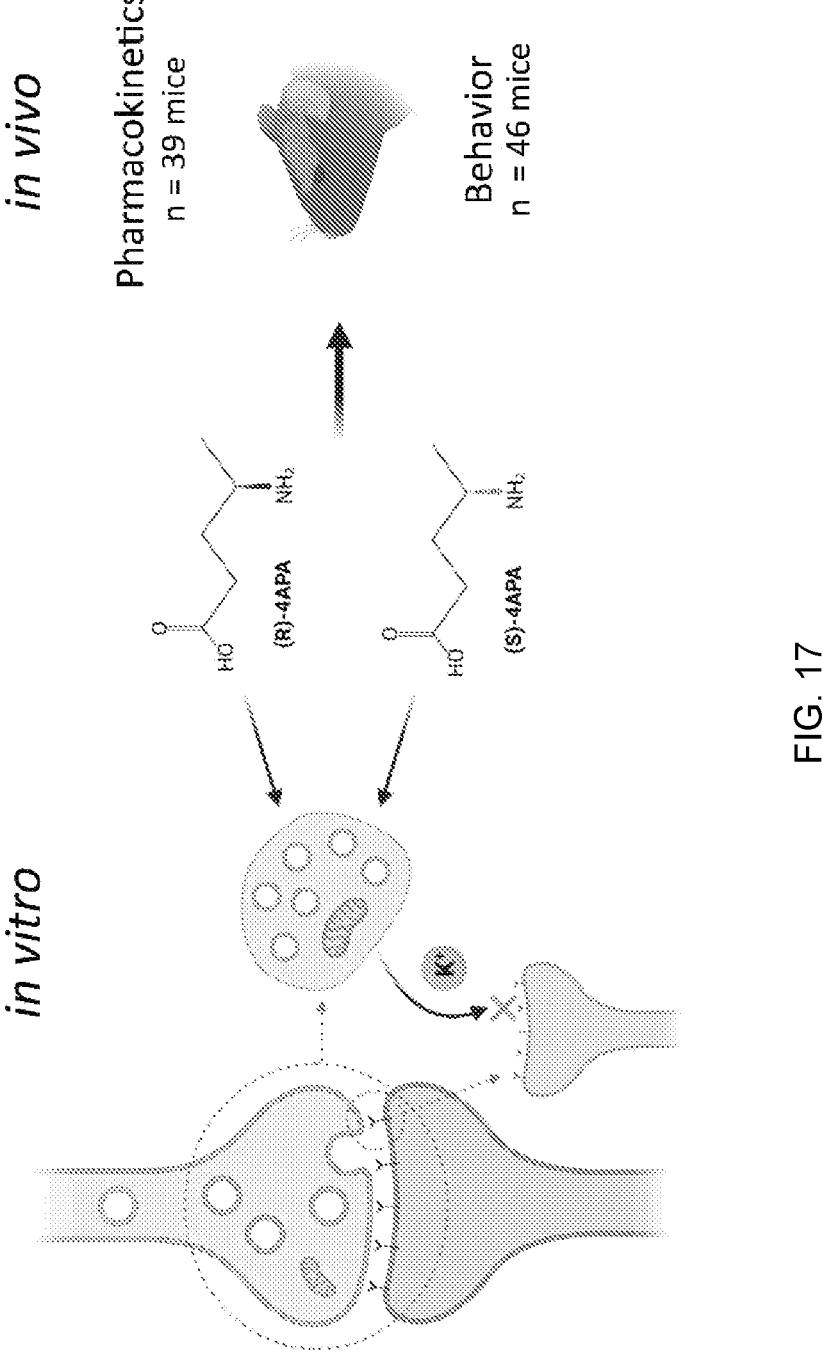

FIG. 17: Study design. Enantiomers of 4-aminopentanoic acid (4APA) were first assessed (left) for mouse cerebral synaptosome uptake, GABA displacement, and release following membrane depolarization with high concentration potassium cation. They were next injected into mouse brain (right), to assess pharmacokinetics and impact on mouse behavior.

Figure 18:
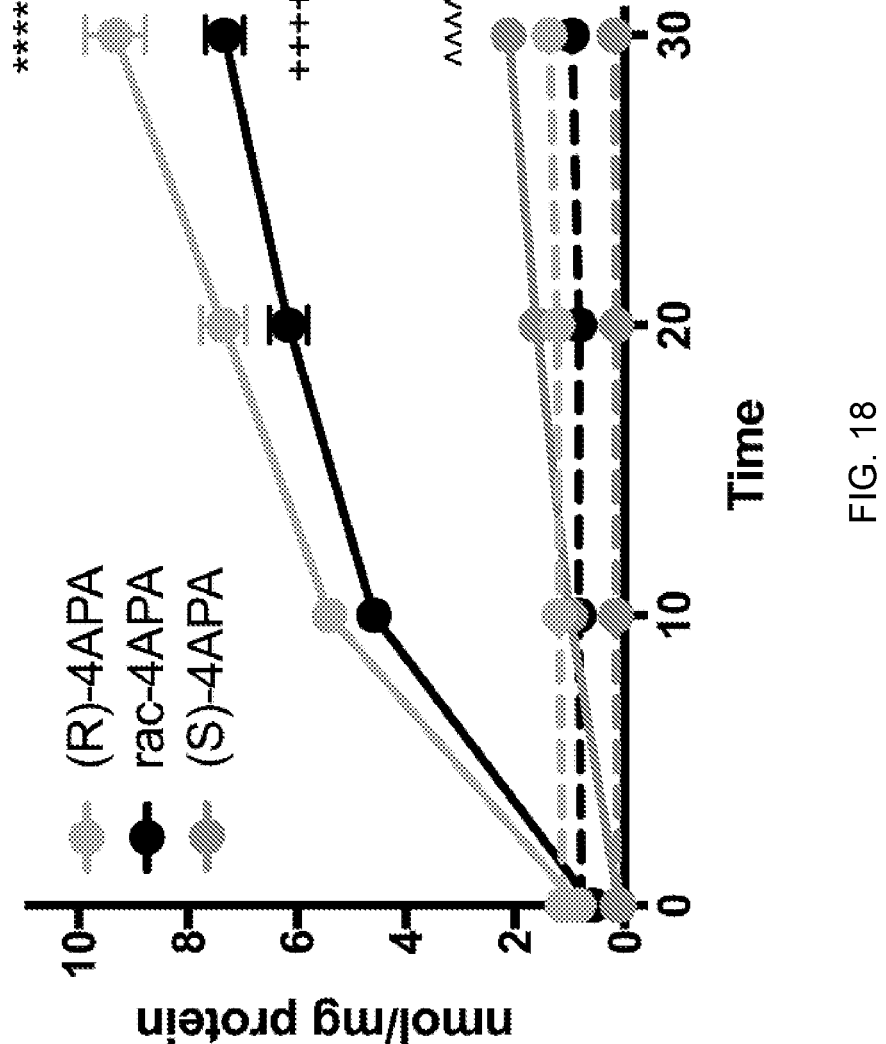

FIG. 18. Time- and temperature-dependent uptake of 4APA into mouse cerebral synaptosomes at 4° C. (dashed lines) and 30° C. (solid lines). The y-axis represents the synaptosome concentration of 4APA (nmol/mg protein) determined following incubation with 10 μM (R)-4APA, (S)-4APA or rac-4APA for up to 30 min at 37° C. or 4° C. (n=3 samples per group). Two-way ANOVA was significant for compound/temperature (P<0.0001), time (P<0.0001), and interaction (P<0.0001). Tukey's multiple comparison test had P<0.0001 for concentration at 37° C. vs. 4° C. for each compound; synaptosome concentration at 37° C. was significantly different for (R)-4APA vs. (S)-4APA (****P<0.0001), (R)-4APA vs. rac-4APA (++++P<0.0001), and (S)-4APA vs. rac-4APA (^^^^P<0.0001).

Figures 19A, 19B:
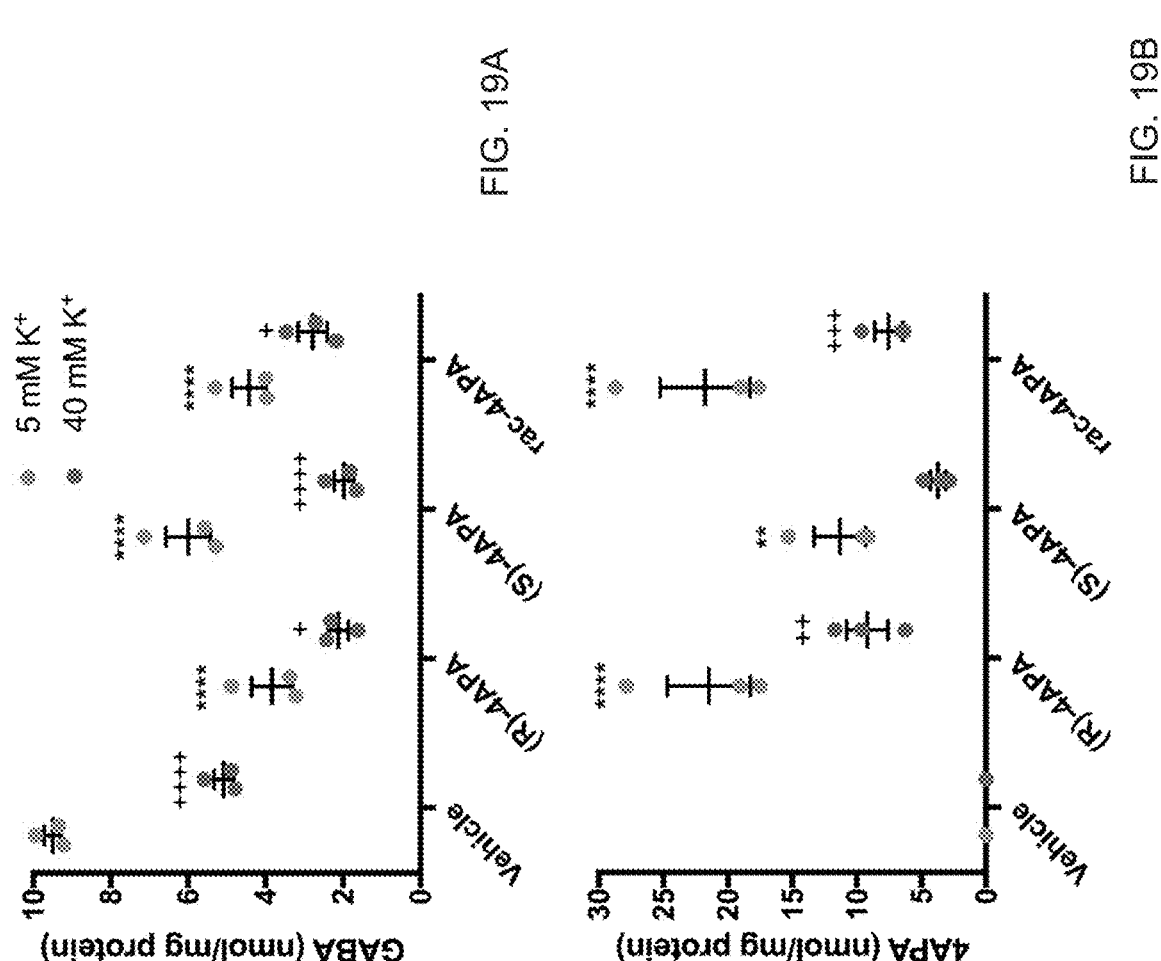

FIGS. 19A-19B. Impact of 4APA enantiomers on endogenous GABA in mouse cerebral synaptosomes. Synaptosome concentration of GABA and 4APA (nmol/mg protein) was determined following incubation with (R)-4APA, (S)-4APA or rac-4APA (100 μM) or vehicle for 15 min at 37° C. followed by incubation with 5 mM $K^+$ or 40 mM $K^+$ for 15 min at 37° C. (n=3 samples per group). (A) GABA concentration: Two-way ANOVA was significant for exposure (P<0.0001), low vs. high $K^+$ concentration (P<0.0001), and interaction (P<0.01). Sidak's multiple comparison test had **P<0.0001 for GABA concentration with each compound vs. vehicle, and ++++P<0.0001 or +P<0.05 for GABA concentration with low vs. high $K^+$ concentration for each compound or vehicle. (B) 4APA concentration: Two-way ANOVA was significant for exposure (P<0.0001), low vs. high $K^+$ concentration (P<0.0001), and interaction (P<0.05). Sidak's multiple comparison test had P<0.0001 or P<0.01 for 4APA concentration with each compound vs. vehicle, and +++P<0.001 or ++P<0.01 for 4APA concentration with low vs. high $K^+$ concentration for each compound or vehicle.

FIGS. 20A-20B. Pharmacokinetics of 4APA compounds measured in serum and brain after single IP injection of 100 mg/kg into 2 to 3 month-old, male, C57Bl/6 mice (n=3 mice per group). (A) Concentrations are expressed as pmol/L in serum samples (solid lines) and pmol/mg protein in brain samples (dashed lines). Results are plotted for each measurement. In brain, repeated measures two-way ANOVA was significant for 4APA enantiomer (P<0.001) and time (P<0.01); Sidak's multiple comparisons test was significant only for 0.5 hr vs. 4 hr for (S)-4APA (+P<0.05). In serum, repeated measures two-way ANOVA was significant for time (P<0.0001) and interaction (P<0.01); for both enantiomers, Sidak's multiple comparisons test was significant only for the initial time point vs all others 0.5 hr vs. 4 hr for S-4APA (***P<0.001). (B) $C_{max}$, $T_{max}$, and $T_{1/2}$ values (mean±SEM) are presented for each enantiomer in serum and brain; there was no significant difference in any of these three pharmacokinetic measures between the two enantiomers.

Figures 21A, 21B:
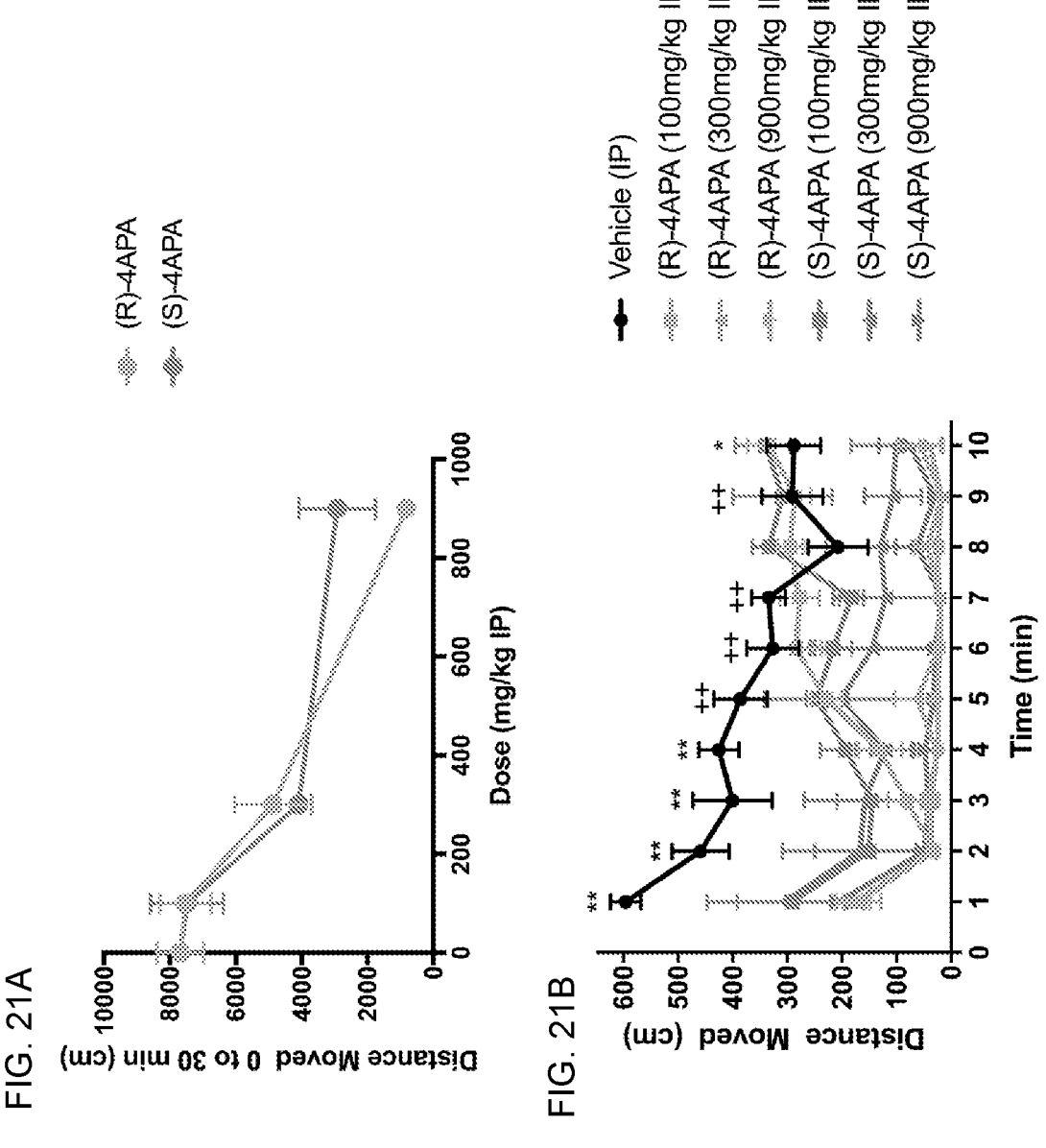

FIGS. 21A-21B. Exploratory and locomotor behavior in 2 month-old male C57Bl/6 mice were assessed in the novel cage test immediately following single injection with compound or vehicle (n=3 mice per group). (A) Dose-response relationships for (R)-4APA and (S)-4APA for total distance moved over the 30 minutes following injection. Time courses of distance moved over the initial 10 minutes. Two-way ANOVA had $F_{interaction}$ P=0.40, $F_{Dose}$ P<0.0001, and $F_{Enantiomers}$ P=0.38. (B) For distance moved over the initial 10 minutes following injection. Two-way repeated measures ANOVA had $F_{interaction}$ P<0.0001, $F_{Time}$ P<0.0001, and $F_{Exposure}$ P=0.0001. Tukey's multiple comparisons test had all concentrations of both enantiomers significantly different from vehicle at 1 to 4 minutes (**P<0.01); at 5 to 7 and at 9 minutes, 300 mg/kg of (R)-4APA and 900 mg/kg of both enantiomers were significantly different from vehicle (++P<0.01); and at 10 minutes, only (R)-4APA at the higher two doses were significantly different from vehicle (*P<0.05). At no time were the same dose of R and S enantiomers significantly different from each other.

Figure 22:
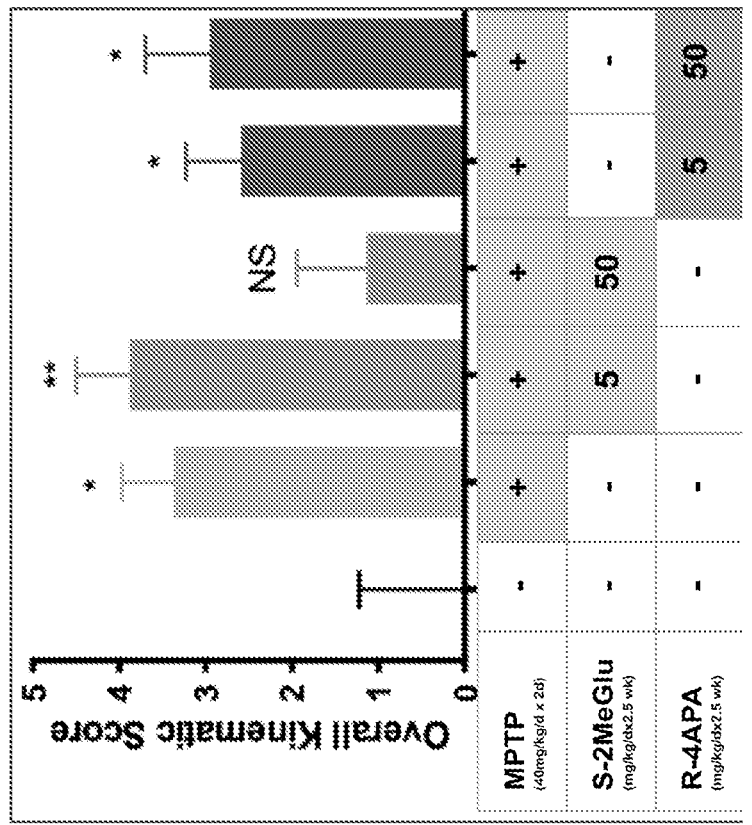

FIG. 22. Nine week old male C57Bl/6 mice (n=14 per group) were treated with vehicle, 5 or 50 mg/kg/day S-2Me-Glu or R-4APA IP from day −5 to 14, and vehicle or 40 mg/kg/day MPTP IP on days 1 and 2. Higher overall kinematic score indicates greater impairment in gait and balance. ANOVA had P<0.01 and Sidak's multiple comparison test was performed for each group v. Veh/Veh (*P<0.05, **P<0.01, NS had P=0.32.

Figure 23:
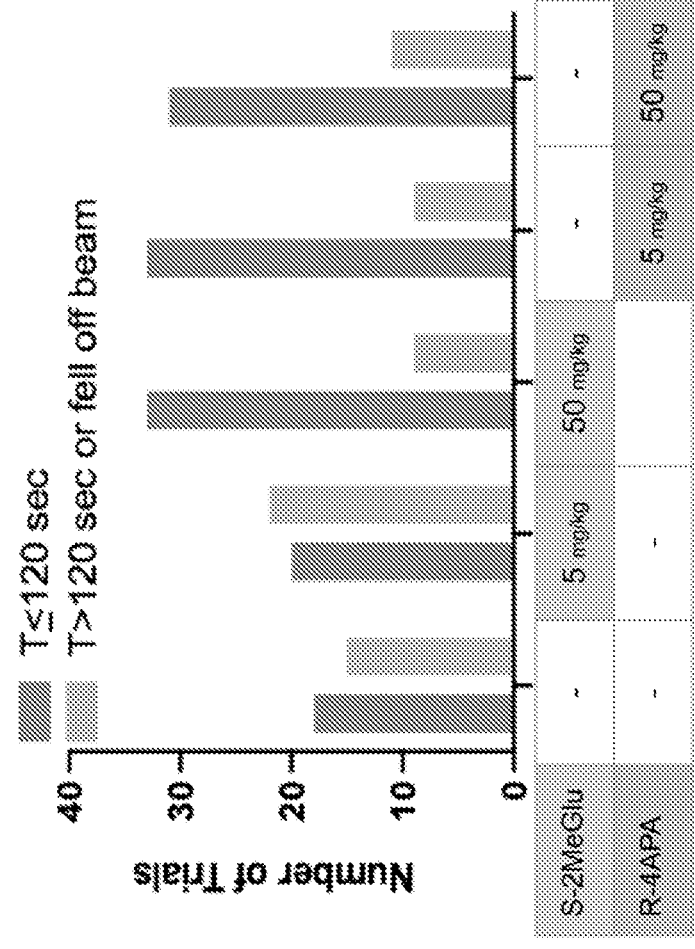

FIG. 23. Eight week old male Line 61 mice (n=14 per group) were treated with vehicle, 5 or 50 mg/kg/d S-2MeGlu or R-4APA IP from day 1 to day 7 and then motor function tested using the tapered beam test. Mice were categorized as those who completed the task within 120 seconds or those that either fell off the beam or took longer than 120 seconds. Chi-squared test had P<0.005.

Figure 24:
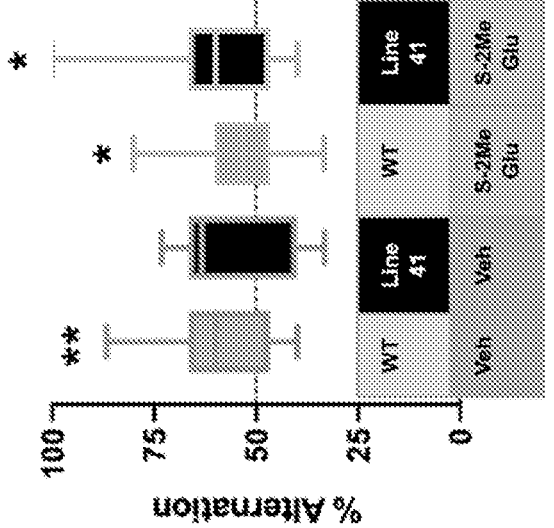

FIG. 24. Percent alternation in Y maze for wild-type (WT) or Line 41 transgenic mice treated with vehicle or 10 mg/kg IP S-2MeGlu (n=14 four month old males per group). WT/Veh were significantly different from random (50%) alternation (**P<0.01) while Line 41/veh were not significantly different from random, indicating impaired working memory in the transgenic mice. Both groups treated with S-2MeGlu had percent alternation significantly different from random (*P<0.05).

Figure 25:
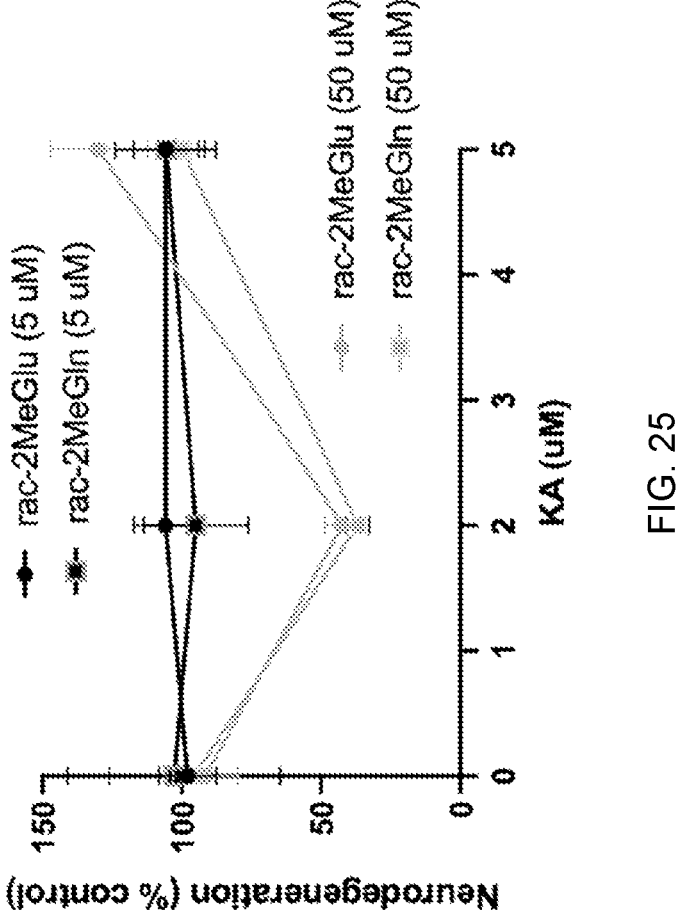

FIG. 25. Efficacy of 2MeGlu, 2MeGln, and 4APA to prevent neurodegeneration. Mouse hippocampal slice cultures were exposed to kanic acid (KA) to induce dose dependent neurodegeneration as determined with propridium iodide staining. Slice cultures were incubated with with 5 or 50 micromolar racemic (rac) 2MeGlu, 2MeGln, or 4APA. At the lower dose of KA, the higher dose of 2MeGlu or 2MeGln (50 μM) substantially reduced neurodegeneration by approximately 50% (FIG. 25). Neither dose of 2MeGlu or 2MeGln was neuroprotective at the higher dose of KA. 4APA was not neuroprotective in this model at either 5 or 50 μM (not shown in FIG. 25).

FIG. 26. Four adult mice (M1 to M4) were injected with radiolabeled 2MeGlu either with 2.5 mg of non-radioactive 2MeGlu (M1) or without cold spike (M2 to M4), and then imaged by PET. [11]C-2MeGlu showed a rapid rise in brain radioactivity (3% ID/g) that mostly cleared within the first 10 minutes, and is likely related to labeled compound in blood. Longer time points showed about 0.5% of the injected dose was retained throughout the brain for up to 40 minutes following injection, with greater apparent brain retention in the non-spiked injections.

DETAILED DESCRIPTION

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "subject," "individual," and "patient" are used interchangeably herein to refer to a mammal being assessed for treatment and/or being treated. In some embodiments, the mammal is a human. The terms "subject," "individual," and "patient" encompass, without limitation, individuals having a disease. Subjects may be human, but also include other mammals, particularly those mammals useful as laboratory models for human disease, e.g., mice, rats, etc.

The term "diagnosis" is used herein to refer to the identification of a molecular or pathological state, disease or condition in a subject, individual, or patient.

The term "prognosis" is used herein to refer to the prediction of the likelihood of death or disease progression, including recurrence, spread, and drug resistance, in a subject, individual, or patient. The term "prediction" is used herein to refer to the act of foretelling or estimating, based on observation, experience, or scientific reasoning, the likelihood of a subject, individual, or patient experiencing a particular event or clinical outcome. In one example, a physician may attempt to predict the likelihood that a patient will survive.

As used herein, the terms "treatment," "treating," and the like, refer to administering an agent, or carrying out a procedure, for the purposes of obtaining an effect on or in a subject, individual, or patient. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a neurologic disease in a mammal, particularly in a human, and includes: (a) inhibiting the disease, i.e., arresting its development; and (b) relieving the disease or its symptoms, i.e., causing regression of the disease or its symptoms.

Treating may refer to any indicia of success in the treatment or amelioration or prevention of a disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of an agent to prevent or delay, to alleviate, or to arrest or inhibit development of the symptoms or conditions associated with disease or other diseases. The term "therapeutic effect" refers to the reduction, elimination, or prevention of the disease, symptoms of the disease, or side effects of the disease in the subject.

As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

"In combination with", "combination therapy" and "combination products" refer, in certain embodiments, to the concurrent administration to a patient of the agents described herein in combination with additional therapies, e.g. surgery, treatment with other compounds, and the like. When administered in combination, each component can be administered at the same time or sequentially in any order at different points in time. Thus, each component can be administered separately but sufficiently closely in time so as to provide the desired therapeutic effect.

"Concomitant administration" means administration of one or more components, such as active agents, at such time that the combination will have a therapeutic effect. Such concomitant administration may involve concurrent (i.e. at the same time), prior, or subsequent administration of components. A person of ordinary skill in the art would have no difficulty determining the appropriate timing, sequence and dosages of administration.

The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

The term "sample" with reference to a patient encompasses CSF, blood and other liquid samples of biological origin, solid tissue samples such as a biopsy specimen or tissue cultures or cells derived therefrom and the progeny thereof. The term also encompasses samples that have been manipulated in any way after their procurement, such as by treatment with reagents; washed; or enrichment for certain cell populations, such as diseased cells. The definition also includes samples that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's diseased cell, e.g., a sample comprising polynucleotides and/or polypeptides that is obtained from a patient's diseased cell (e.g., a cell lysate or other cell extract comprising polynucleotides and/or polypeptides); and a sample comprising diseased cells from a patient. A biological sample comprising a diseased cell from a patient can also include non-diseased cells.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a KD (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, 10-12 M or less, 10-13 M or less, 10-14 M or less, 10-15 M or less, or 10-16 M or less). "Affinity" refers to the strength of binding, increased binding affinity being correlated with a lower Kd.

Compounds

A neurotransmitter is a signaling molecule secreted by a neuron to affect another cell across a synapse. The cell receiving the signal, any main body part, or target cell, may be another neuron, but could also be a gland or muscle cell. Neurotransmitters are released from synaptic vesicles into the synaptic cleft where they are able to interact with neurotransmitter receptors on the target cell. The neurotransmitter's effect on the target cell is determined by the receptor it binds. Multiple neurotransmitters are synthesized from simple precursors such as amino acids, which are readily available and often require a small number of biosynthetic steps for conversion.

A neurotransmitter may have an excitatory, inhibitory or modulatory effect on the target cell. The effect is determined by the receptors the neurotransmitter interacts with at the post-synaptic membrane. Neurotransmitters can influence transmembrane ion flow either to increase (excitatory) or to decrease (inhibitory) the probability that the cell with which it comes in contact will produce an action potential.

A false neurotransmitter is a compound that is not a neuron's normal neurotransmitter but that can be taken up by the neuron, stored in its vesicles, and released along with the neuron's normal neurotransmitter when the neuron is stimulated. False neurotransmitters can have therapeutic value for their ability to compete with the normal neurotransmitter for synaptic release, without acting on the receptors activated by the normal neurotransmitter. In some embodiments, a false neurotransmitter has substantially decreased activation of the cognate receptor for the neurotransmitter, e.g. less than 50% activation, less than 25% activation, less than 10% activation, less than 5% activation, less than 1% activation, or less, compared to the normal neurotransmitter, i.e. glutamate or GABA.

Fluorescent false neurotransmitters are of interest for imaging purposes, and can act as substrates for the synaptic vesicle transporter. These optical tracers enable visualization of neurotransmitter uptake and release from synaptic terminals.

Glutamatergic neurons use glutamate, which is one of the most common excitatory neurotransmitters in the central nervous system (CNS). Glutamate receptors are present on presynaptic and postsynaptic neurons as well as on glial cells. These include both ionotropic receptors (NMDA, AMPA/KA) and metabotropic receptors (mGluRs). The effect of Glu is determined by the receptor subtype, localization (synaptic, perisynaptic and extrasynaptic), and interactions with various scaffolding and signaling proteins (not shown) in the postsynaptic density. Glu receptor stimulation results not only in rapid ionotropic effects but also synaptic plasticity, e.g. long-term potentiation (LTP) and long-term depression (LTD), via cognate signal transduction cascades. Excitotoxicity has been implicated in certain chronic diseases including ischemic stroke, epilepsy, amyotrophic lateral sclerosis, Alzheimer's disease, Huntington disease, and Parkinson's disease.

Enantiomerically pure compositions are provided of 2MeGlu, including (S)-2-MeGlu. (S)-2-MeGlu is not a substrate for GAD or GLDH and does not progress through the GABA shunt or oxidative deamination. The S enantiomer (L isomer by the convention used for natural amino acids) is shown herein to be avidly transported into synaptosomes and stored and released like L-Glu. While substituting for L-Glu in the neurotransmitter pool, (S)-2MeGlu does not have significant activity across a broad spectrum of glutamate and GABA receptors, and is therefore a false neurotransmitter. Only the (S)-2MeGlu enantiomer is a substrate for glutamine synthase and thereby can enter the glutamate-glutamine cycle; however, (S)-2MeGlu is not an efficient substrate for the reverse reaction. The net effect in vivo is that the false neurotransmitter, (S)-2MeGlu, rapidly accumulates as (S)-2MeGln in the brain, which is then slowly converted back to (S)-2MeGlu. Exposure to rac-2MeGln provides for comparable but more rapid appearance of 2MeGln in brain, accompanied by slow generation of 2MeGlu over time. (S)-2MeGlu or rac-2MeGln are used in methods of the disclosure as a pharmacologic agent to alter the excitatory/inhibitory balance in brain. Specifically, (S)-2-MeGlu dose-dependently rescues motor function in a model of PD. (S)-2MeGlu also improves cognitive improvement in a mouse model of AD. (S)-2MeGlu or (S)-2MeGln each suppress neurodegeneration in mouse hippocampal slice cutlrues. In other embodiments, (S)-2MeGlu or rac-2MeGln are used as imaging agents for GS expressing or Gln transporting cells.

GABA (gamma-aminobutyric acid) is used at the great majority of fast inhibitory synapses in virtually every part of the brain. GABA is formed from glutamate via the addition of glutamate decarboxylase and vitamin B6. Once GABA is formed, is it released into the post-synaptic terminals of neurons. GABA receptors are receptors that respond when GABA is released into the post-synaptic nerve terminal. They are considered the chief inhibitory receptors for the central nervous system. GABA receptors are subdivided into GABAa and GABAb. GABAa is classified as a ligand-gated ion channel/inotropic receptor. GABAa is considered in fast synaptic inhibition. Upon the receptor binding to GABA, an ion pore opens to allow chloride to move across the cell membrane. Chloride is a negatively charged ion and will follow into the area of positive charge. Typically, chloride will flow into the intracellular space. The addition of negative charge will decrease the resting potential of the cell, thus causing an inhibitory effect. GABAa receptors are located throughout the central nervous system. However, they have high concentrations in the limbic system and the retina. GABAb receptor is a G-couple protein receptor. GABAb receptors are considered slow synaptic inhibitors. After GABA has bound to the receptor, potassium conductance is increased. Adenylyl cyclase is activated, which prevents calcium entry thus inhibits presynaptic release of other neurotransmitters. GABAb locations include the thalamic pathways and cerebral cortex.

False neurotransmitters and imaging agents for gabaergic neurons include enantiomers of 4-aminopentanoic acid (4APA). Enantiomers of 4APA selectively replace GABA in synaptosomes, but have little or no activity on a broad panel GABA and glutamate receptors. In some embodiments the compound of interest is (S)-4APA or (R)-4APA, which are shown herein to be GABAergic false neurotransmitters. R-4APA is shown to rescue motor function in a model for PD.

The compounds of the disclosure, or pharmaceutically acceptable salt thereof, have one or more stereocenters, which can be separated to utilize individual enantiomers and/or diastereomers. Methods to generate individual diastereomers and/or enantiomers are known in the art, including, but not limited to, chromatography, such as chiral chromatography, e.g., supercritical fluid chromatography on a chiral amylose column, and diastereoselective and/or enantioselective synthesis using a chiral auxiliary, for example, organometallic addition to a chiral sulfinimine. See, for instance, procedures described in Example 1 and 2. In some embodiments, the compound is enantiomerically enriched, and is present in from about 90% to about 99.999% enantiomeric excess (ee), such as from about 90% to about 99.99%, from about 93% to about 99.99%, from about 95% to about 99.99%, from about 95% to about 99.9%, from about 97% to about 99.9%, from about 98% to about 99.9%, or from about 99% to about 99.99% ee. Absent any other indication, the predominant isomer is the stereochemistry shown in the compound structure herein. In some embodiments, the compound is predominantly the R isomer. In some embodiments, the compound is predominantly the S isomer.

A compound, e.g. a false neurotransmitter, including without limitation (S)-2-MeGlu, or (R)-4APA, can be formulated with an a pharmaceutically acceptable carrier (one or more organic or inorganic ingredients, natural or synthetic, with which a subject agent is combined to facilitate its application). A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

As used herein, a "therapeutically effective amount" refers to that amount of the therapeutic agent sufficient to treat or manage a disease or disorder. A therapeutically effective amount may refer to the amount of therapeutic agent sufficient to delay or minimize the onset of disease, e.g., to delay or minimize neurologic disease. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

Typically the dosage of agent in a formulation will be from about 0.1 mg of agent per kg subject body weight/day up to about 1000 mg/kg/d; for example from 0.5 mg/kg/d; 1 mg/kg/d; 5 mg/kg/d; 10 mg/kg/d; 20 mg/kg/d; 50 mg/kg/d; 75 mg/kg/d; 100 mg/kg/d; 200 mg/kg/d; 250 mg/kg/d; 500 mg/kg/d; 750 mg/kg/d; up to about 100 mg/kg/d; or more.

Doses in the range of 0.01 to 1 mg per kilogram of patient body weight may be utilized for a radionuclide therapeutic composition which is administered intrathecally. Relatively large doses, in the range of 0.1 to 10 mg per kilogram of patient body weight, may used for imaging agents with a relatively non-toxic imaging moiety. The amount utilized will depend on the sensitivity of the imaging method, and the relative toxicity of the imaging moiety.

For imaging or therapeutic use, dosage and frequency may vary depending on the half-life of the agent in the patient. It will be understood by one of skill in the art that such guidelines will be adjusted for the molecular weight of the active agent, the clearance from the blood, the mode of administration, and other pharmacokinetic parameters. The dosage may also be varied for localized administration, e.g. intranasal, inhalation, etc., or for systemic administration, e.g. i.m., i.p., i.v., oral, and the like.

An active agent can be administered by any suitable means, including topical, oral, parenteral, intrapulmonary, and intranasal. Parenteral infusions include intramuscular, intravenous (bolus or slow drip), intraarterial, intraperitoneal, intrathecal or subcutaneous administration. An agent can be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the disclosure, by such means as depot injections or erodible implants.

Salts include but are not limited to: Na, K, Ca, Mg, ammonium, tetraalkyl ammonium, aryl and alkyl sulfonates, phosphates, carboxylates, sulfates, Cl, Br, and guanidinium.

Unless otherwise specified, reference to an atom is meant to include isotopes of that atom. For example, reference to H is meant to include 1H, 2H (i.e., D) and 3H (i.e., T), and reference to C is meant to include 12C and all isotopes of carbon (such as 13C).

Salts, solvates, hydrates, and prodrug forms of a compound are of interest. Polymorphic, pseudo-polymorphic, amorphous and co-crystal forms of a compound are also of interest. All such forms are embraced by the present disclosure. Thus, the compounds described herein include salts, solvates, hydrates, prodrug, enantiomer, and isomer forms thereof, including the pharmaceutically acceptable salts, solvates, hydrates, prodrugs and isomers thereof.

Conditions of Interest for Treatment

Metabolism of glutamate, the main excitatory neurotransmitter and precursor of GABA, is exceedingly complex and highly compartmentalized in brain. Maintenance of these neurotransmitter pools is dependent on the de novo synthesis of glutamine in astrocytes which requires both the anaplerotic enzyme pyruvate carboxylase and glutamine synthetase. Glutamate is formed directly from glutamine by deamidation via phosphate activated glutaminase a reaction that also yields ammonia. Glutamate plays key roles linking carbohydrate and amino acid metabolism via the tricarboxylic acid (TCA) cycle, as well as in nitrogen trafficking and ammonia homeostasis in brain. As both glutamate and GABA serve dual roles in the brain as metabolites and important neurotransmitters mediating excitatory and inhibitory signals, respectively, their metabolic pathways are of significant interest. The immediate precursor for neuronal synthesis of glutamate is glutamine. This reaction is catalyzed by phosphate activated glutaminase (PAG) which hydrolytically deamidates glutamine to form glutamate and ammonia. Glutamine synthetase (GS), the enzyme that converts glutamate to glutamine, is localized in astrocytes.

Compounds of the invention act on the balance between excitatory (glutamate-mediated), and inhibitory (GABA-mediated) neurotransmission, by competing in the glutamate or GABA pools without activating receptors.

Neurodegenerative disorders included within the methods of the present disclosure include, Parkinsons disease, including neurological disorders that share symptoms similar to those seen in Parkinson's disease related disorders. In some cases, the neurological disorders may show symptoms similar to Parkinson's disease, atypical Parkinson's disease or Parkinson's plus disease. Examples include but are not limited to Drug-induced Parkinsonism, Progressive supranuclear Palsy, Vascular Parkinsonism, Dementia with Lewy Bodies, diffuse Lewy body disease, Corticobasal degeneration, multisystem degeneration (Shy-drager syndrome), Alzheimer's disease, Pick's disease, frontotemporal dementia, multiple systems atrophy, vascular dementia, and progressive supranuclear palsy (Steel-Richardson syndrome). Other conditions also included within the methods of the present invention include age-related dementia and other dementias and conditions with memory loss including vascular dementia, diffuse white matter disease (Binswanger's disease), dementia of endocrine or metabolic origin, dementia of head trauma and diffuse brain damage, dementia pugilistica and frontal lobe dementia. In some cases, the neurological disorder may not respond well to dopaminergic treatments and may be caused as a result of various vascular, drug-related, infectious, toxic, structural and other known secondary causes. Drug-induced Parkinsonism may be caused by agents that block post-synaptic dopamine D2 receptors with high affinity, such as anti-psychotic and anti-emetic medications and sodium valproate, anti-depressants, reserpine, tetrabenazine etc.

Parkinson disease is a slowly progressive, degenerative disorder characterized by resting tremor, stiffness (rigidity), slow and decreased movement (bradykinesia), and eventually gait and/or postural instability. Diagnosis is clinical. Conventional treatment aims to restore dopaminergic function in the brain with levodopa plus carbidopa and/or other drugs, e.g. dopamine agonists, monoamine oxidase type B [MAO-B] inhibitors, amantadine. For refractory, disabling symptoms in patients without dementia, stereotactic deep brain stimulation or lesional surgery and levodopa and an apomorphine pump may help.

The pathologic hallmark of Parkinson disease is synuclein-filled Lewy bodies in the nigrostriatal system; however, synuclein can accumulate in many other parts of the nervous system, including the dorsal motor nucleus of the vagus nerve, basal nucleus of Meynert, hypothalamus, neocortex, olfactory bulb, sympathetic ganglia, and myenteric plexus of the gastrointestinal tract. Lewy bodies appear in a temporal sequence, and many experts believe that Parkinson disease is a relatively late development in a systemic synucleinopathy. Other synucleinopathies (synuclein deposition disorders) include dementia with Lewy bodies and multiple system atrophy. Parkinson disease may share features of other synucleinopathies, such as autonomic dysfunction and dementia.

In Parkinson disease, pigmented neurons of the substantia nigra, locus ceruleus, and other brain stem dopaminergic cell groups degenerate. Loss of substantia nigra neurons results in depletion of dopamine in the dorsal aspect of the putamen (part of the basal ganglia) and causes many of the motor manifestations of Parkinson disease.

A genetic predisposition is likely in at least in some cases of Parkinson disease. About 10% of patients have a family history of Parkinson disease. Several abnormal genes have been identified. Inheritance is autosomal dominant for some genes and autosomal recessive for others. Mutations in leucine-rich repeat kinase 2 (LRRK2) is among the most prevalent mutation in Parkinson disease patients, and it is the most prevalent autosomal dominant mutation of the inherited forms of the disease.

Diagnosis of Parkinson disease is clinical. Parkinson disease is suspected in patients with characteristic unilateral resting tremor, decreased movement, or rigidity. During finger-to-nose coordination testing, the tremor disappears (or attenuates) in the limb being tested. During the neurologic examination, patients cannot perform rapidly alternating or rapid successive movements well. Sensation and strength are usually normal. Reflexes are normal but may be difficult to elicit because of marked tremor or rigidity. Slowed and decreased movement due to Parkinson disease must be differentiated from decreased movement and spasticity due to lesions of the corticospinal tracts. To help distinguish Parkinson disease from secondary or atypical parkinsonism, clinicians often test responsiveness to levodopa. A large, sustained response strongly supports Parkinson disease.

Levodopa is the most effective current treatment. However, when Parkinson disease is advanced, sometimes soon after diagnosis, response to levodopa can be complex, causing fluctuations in motor symptoms and dyskinesias. To reduce the time levodopa is taken and thus minimize these effects, clinicians can consider treating younger patients who have mild disability with MAO-B inhibitors (selegiline, rasagiline), Dopamine agonists (eg, pramipexole, ropinirole, rotigotine), Amantadine (which is also the best option when trying to decrease peak-dose dyskinesias). However, if these drugs do not sufficiently control symptoms, clinicians should promptly initiate levodopa because it can usually greatly improve quality of life. Evidence now suggests that levodopa becomes ineffective because of disease progression rather than cumulative exposure to levodopa.

Deep brain stimulation of the subthalamic nucleus or globus pallidus interna is often recommended for patients with levodopa-induced dyskinesias or significant motor fluctuations; this procedure can modulate overactivity in the basal ganglia and thus decrease parkinsonian symptoms in patients with Parkinson disease. For patients with tremor only, stimulation of the *ventralis* intermediate nucleus of the thalamus is sometimes recommended; however, because most patients also have other symptoms, stimulation of the subthalamic nucleus, which relieves tremor as well as other symptoms, is usually preferred. When the main problem is inadequate control of dyskinesias or when patients have an increased risk of cognitive decline, the globus pallidus interna is a good target.

Suitable subjects include any subject who displays symptoms of Parkinson's disease such as bradykinesia, repetitive movements, tremors, limb rigidity, gait and balance problems, inability to aim the eyes due to weakness of eye muscles, weakness, sensory loss, non-motor manifestations such as REM sleep behavior disorder, neuropsychiatric symptoms including mood disturbances and cognitive changes, anxiety, apathy, changes in thinking ability, level of attention or alertness and visual hallucinations, intellectual and functional deterioration, forgetfulness, personality changes, autonomic dysfunction affecting cardiovascular, respiratory, urogenital, gastrointestinal and sudomotor function, difficulties in breathing and swallowing, inability to sweat, orthostatic hypotension, pain, constipation, and loss of olfaction, e.g., hyposmia. In some embodiments, the subjects may experience predominant speech or language disorder, predominant frontal presentation and gait freezing. The methods of the invention improve one or more disease indicia, particularly including motor deficits.

In some embodiments, the subject may not display any overt symptoms of Parkinson's disease. In some cases, the subject in need may show increased susceptibility to infections, hypothermia, weaker bones, joint stiffness, arthritis, stooped posture, slowed movements, decrease in overall energy, constipation, urinary incontinence, memory loss, slower thinking, slower reflexes, difficulty with balance, decrease in visual acuity, diminished peripheral vision, hearing loss, wrinkling skin, greying hair, weight loss, loss of muscle tissue.

In some embodiments, the subject is selected from those that have been diagnosed as having Alzheimer's disease. In a clinical sense, an effective amount is an amount of agent that, when administered for a suitable period of time, usually at least about one week, and maybe about two weeks, or more, up to a period of about 4 weeks, 8 weeks, 12 weeks, or longer will evidence an alteration in the symptoms of cognitive impairment in an individual with Alzheimer's Disease relative to a healthy individual. For example, an effective dose is the dose that when administered for a suitable period of time will slow e.g. by about 20% or more, e.g. by 30% or more, by 40% or more, or by 50% or more, in some instances by 60% or more, by 70% or more, by 80% or more, or by 90% or more, or halt cognitive decline, i.e. stabilize the cognitive abilities. In some embodiments, an effective amount or dose may not only slow or halt the progression of the disease condition but may also induce the reversal of the condition. For example, an effective dose may improve the cognition in an individual with Alzheimer's Disease by, for example 1.5-fold, 2-fold, 3-fold, 4-fold, 5-fold, in some instances 6-fold, 7-fold, 8-fold, 9-fold, or 10-fold or more.

Methods for measuring cognition or vision are also well known in the art, any of which may be used to determine an effective dose. Examples include tests such as cognition tests and IQ test for measuring cognitive ability, e.g. attention and concentration, the ability to learn complex tasks and concepts, memory, information processing, visuospatial function, the ability to produce and understanding language, the ability to solve problems and make decisions, and the ability to perform executive functions; for example, the General Practitioner Assessment of Cognition (GPCOG) test, the Memory Impairment Screen, the Mini Mental State Examination (MMSE), the California Verbal Learning Test, Second Edition, Short Form, for memory, the Delis-Kaplan Executive Functioning System test, and the like. Examples of vision tests include, for example, visual acuity tests, fundoscopy, and the like.

In some embodiments, the composition may be provided in conjunction with a second agent that has been demonstrated in the art to treat a neurodegenerative disease or cognitive impairment. For example, a number of agents have been shown to have some efficacy in treating the cognitive symptoms of Alzheimer's disease (e.g., memory loss, confusion, and problems with thinking and reasoning), e.g. cholinesterase inhibitors (e.g. Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g. citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon).

In some aspects of the subject methods, the method further comprises the step of measuring cognitive ability, vision, synaptic plasticity, etc. after treatment, e.g. using the methods described herein or known in the art; and detecting a decreased rate of cognitive decline/visual decline/loss of synaptic plasticity, a stabilization of cognitive ability/visual ability/synaptic plasticity, and/or an increase in cognitive ability/visual ability/synaptic plasticity after administration of the subject compositions as compared to the cognitive ability/visual ability/synaptic plasticity of the individual before the subject composition was administered. In some instances, the determination is made by comparing the results of the cognition test, vision test or synaptic plasticity test to the results of the test performed on the same individual at an earlier time, e.g. 1 week earlier, 2 weeks earlier, 1 month earlier, 2 months earlier, 3 months earlier, 6 months earlier, 9 months earlier, 1 year earlier, 2 years earlier, 5 years earlier, or 10 years earlier, or more. In other instances, the determination is made by comparing the results of the cognition test, vision test, or synaptic plasticity test to the results of the test performed on a reference individual, e.g. a healthy individual that does not suffer from any greater cognitive or visual impairment than that associated with the natural aging process.

By "cognition" it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). Cognition is a faculty for the processing of information, applying knowledge, and changing preferences. By "cognitive plasticity" it is meant the ability to learn, e.g., the ability to learn complex tasks and concepts, analogous to the ability to learn of an organism that is undifferentiated such as a newborn or juvenile, e.g., a human from the time of birth to pre-pubertal age of about 10 years. By "cognitive decline", it is meant a progressive decrease in cognition, as evidenced by, for example, a decline in one or more of, e.g., attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "an impairment in cognitive ability", "reduced cognitive function", and "cognitive impairment", it is meant a reduction in cognitive ability relative to a healthy individual, e.g. an age-matched healthy individual, or relative to the ability of the individual at an earlier point in time, e.g. 2 weeks, 1 month, 2 months, 3 months, 6 months, 1 year, 2 years, 5 years, or 10 years or more previously.

By "vision" it is meant the ability to see objects. By "visual decline", it is meant a progressive decrease over time in the acuity of an individual's vision, i.e. the sharpness of vision. By "reduced vision" or "reduced visual function" it is meant an impairment in vision relative to a healthy individual, e.g. an age-matched healthy individual. Methods for measuring visual acuity and visual function are also well known in the art, any of which may be used to identify an individual in need of treatment by the subject methods and/or responsiveness of an individual to treatment by the subject methods. These include, for example, measuring the ability of the individual to discern letters or numbers at a given distance according to a fixed standard. In some instances, the reference may be the results of a visual acuity test performed by one or more age-matched individuals that either experience reduced visual function (i.e. positive controls) or do not experience reduced visual function (i.e. negative controls). In some instances, the reference may be the results of the task performed by the same individual at an earlier age, e.g. 1 week earlier, 1 month earlier, 3 months earlier, 6 months earlier, 9 months earlier, and the like, for example to determine if the individual is suffering from visual decline.

The excitatory/inhibitory imbalance may be a common pathophysiological mechanism and hence a treatment target in autism spectrum disorder (ASD). For instance, abnormalities in the expression of glutamate and GABA receptors have been observed in the postmortem brains of people with ASD. In vivo, proton magnetic resonance spectroscopy ([1H]MRS) has revealed alterations in the levels of glutamate and glutamine in the cortex and basal ganglia of children, and in the basal ganglia in adults with ASD. Moreover, reductions in GABA have been reported in several brain regions in children with ASD. Electrophysiological and biochemical investigations in animal models of ASD have revealed brain region- and model-specific imbalances in E/I function.

A convulsive syndrome is a multi-causal phenomenon in which a relatively common phenomenon is the decrease or absence of neuronal inhibition mediated by GABA. The decrease of inhibitory GABAergic tone is associated with an increase in neuronal excitability that favors the hyper synchronization of neuronal electrical activity and the appearance of convulsive episodes. This can trigger numerous pathological processes such as epileptic states. Studies in humans have shown that the expression of the transporter for GABA is diminished in the hippocampus of epileptic patients, which probably leads to the increase of GABA in the synaptic cleft; as a response, the internationalization of GABA receptors into the cytoplasm (down regulation) and their reduction in number in the cell membrane occurs and this decreases the response to GABA and increases the action of excitatory neurotransmitters.

Experimental evidence shows a relationship between impaired GABAergic function and affective disorders such as stress, anxiety, depression and addictive behaviors, especially related to alcoholism.

Anxiety and depression are disorders of affect that often occur simultaneously in the same patient and some researchers have suggested that both pathologies may have a similar pathophysiological mechanism. A reduction of GABAergic tone may be present in both anxiety disorders and more complex pathologies such as major depression. Studies of cerebral functional images in patients with depression have shown lower levels of GABA at the cortical level and in experimental models in rats it has been observed that a decrease in the expression of GABA-A receptors generates a pattern of behavior similar to anxiety. GABA has also been implicated in the pathophysiology of panic disorder along with serotonin and dopamine.

The neurobiological effects of alcoholism, such as acute and chronic intoxication, convulsive episodes, psychotic states, Wernicke-Korsakoff syndrome and alcohol-fetal syndrome, are the expression of the effects and consequences of ethanol, a GABAergic agonist, on the glutamatergic system. Acute consumption of ethanol facilitates GABAergic transmission (by increasing the conductance of chlorine through the GABA receptor) and inhibits glutamatergic function (by decreasing cathonic conductance through the NMDA receptor). Paradoxically, the development of tolerance associated with the chronic consumption of ethanol leads to a reduction in GABAergic function and an increase in glutamatergic activity. The prolonged inhibition of the NMDA receptor by ethanol results in the development of super sensitivity, and acute withdrawal of ethanol causes a marked increase in the activity of postsynaptic neurons that include various circuits such as the dopaminergic, noradrenergic and glutamatergic system that can lead to neurotoxicity by glutamate.

GABA has also been implicated in the pathophysiology of schizophrenia. GABA function is diminished in brain areas that present structural changes observed in computerized axial tomography and magnetic resonance studies. These reported structural changes are associated with the patient's negative symptoms, poor premorbid functioning and decreased turnover of dopamine and serotonin. There are other findings, both in schizophrenic patients and in animal models, related to GABA: reduction in the density of GABAergic neurons, structural alterations of the receptors and disorders in the reuptake of this neurotransmitter. This accumulated evidence suggests the participation of GABA in the genesis of this disease.

GABAergic agents are an option in the treatment of epilepsy in order to increase the inhibitory tone to reduce neuronal cortical hyperexcitability.

Imaging In Vivo

In some embodiments, methods provided for imaging use in vivo, e.g., to locate or identify sites where cells of interest involved in glutamate or glutamine metabolism are present. In these embodiments, a detectably-labeled agent is administered to an individual (e.g., by injection), and labeled cells are located using standard imaging techniques, including, but not limited to, positron emission tomography, magnetic resonance imaging, computed tomography scanning, and the like.

For diagnostic in vivo imaging, the type of detection instrument available is a major factor in selecting a given radionuclide. The radionuclide chosen must have a type of decay that is detectable by a given type of instrument. In general, any conventional method for visualizing diagnostic imaging can be utilized in accordance with this invention. Another important factor in selecting a radionuclide for in vivo diagnosis is that its half-life be long enough that it is still detectable at the time of maximum uptake by the target tissue, but short enough that deleterious radiation of the host is minimized.

The detectably labeled agent is used in conjunction with imaging techniques, in order to analyze the expression of the target. In one embodiment, the imaging method is one of PET or SPECT, which are imaging techniques in which a radionuclide is synthetically or locally administered to a patient. The subsequent uptake of the radiotracer is measured over time and used to obtain information about the targeted tissue. Because of the high-energy ($\gamma$-ray) emissions of the specific isotopes employed and the sensitivity and sophistication of the instruments used to detect them, the spatial distribution of radioactivity may be inferred from outside of the body.

Among the most commonly used positron-emitting nuclides in PET are included $^{11}C$, $^{13}N$, $^{15}O$, and $^{18}F$. Isotopes that decay by electron capture and/or $\gamma$ emission are used in SPECT, and include $^{123}I$ and $^{99}mTc$.

Thus, suitable imaging labels include radiography moieties (e.g. heavy metals and radiation emitting moieties), positron emitting moieties, magnetic resonance contrast moieties, and optically visible moieties (e.g., fluorescent or visible-spectrum dyes, visible particles, etc.). Preferred radiographic labels include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Radionuclides which emit radiation capable of penetrating the skull may be useful for scintillation imaging techniques. Suitable radionuclides for labeling include $^{99}$Tc, $^{111}$In, and $^{67}$Ga. Positron emitting moieties for use in the present invention include $^{18}$F, $^{11}$C, $^{13}$N, $^{15}$O.

Preferred magnetic resonance contrast moieties include chelates of chromium(II), manganese(II), iron(II), nickel(II), copper(II), praseodymium(II), neodymium(II), samarium (III) and ytterbium(II) ion. Because of their very strong magnetic moment, the gadolinium(II), terbium(II), dysprosium(III), holmium(II), erbium(II), and iron(III) ions are especially preferred. Examples of such chelates, suitable for magnetic resonance spin imaging, are described in U.S. Pat. No. 5,733,522, incorporated fully herein by reference.

Optically visible moieties for use as imaging moieties include fluorescent dyes, or visible-spectrum dyes, visible particles, and other visible labeling moieties. Fluorescent dyes such as ALEXA dyes, fluorescein, coumarin, rhodamine, bodipy Texas red, and cyanine dyes, are useful when sufficient excitation energy can be provided to the site to be inspected visually. Endoscopic visualization procedures may be more compatible with the use of such labels.

Formulations

An agent can be administered as a pharmaceutical composition comprising a pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

As used herein, compounds which are "commercially available" may be obtained from commercial sources including but not limited to Acros Organics (Pittsburgh PA), Aldrich Chemical (Milwaukee WI, including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester PA), Crescent Chemical Co. (Hauppauge NY), Eastman Organic Chemicals, Eastman Kodak Company (Rochester NY), Fisher Scientific Co. (Pittsburgh PA), Fisons Chemicals (Leicestershire UK), Frontier Scientific (Logan UT), ICN Biomedicals, Inc. (Costa Mesa CA), Key Organics (Cornwall U.K.), Lancaster Synthesis (Windham NH), Maybridge Chemical Co. Ltd. (Cornwall U.K.), Parish Chemical Co. (Orem UT), Pfaltz & Bauer, Inc. (Waterbury CN), Polyorganix (Houston TX), Pierce Chemical Co. (Rockford IL), Riedel de Haen AG (Hannover, Germany), Spectrum Quality Product, Inc. (New Brunswick, NJ), TCI America (Portland OR), Trans World Chemicals, Inc. (Rockville MD), Wako Chemicals USA, Inc. (Richmond VA), Novabiochem and Argonaut Technology.

Compounds useful for co-administration with the active agents of the invention can also be made by methods known to one of ordinary skill in the art. As used herein, "methods known to one of ordinary skill in the art" may be identified though various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

The active agents of the invention and/or the compounds administered therewith are incorporated into a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration of the active agents and/or other compounds can be achieved in various ways, usually by oral administration. The active agents and/or other compounds may be systemic after administration or may be localized by virtue of the formulation, or by the use of an implant that acts to retain the active dose at the site of implantation.

In pharmaceutical dosage forms, the active agents and/or other compounds may be administered in the form of their pharmaceutically acceptable salts, or they may also be used alone or in appropriate association, as well as in combination with other pharmaceutically active compounds. The agents may be combined, as previously described, to provide a cocktail of activities. The following methods and excipients are exemplary and are not to be construed as limiting the invention.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Formulations are typically provided in a unit dosage form, where the term "unit dosage form," refers to physically discrete units suitable as unitary dosages for human subjects, each unit containing a predetermined quantity of active agent in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. The nature of the carrier can be either soluble or insoluble for purposes of the invention.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethyl-benzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the active agents can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in further optimizing and/or defining a therapeutic dosage range and/or a sub-therapeutic dosage range (e.g., for use in humans). The exact formulation, route of administration and dosage can be chosen by the individual physician in view of the patient's condition.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Abbreviations: 2-methylglutamate (2MeGlu), 2-methylglutamine (2MeGln), 4-aminopentanoic acid (4APA), acetonitrile (ACN), aminomethylphosphonic acid (AMPA), analysis of variance (ANOVA), bicinchoninic acid (BCA), ethylenediaminetetraacetic acid (EDTA), fluorescence imaging plate reader (FLIPR), gamma-aminobutyric acid (GABA), glutamate decarboxylase (GAD), high-potassium Krebs-Ringer phosphate buffer (K-KRP), hydrophilic interaction chromatography (HILIC), intraperitoneal (IP), Krebs-Ringer phosphate (KRP), liquid chromatography-mass spectrometry (LCMS), multiple reaction monitoring (MRM), N-Methyl-D-aspartic acid (NMDA), pharmacokinetic non-compartmental analysis (PKNCA), phosphate-buffered saline (PBS), polytetrafluoroethylene (PTFE), polyvinylidene fluoride (PVDF), Stanford Behavioral and Functional Neuroscience Laboratory (SBFNL), ultra performance liquid chromatography (UPLC).

Example 1

Enantiomers of 2-Methylglutamate and 2-Methylglutamine Selectively Impact Mouse Brain Metabolism and Behavior Imbalance of excitatory and inhibitory neurotransmission is implicated in a wide range of psychiatric and neurologic disorders. Here we tested the hypothesis that insertion of a methyl group on the stereogenic alpha carbon of L-Glu or L-Gln would impact the y-aminobutyric acid (GABA) shunt and the glutamate-glutamine cycle, which molecules can be useful as molecular imaging agents or drugs that influence behavior. (S)-2-methylglutamate, or (S)-2MeGlu, was efficiently transported into brain and synaptosomes where it was released by membrane depolarization in a manner equivalent to endogenous L-Glu. (R)-2MeGlu was transported less efficiently into brain and synaptosomes but was not released by membrane depolarization. Each enantiomer of 2MeGlu had limited activity across a panel of over 30 glutamate and GABA receptors. While neither enantiomer of 2MeGlu was metabolized along the GABA shunt, (S)-2MeGlu was selectively converted to (S)-2-methylglutamine, or (S)-2MeGln, which was subsequently slowly hydrolyzed back to (S)-2MeGlu in brain. rac-2MeGln was also transported into brain, with similar efficiency as (S)-2MeGlu. A battery of behavioral tests in young adult wild type mice showed safety with up to single 900 mg/kg dose of (R)-2MeGlu, (S)-2MeGlu, or rac-2MeGln, suppressed locomotor activity with single >100 mg/kg dose of (R)-2MeGlu or (S)-2MeGlu. No effect on anxiety or hippocampus-dependent learning was evident. Enantiomers of 2MeGlu and 2MeGln show promise as potential pharmacologic agents and imaging probes for cells that produce or transport L-Gln.

In addition to 2MeGlu, we evaluated its hypothetical metabolites, i.e., analogues of the major Glu metabolites methylated at the carbon atom located at the a position in Glu; these include: 2-methylglutamine (2MeGln, the Gln analogue), 4-aminopentanoic acid (4APA, the GABA analogue), 4OPA (4-oxopentanoic acid or levulinic acid, the SSA analogue), and 4-hydroxypentanoic acid (4HPA, the GHB analogue). α-KG and SA have no corresponding methylated analogues; the presence of the hypothetical carbon atom at the a position would not be possible without breaking the existing C—C bonds. Since α-KG and SA connect Glu to the Krebs cycle, 2MeGlu cannot enter the cycle in a Glu-like manner.

Results

We used LC-MS/MS with HILIC and chiral HILIC-like chromatography to resolve all compounds of interest, including their structural isomers, present in biological matrices over a wide range of concentrations. Introduction of a methyl group on the a carbon drastically reduced the ability of the stationary phase to resolve enantiomers compared to natural amino acids, nevertheless we achieved baseline resolution of 2MeGlu and 4APA enantiomers without prior derivatization (FIG. 8).

Figure 1A:
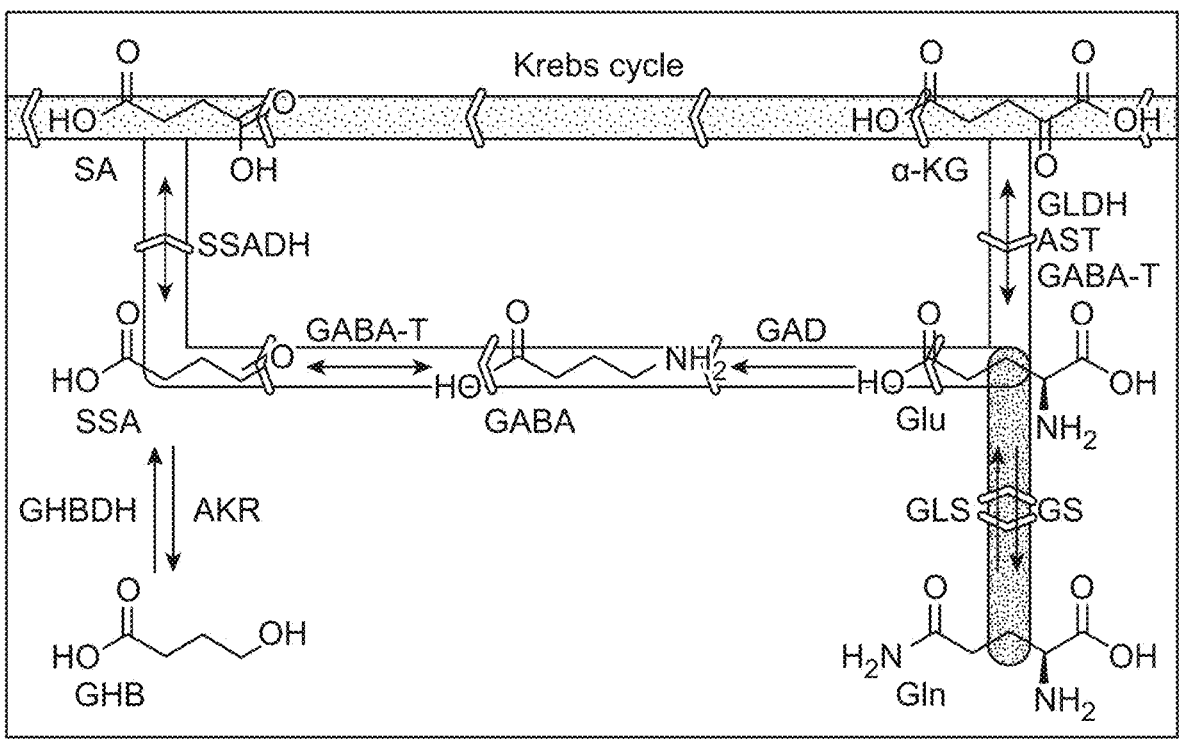
FIGS. 1A-1B. L-glutamate is involved in the GABA shunt (blue arrows) off of the Krebs cycle and in the glutamate-glutamine cycle (red arrows) (A). Glutamate amidation proceeds primarily in astrocytes (blue font), while the reverse reaction occurs in neurons (orange font). For simplicity the transport steps are not shown. Hypothetical metabolic scheme of 2MeGlu into methyl analogues of Glu metabolites (B). SA and $\alpha$-KG have no exact analogues and are not shown in the figure. Abbreviations: AKR: aldo-keto reductase, AST: aspartate transaminase, GABA-T: GABA transaminase, GAD: glutamate decarboxylase, GHBDH: gamma-hydroxybutyrate dehydrogenase, GLDH: glutamate dehydrogenase, GLS: glutaminase, GS: glutamine synthetase, SSADH: succinic semialdehyde dehydrogenase; GABA: y-aminobutyric acid, GHB: y-hydroxybutyric acid, Gln: L-glutamine, Glu: L-glutamate, a-KG: a-ketoglutarate, SA: succinic acid, SSA: succinic semialdehyde.
Figure 1B:
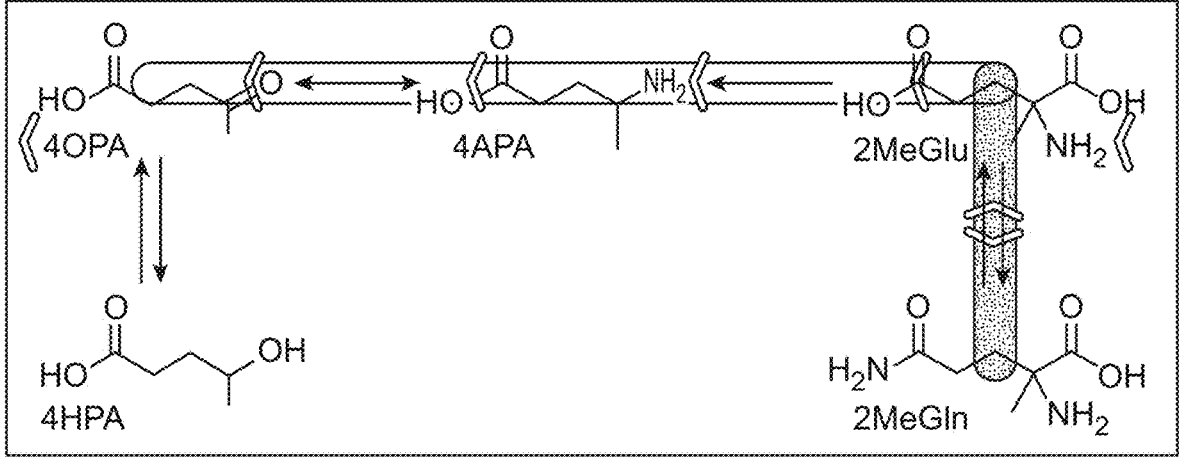
Figures 2A, 2B, 2C, 2D, 2E:
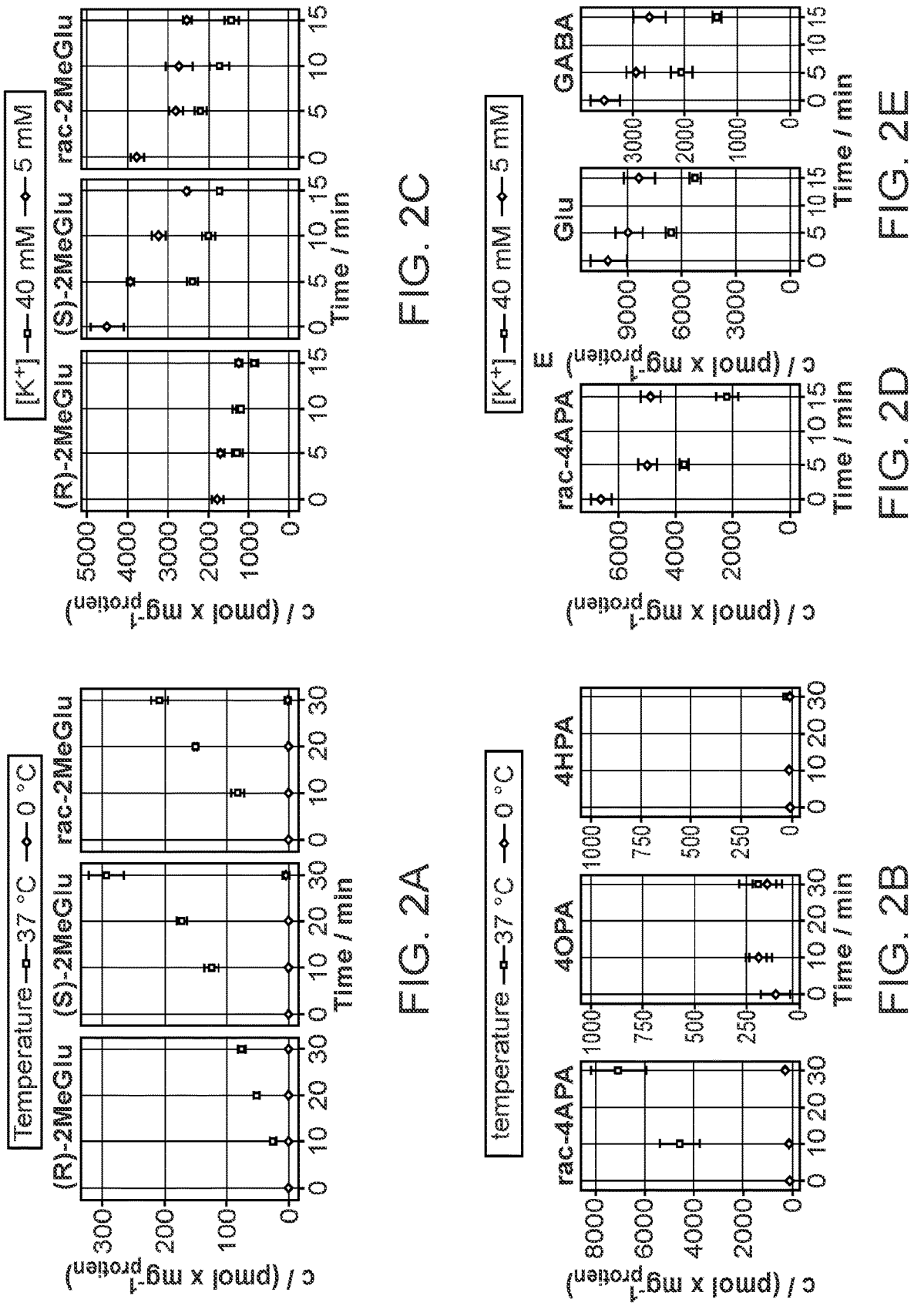
FIGS. 2A-2E. Synaptosomal accumulation of 2MeGlu (A) and 2Me analogues of the GABA shunt metabolic pathway (B). Synaptosomes were incubated with 10 $\mu$M substrates at 0° C. or 37° C. and the uptake was monitored over time. Error bars represent s.e.m., n=3. Potassium-induced release of Synaptosomal 2MeGlu (C), 4APA (D) and endogenous Glu and GABA (E). Synaptosomes were preincubated with 100 $\mu$M substrate (C,D only) for 15 min at 37° C. The pellet was washed, resuspended in normal or high-potassium KRP buffer and incubated for the times indicated at 37° C. Data are shown as mean±SEM, n=3.

Evaluation of the neurotransmitter-like properties was performed using mouse cerebral synaptosomes, a preparation of functional, mostly presynaptic, nerve terminals. Uptake of both enantiomers of 2MeGlu was temperature-dependent (FIG. 2A), although the S enantiomer (analogous to L-2MeGlu) was approximately 3-fold faster than the R enantiomer (analogous to D-2MeGlu). Among the potential 2MeGlu metabolites, only rac-4APA was transported into synaptosomes, while 4OPA and 4HPA were not (FIG. 2B). We tested if 2MeGlu was in the neurotransmitter pool by subjecting preloaded synaptosomes to high potassium concentration-induced membrane depolarization. Both enantiomers of 2MeGlu were transported into synaptosomes during preloading; however, their potassium-induced release from vesicular storage was different (FIG. 2C). Synaptosomal concentration of the R enantiomer was not significantly altered by depolarization, whereas the S enantiomer was released upon depolarization in a manner very similar to endogenous Glu (FIG. 2E), as indicated by the relative difference of the substrate concentrations in the samples incubated under the low- and high-potassium conditions. When tested under identical conditions, rac-4APA exhibited high potassium concentration-dependent release (FIG. 2D) that was similar to endogenous GABA (FIG. 2E). Thus, (R)-2MeGlu and (S)-2MeGlu and rac-4APA were transported into synaptosomes, but only (S)-2MeGlu and at least one enantiomer of 4APA entered the neurotransmitter pool.

Initial metabolic assays also were performed in mouse cerebral synaptosomes, which are known to contain residual astrocytic components comprising <5% of total terminals by electron microscopic or flow cytometric detection (FIG. 9). Synaptosomal concentration of rac-2MeGlu decreased slowly over time with an estimated half life of 21 min, and was not associated with the concurrent appearance of 4APA or any other 2Me analogue within the GABA shunt, indicating that the 2Me analogues were not efficiently metabolized by this pathway's enzymes. We hypothesized that 2MeGlu might have been metabolized to 2MeGln and/or released back into the extrasynaptosomal space (FIG. 9). Indeed, rapid formation of 2MeGln along with a steady release of 2MeGlu were observed and accounted for the total concentration of all 2Me species over time, i.e., the total concentration of both 2MeGlu and 2MeGln did not change significantly over time (P=0.70, repeated measures one-way ANOVA, n=5) (FIG. 9), indicating that the only major metabolite of 2MeGlu in mouse synaptosomes was 2MeGln.

Figure 3C:
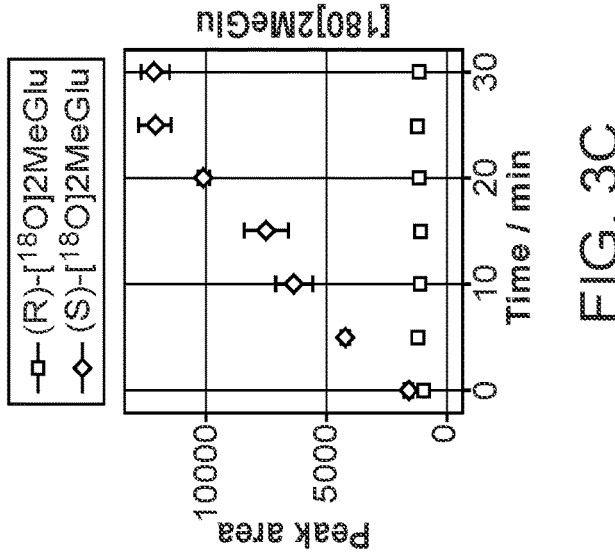
FIGS. 3A-3C. (A) Stereospecific conversion of 2MeGlu enantiomers by human glutamine synthetase. Reaction was performed with 10 mM substrate and 5 ng/mL enzyme in the presence of 10 mM ATP, 20 mM $MgCl_2$, 40 mM $NH_4Cl$, 25 mM 2-mercaptoethanol in 100 mM imidazole pH 7.0 buffer. (B) Conversion of rac-2MeGln by human glutaminase GLS1. Reaction was performed with 10 mM substrate and 5 ng/mL enzyme in phosphate pH 7.4 buffer. (C) Relative concentrations of (R)- and (S)-[$^{18}$O]2MeGlu generated in the GLS1 hydrolysis assay. Data are shown as mean±SEM, n=3.
Figure 3B:
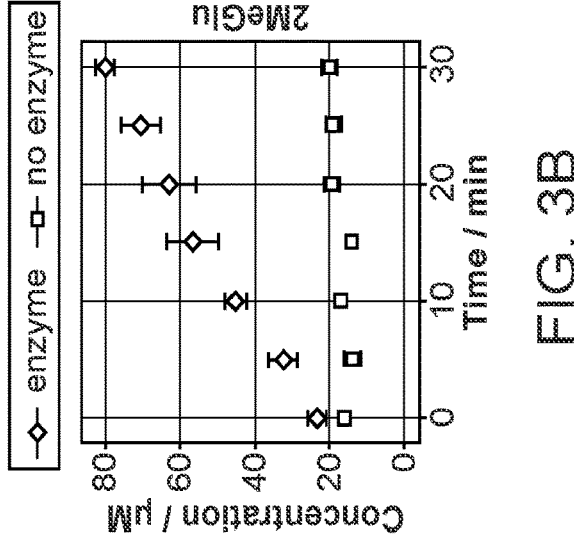
Figure 3A:
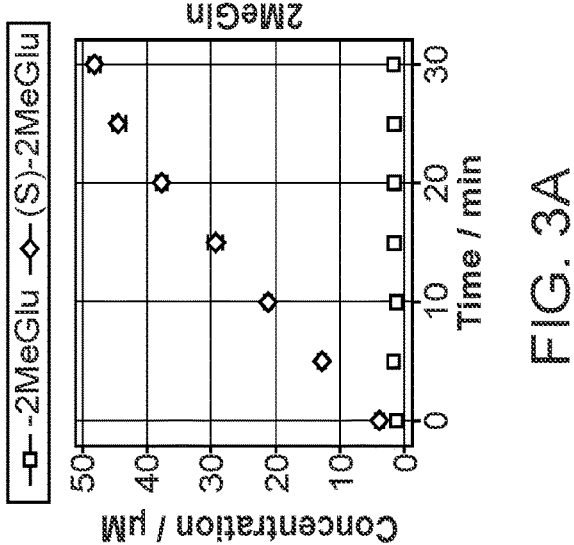

GS is responsible for brain metabolism of Glu to Gln. Consistent with the synaptosome results, 2MeGlu was converted by human GS to 2MeGln in the presence of ammonium ions and ATP, but the reaction was highly stereoselective towards the S enantiomer (FIG. 3A). This is another stereochemical difference with Glu, both enantiomers of which are amidated by GS. Our results are consistent with the previous work that showed the reaction of rac-2MeGlu with GS in the presence of ATP releases 50% of inorganic phosphate obtained under identical conditions with L-Glu. The reverse reaction was tested in vitro using human glutaminase GLS1, a phosphate-dependent amidohydrolase, which accounts for over 50% of glutaminase activity in the brain. In order to overcome the analytical interference caused by traces of 2MeGlu present in synthetic 2MeGln, catalytic hydrolysis was performed in $H_2O$-enriched buffer. Simultaneous detection of 2MeGlu and 2MeGlu-$^{18}O$ allowed us to distinguish between the newly formed 2MeGlu and any preexisting impurity, and thereby quantify exclusively the former (FIG. 3B). The appearance of 2MeGlu in the samples containing rac-2MeGln indicated that at least one enantiomer of 2MeGln is a substrate for human GLS1, albeit relatively slow; the apparent reaction rate was approximately 35-fold lower compared to that of Gln (65 µM/min vs 1.9 µM/min). Chiral analysis of the isotope-labeled hydrolysis products showed that the S enantiomer was the exclusive product of the GLS1-catalyzed reaction (FIG. 3C).

Figures 4A, 4B:
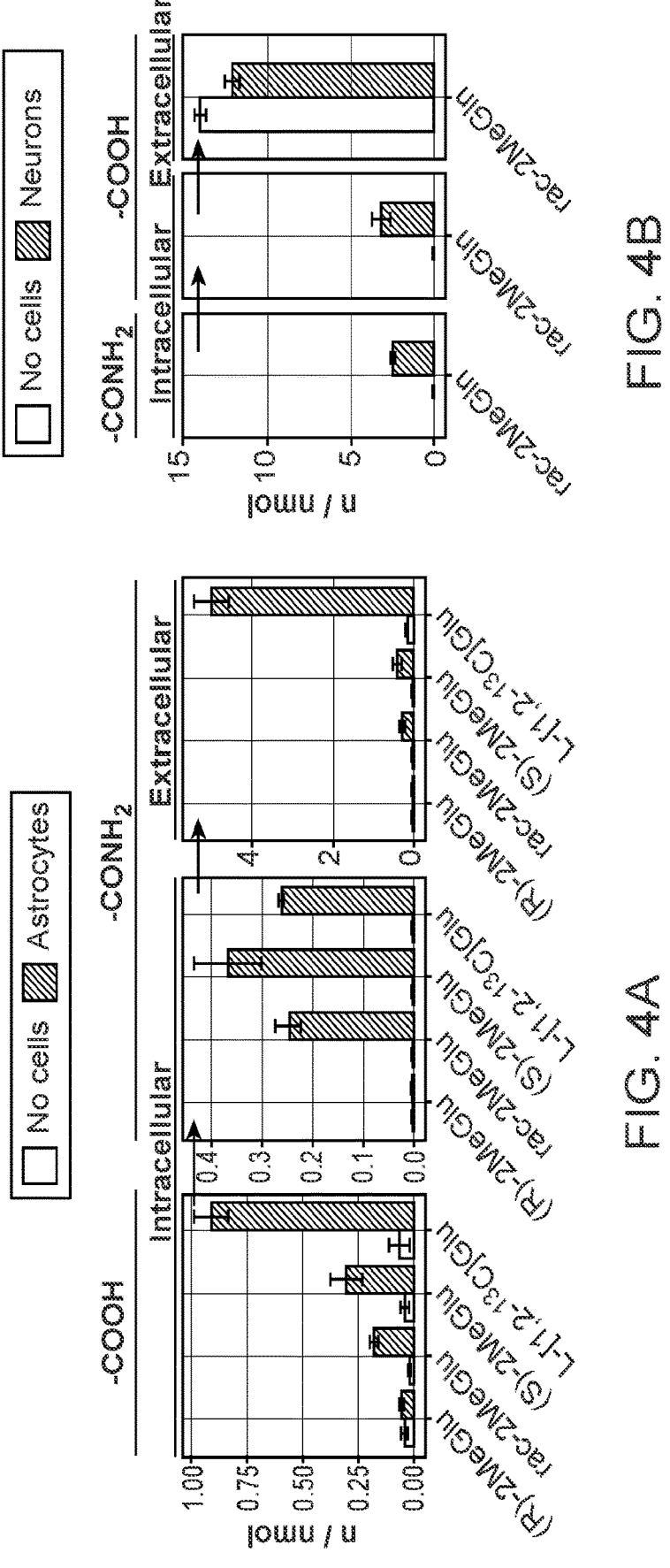
FIGS. 4A-4B Cell metabolism of 2MeGlu and 2MeGln. Data are shown as mean±SEM, n=3. Horizontal arrows represent an uptake-conversion-release cycle. (A) Astrocyte uptake, amidation, and release of 2MeGlu and its amide derivative, 2MeGln. Total intra- and extracellular amounts of 2MeGlu or [1,2-$^{13}$C]Glu (—COOH) and 2MeGln or [1,2-$^{13}$C]Gln (—CONH$_2$) were determined in cells and media. Primary astrocyte cultures were incubated in the presence of 1 mM of racemic or enantiopure 2MeGlu or L-Glu for 2 h at 37° C. along with cell-free controls. (B) Neuronal uptake, hydrolysis, and release of 2MeGln and its

Incubation of primary murine cerebral astrocytes with each enantiomer of 2MeGlu confirmed the stereoselective nature of 2MeGln formation observed in synaptosomes and with GS in vitro (FIG. 4). The S enantiomer was transported into astrocytes and then converted into 2MeGln. In contrast, the R enantiomer was not detected within astrocytes in significant amounts, and no conversion to 2MeGln was detected. Comparison with isotopically labeled L-[1,2-$^{13}$C] Glu, the endogenous substrate, revealed that the intracellular concentrations of 2MeGln and [1,2-$^{13}$C]Gln, made from (S)-2MeGlu and L-[1,2-$^{13}$C]Glu respectively, were similar (0.35 nmol/well vs 0.26 nmol/well); however, the extracellular concentrations were an order of magnitude different (0.4 nmol/well vs 5.0 nmol/well), suggesting that 2MeGln was released from astrocytes at a much lower rate compared to [1,2-$^{13}$C]Gln. Samples where racemic 2MeGlu was used as the substrate followed the pattern of the S enantiomer, although at concentrations consistently reduced 60-70%.

Enzymatic hydrolysis of 2MeGln back to 2MeGlu to complete the glutamate-glutamine cycle was tested in murine primary cerebral cortical neuron cultures (FIG. 4C). 2MeGlu was detected in the mouse neurons, although it was unclear whether it was a product of intracellular enzymatic hydrolysis of 2MeGln or direct transport from media, since traces of 2MeGlu were present in the 2MeGln synthetic product. The uptake of both enantiomers of 2MeGlu observed in synaptosomes and hydrolysis of at least one enantiomer of 2MeGln by human GLS1 suggested that both mechanisms contribute to the intracellular presence of 2MeGlu in neuron cultures. An identical experiment was performed in primary cerebral cortical neuron cultures with isotopically labeled L-[1,2-$^{13}$C]Gln for comparison. Intracellular [1,2-$^{13}$C]Gln was 2-fold lower than 2MeGln in corresponding samples, while [1,2-$^{13}$C]Glu was over 5-fold lower than 2MeGlu in cells. Together with the presence of extracellular [1,2-$^{13}$C]Glu, these results suggest that [1,2-$^{13}$C]Gln is enzymatically hydrolyzed and transported out of the cell at a higher rate than 2MeGln.

In summary, the above in vitro, synaptosome, and primary cell culture experiments show that 2MeGlu and 2MeGln are transported in and out of neurons and astrocytes, similar to their non-methylated endogenous analogues, while having more restricted, stereochemically-dependent, metabolic pathways. (S)-2MeGlu and (S)-2MeGln were shown to be substrates of GS and GLS1, respectively, while their R enantiomers were not. In addition, the relatively low rate of extracellular release of endogenously synthesized 2MeGln suggests partial trapping of the amidation product in primary astrocytes where it was generated.

Since GS is important to proliferation of some cancer cells, we determined the impact of both 2MeGlu enantiomers and rac-2MeGln on proliferation of glutamine-dependent MDA-MB-231 and SK-OV-3, and glutamine-independent MCF-7. Cell viability assays were conducted by BPS Bioscience and showed that none of the test compounds effectively inhibited cell proliferation (IC$_{50}$>100 µM) in any of the three cell lines (FIG. 10). These results aligned with our GLS1 inhibition assay, where none of the compounds displayed significant inhibitory activity (IC$_{50}$>1 mM) (FIG. 10).

We next examined pharmacokinetics of 2Me compounds in mouse blood and brain (FIG. 5). All compounds reached their maximum serum concentration within 15 minutes of intraperitoneal (IP) administration and were practically cleared from blood within 60 minutes (FIG. 5A). All tested compounds entered the brain where their kinetic profiles differed substantially (FIG. 5B). (R)-2MeGlu brain concentration peaked within 5 min at 30 pmol/mg protein and decreased over time with an estimated half life of approximately 70 min. (S)-2MeGlu reached its maximum brain concentration of 50 pmol/mg protein after 25 min, while being actively converted into its only known metabolite, 2MeGln, which concentration rose monotonically to over 250 pmol/mg protein at 120 min. Thus, (S)-2MeGlu and its metabolite (S)-2MeGln accumulated in the brain as much as 10-fold more than (R)-2MeGlu. Administered rac-2MeGln yielded peak brain concentration of 2MeGln more rapidly (25 min) than injection with (S)-2MeGlu, and then was relatively constant to 120 min. Interestingly, the concentrations of 2MeGln in mouse brain at the last time point (120 min) were almost identical whether administered (S)-2MeGlu or rac-2MeGln, indicating that (S)-2MeGlu is efficiently metabolized to 2MeGln in mouse brain and can act as a prodrug/precursor. A common feature observed for both (S)-2MeGlu and rac-2MeGln is the appearance of 2MeGlu at the 60 min and 120 min time points. Previously presented results from GLS1 enzymatic assay suggested that (S)-2MeGln undergoes slow enzymatic hydrolysis to (S)-2MeGlu. The pharmacokinetic experiment in mice aligns with that observation; the delayed appearance of 2MeGlu in the brain after the administered compounds have been cleared from blood indicates that 2MeGlu is slowly metabolized from the 2MeGln accumulated in brain, whether the original source was rac-2MeGln or (S)-2MeGlu. Finally, brain levels of endogenous Glu, Gln, or GABA also were determined as part of these experiments; two-way ANOVA showed that endogenous brain levels of Glu, GABA, or Gln were not significantly altered by either any of the three compounds administered at 100 mg/kg or the time after compound administration from 5 to 120 minutes.

We then explored the pharmacodynamics of enantiopure glutamate-mimicking compounds against a broad panel of glutamate and GABA receptors in both binding and functional assays (summarized in Table 1 and detailed in Tables 2-6). We deliberately assayed 2MeGlu enantiomers for activity against both glutamate and GABA receptors in case of receptor class switching as occurs with α-methyldopamine. Both compounds had weak to no significant activity against the large number of glutamate and GABA receptors screened. Interestingly, (S)-2MeGlu did not interact significantly with any of the tested receptors. (R)-2MeGlu exhibited weak antagonist behavior against GluN2A, one of four isoforms of the glutamate-binding subunit of N-methyl-0-aspartate (NMDA) receptors.

TABLE 1

| receptor name | receptor type | assay type | (R)-2MeGlu | (S)-2MeGlu |
|---|---|---|---|---|
| GluN2A | ionotropic | functional | ↓ | — |
| GluN2B | ionotropic | functional | — | — |
| GluN2C | ionotropic | functional | — | — |
| GluN2D | ionotropic | functional | — | — |
| GluA2 | ionotropic | functional | — | — |
| mGluR1 | metabotropic | binding | — | — |
| mGluR2 | metabotropic | binding | — | — |
| mGluR5 | metabotropic | binding | — | — |

TABLE 1-continued

| receptor name | receptor type | assay type | (R)-2MeGlu | (S)-2MeGlu |
|---|---|---|---|---|
| NMDA nonspecific | ionotropic | binding | — | — |
| AMPA nonspecific | ionotropic | binding | — | — |
| kainate nonspecific | ionotropic | binding | — | — |
| GABA$_A$ α1β1γ2 | ionotropic | functional | — | — |
| GABA$_A$ α1β2γ2 | ionotropic | functional | — | — |
| GABA$_A$ α1β3γ2 | ionotropic | functional | — | — |
| GABA$_A$ α2β1γ2 | ionotropic | functional | — | — |
| GABA$_A$ α2β2γ2 | ionotropic | functional | — | — |
| GABA$_A$ α2β3γ2 | ionotropic | functional | — | — |
| GABA$_A$ α3β1γ2 | ionotropic | functional | — | — |
| GABA$_A$ α3β2γ2 | ionotropic | functional | — | — |
| GABA$_A$ α3β3γ2 | ionotropic | functional | — | — |
| GABA$_A$ α4β1γ2 | ionotropic | functional | — | — |
| GABA$_A$ α4β2γ2 | ionotropic | functional | — | — |
| GABA$_A$ α4β3γ2 | ionotropic | functional | — | — |
| GABA$_A$ α4β3δ | ionotropic | functional | — | — |
| GABA$_A$ α5β1γ2 | ionotropic | functional | — | — |
| GABA$_A$ α5β2γ2 | ionotropic | functional | — | — |
| GABA$_A$ α5β3γ2 | ionotropic | functional | — | — |
| GABA$_A$ α6β1γ2 | ionotropic | functional | — | — |
| GABA$_A$ α6β2γ2 | ionotropic | functional | — | — |
| GABA$_A$ α6β3γ2 | ionotropic | functional | — | — |
| GABA$_B$ (B1/B2) | metabotropic | binding | — | — |
| GABA$_B$ (B1a/B2) | metabotropic | binding | — | — |
| GABA$_B$ (B1b/B2) | metabotropic | binding | — | — |
| GABA$_B$ (B1/B2) | metabotropic | functional | — | — |

Summary of glutamate and GABA receptor interaction assays. '↑' or '↓' arrows indicate agonist or antagonist activity, respectively. The number of arrows indicates IC50/EC50 in the range of 10-100 μM (one arrow), 1-10 μM (two arrows), or <1 μM (three arrows). Interactions with EC$_{50}$ or IC$_{50}$ above 100 μM are marked as "—"

Our data suggested that 2MeGlu was a false neurotransmitter that also interfered with the glutamate-glutamine cycle. Investigators at the Stanford Behavioral and Functional Neuroscience Laboratory (SBFNL), who were blinded to the identity of the compounds being tested, performed a broad-based screen of safety and tolerability followed by tests of learning and memory, similar to the behavioral screen of transgenic mice with glutaminase deficiency.

Figures 6A, 6B, 6C, 6D:
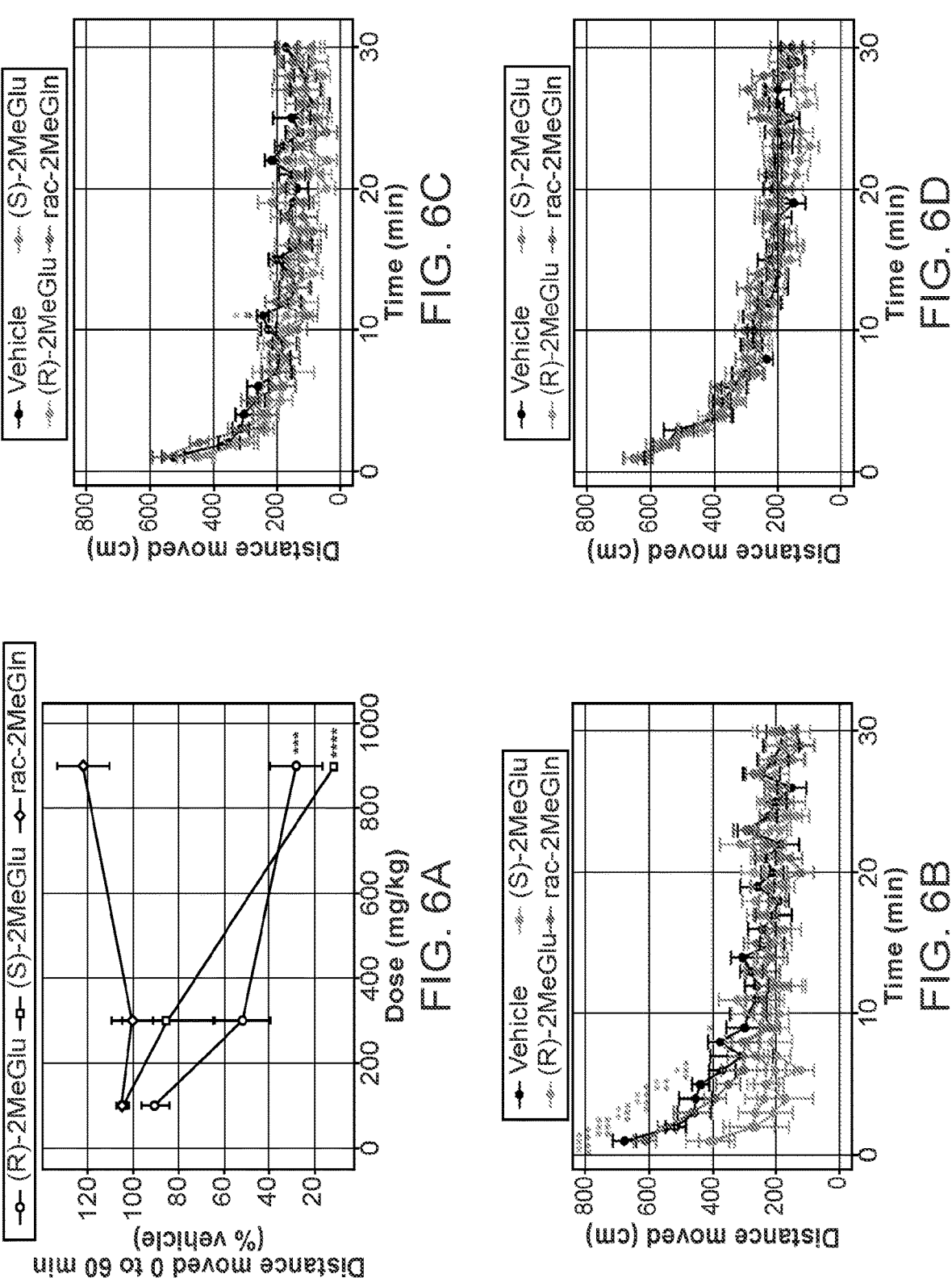

Male 2 month-old healthy mice were injected with a single dose (100, 300, or 900 mg/kg IP) of (R)-2MeGlu, (S)-2MeGlu, or rac-2MeGln and then immediately assessed by novel cage observation and for survival. Only one mouse died 10 days after 900 mg/kg of (R)-2MeGlu. Distance moved in the novel cage was significantly decreased for both (R)-2MeGlu and (S)-2MeGlu (P<0.001 for each, n=3) in a dose- and time-dependent manner, indicating marked reduction in response to novelty/locomotor activity while remaining alert and responsive (FIG. 6A and FIG. 11). Next, we performed a behavioral test battery called SHIRPA (measures 23 sensorimotor functions and well being), activity chamber open field assessment, and then withdrawal from hot plate using new groups of male 2 month-old mice following a single injection of 100 or 30 mg/kg IP of one of the three compounds or vehicle (n=6 per group). At the 100 mg/kg IP dose, there was no mortality, difference in latency to withdraw from hotplate, or difference on any SHIRPA score except locomotor activity for (R)-2MeGlu or (S)-2MeGlu. Distance moved in the activity chamber was significantly reduced for (R)-2MeGlu or (S)-2MeGlu compared to vehicle at all time points up to 6 minutes post injection with no significant difference in distance moved beyond 9 minutes; rac-2MeGln was not significantly different from vehicle at any time point (FIG. 6B). We repeated the acute exposure experiment in a separate set of mice now using 30 mg/kg or vehicle IP and observed modest but significant reduction in distance moved only at 11 minutes post injection with (R)-2MeGlu and rac-2MeGln (FIG. 6C); no significant differences on SHIRPA scores, or latency to withdraw from hot plate, were observed in the 30 mg/kg IP dose groups.

Subsequently, still-blinded experiments at SBFNL pursued behavioral impact of chronic low dose (S)-2MeGlu, (R)-2MeGlu, or rac-2MeGln in drug naïve, male, 2 month-old C57Bl/6 mice dosed with 10 mg/kg/day or vehicle IP for a month. Behavioral tests (n=10 mice per group) were performed starting one week after chronic dosing and followed well established protocols activity chamber and elevated plus maze (week 1 of testing), Y maze (week 2 of testing), Morris water maze (weeks 2 and 3 of testing), and fear conditioning (week 4 of testing). There was no mortality and no significant effect of treatment on body weight over the month, distance moved in the activity chamber (FIG. 60), time spent in the open arms in the elevated plus maze (FIG. 12), spontaneous alternation in the Y maze (FIG. 13), or learning in the Morris water maze (FIG. 14). In the fear conditioning paradigm, all treatment groups showed equivalent learning of the tone-shock association on Day 1 (FIG. 15). There was no significant effect of treatments compared to the vehicle treated group in contextual recall on Day 2 (FIG. 7A), indicating comparable hippocampal memory recall among experimental groups, consistent with the Morris water maze results. Finally, there were no significant differences detected in freezing during the cued recall or tone presentation on Day 3 between drugs and vehicle treated groups (FIG. 7B, FIG. 16).

Methylation of the alpha carbon of neurotransmitter precursors has been used with L-dihydroxyphenylalanine (L-DOPA) to create Aldomet or α-methyldopa, one of the first and still used antihypertensives, and with L-tryptophan to create a serotonergic PET imaging agent. Racemic 2MeGlu is generally synthesized from levulinic acid and has been used in enzymatic studies; as a potential effector of glutamate receptors, transporters, and brain tumor cell growth; in tissue slices as a potential effector of dopamine release, ammonia balance, calcium uptake, and metabotropic receptors; and in animals to moderate induced circling behavior. Enantiomers of 2MeGlu have been obtained by separation of racemate by a variety of methods, and (S)-2MeGlu or (R)-2MeGlu have been synthesized by a variety of approaches. (S)-2MeGlu has been tested as an inhibitor of EAAT1/2 transporters. Despite the use of rac-2MeGlu as a congener in these experiments, no one has investigated the metabolic impact of enantiomers of 2MeGlu or 2MeGln in brain, or explored their potential enantiomer-specific activity in animals. Here, we tested the hypothesis that enantiomers of 2MeGlu or 2MeGln selectively modulate metabolism in the GABA shunt or glutamate-glutamine cycle, and act as useful pharmacologic or imaging agents.

By design, 2-MeGlu was not a substrate for GAD or GLDH and therefore progressed neither through the GABA shunt nor underwent oxidative deamination. The S enantiomer (L isomer by the convention used for natural amino acids) was avidly transported into synaptosomes and stored and released like L-Glu. While substituting for L-Glu in the neurotransmitter pool, (S)-2MeGlu did not have significant activity across a broad spectrum of glutamate and GABA receptors. In aggregate, these data support classifying (S)-2MeGlu as a false neurotransmitter. We demonstrated that only (S)-2MeGlu is a substrate for GS and thereby can enter the glutamate-glutamine cycle; however, (S)-2MeGlu was not an efficient substrate for the reverse reaction. The net effect in vivo was that the false neurotransmitter, (S)-2MeGlu, rapidly accumulated as (S)-2MeGln in brain, which was then slowly converted back to (S)-2MeGlu.

Exposure to rac-2MeGln led to comparable but more rapid appearance of 2MeGln in brain, accompanied by slow generation of 2MeGlu over time. These properties lead us to propose that (S)-2MeGlu or 2MeGln have useful applications as pharmacologic agents that alter the excitatory/inhibitory balance in brain, and perhaps as imaging agents for GS expressing or Gln transporting cells.

(R)-2MeGlu, as expected, also was not a substrate for GAD and did not progress in the GABA shunt. (R)-2MeGlu, although transported into synaptosomes, did not enter the neurotransmitter pool, suggesting that (R)-2MeGlu is a substrate for neuronal membrane transport but not synaptic vesicle transport. (R)-2MeGlu did have some weak activity at the GluN2A subunit of NMDA receptors. (R)-2MeGlu also was transported into mouse brain, but much less efficiently than the S enantiomer. (R)-2MeGlu was not a substrate for GS and so did not enter the glutamate-glutamine cycle. The net effect was that (R)-2MeGlu accesses the brain and synaptic, but not vesicular, compartments where it is isolated from the usual metabolism of L-Glu, L-Gln, or GABA, and has some weak activity at glutamate receptors.

The enantiomer-specific biochemical and metabolic properties of 2MeGlu or 2MeGln demonstrate that they may have useful applications as molecular imaging agents for GS expressing or Gln transporting cells, and as pharmacologic agents that can alter excitatory/inhibitory balance. We therefore pursued safety and behavioral testing in young adult, healthy, male mice. Acute, high doses of (S)-2MeGlu, (R)-2MeGlu, or rac-2MeGln had minimal mortality, and (R)-2MeGlu or (S)-2MeGlu caused temporary, marked reduction in response to novelty/locomotor activity while remaining alert and responsive to ambient noise and gentle touch. This impressive, acute effect on mouse behavior observed at 100 mg/kg IP and higher doses may be due to temporary disturbance in glutamatergic neurotransmission from the inability of both enantiomers of 2MeGlu to be metabolized by GAD. The usefulness of such impaired response to novelty/locomotor activity has utility in the management of patients undergoing procedures or imaging sessions, and in the treatment of neurological and psychiatric disorders that derive in part from imbalance of excitatory and inhibitory neurotransmission.

Materials.

(R)-2-methylglutamic acid, (S)-2-methylglutamic acid and rac-2-methylglutamine were made to order by Concept Life Sciences (Cheshire, UK) from racemate. Buffer S (isotonic buffered sucrose solution): 0.32 M sucrose, 1 mM EDTA, 5 mM Tris-HCl pH 7.4. Buffer KRP (normal Krebs-Ringer phosphate buffer): 118.0 mM NaCl, 4.65 mM KCl, 1.23 mM $CaCl_2$, 1.18 mM $KH_2PO_4$, 3.54 mM $MgSO_4$, 15.64 mM $Na_2HPO_4$, 10 mM glucose. Buffer K-KRP (high-potassium Krebs-Ringer phosphate buffer): 84.3 mM NaCl, 40.5 mM KCl, 1.23 mM $CaCl_2$, 1.18 mM $KH_2PO_4$, 3.54 mM $MgSO_4$, 15.64 mM $Na_2HPO_4$, 10 mM glucose.

Synaptosome Preparation.

Mouse cerebral synaptosomes were prepared according to published methods. See Supplementary Methods for details. 500 μL aliquots of the synaptosome suspension were transferred to pre-chilled microcentrifuge tubes for experiments. Centrifugations were at 8,000 g for 4 min at 4° C., unless stated otherwise, and all samples were stored at −80° C.

Synaptosomal Neurotransmitter Uptake Assay.

To each tube, 5 μL of a test compound solution (final concentration 10 μM) in Buffer KRP or Buffer KRP alone were added. Samples were incubated at 4° C. or 37° C. for 1, 10, or 30 min and then immediately centrifuged and washed twice by resuspension-centrifugation with Buffer S (0.5 mL). Resulting pellets were resuspended in 170 μL of 0.1% aqueous formic acid and mixed with 330 μL of ACN.

Potassium-induced Neurotransmitter Release Assay.

To each tube, 2.5 μL of a test compound solution (final concentration 100 μM) in Buffer KRP or Buffer KRP alone were added. Samples were incubated for 15 min at 37° C., briefly chilled on ice, and then immediately centrifuged and washed twice with Buffer KRP. The resulting pellets were then resuspended in either Buffer KRP (500 μL) or Buffer K-KRP (500 μL). Samples were immediately centrifuged or incubated for 5, 10 or 15 min at 37° C., then centrifuged and washed with Buffer KRP. Resulting pellets were resuspended in 400 μL of 60% ACN containing 2.5 μM Glu-d5 and 2.5 μM Gln-d5 as internal standards.

Metabolism in the GABA Shunt Pathway in Synaptosomes

To each tube, a 5 μL aliquot of a test compound solution (final concentration 100 μM) in Buffer KRP or Buffer KRP alone were added. The samples were incubated for 15 min at 37° C., briefly chilled on ice, and then immediately centrifuged and washed twice by resuspension-centrifugation with Buffer S (0.5 mL). The pellets were then resuspended in Buffer KRP (500 μL). Samples were then immediately centrifuged or incubated for 5, 10, 15, 20, 25 or 30 min at 37° C. and then centrifuged and washed by resuspension-centrifugation with Buffer S (0.5 mL). Resulting pellets were resuspended in 170 μL of 0.1% aqueous formic acid, mixed with 330 μL of ACN.

Metabolism in the Glutamate-Glutamine Cycle in Synaptosomes

To each tube, 5 μL of 2MeGlu solution (final concentration 100 μM) in Buffer KRP or Buffer KRP alone were added. The samples were incubated for 15 min at 37° C., briefly chilled on ice, and then immediately centrifuged and washed twice by resuspension-centrifugation with Buffer S (0.5 mL). The pellets were then resuspended in Buffer KRP (200 μL). Samples were then kept on ice or incubated for 10, 20, 30, 40 or 50 min at 37° C. and then chilled on ice. Then all samples were centrifuged, 200 μL of supernatants were collected, and the pellets were suspended in 200 μL of 80% ACN. Supernatants and pellet suspensions were diluted with 250 μL of ACN and 50 μL of 10 μM d5-Glu in water as internal standard.

Catalysis of 2MeGlu C5-Amidation by Human Glutamine Synthetase.

The procedure was adapted from an existing protocol. To a reaction mixture in a 1.5 mL microcentrifuge tube containing 10 mM substrate, 10 mM ATP, 20 mM $MgCl_2$, 40 mM $NH_4Cl$, 25 mM 2-mercaptoethanol in 100 mM imidazole-HCl buffer pH 7.0, recombinant human glutamine synthetase (final concentration: 5 ng/mL) was added. The tubes were incubated in a preheated thermomixer at 37° C. and shaken at 600 rpm (30 s on, 30 s off). 5 μL aliquots were collected in triplicate every 5 min and immediately diluted with 195 μL of cold 60% ACN containing 10 μM Glu-d5 and Gln-d5 as internal standards in a 96 well plate. After collecting all samples, 200 μL of ACN was added to all wells and the plate was shaken at 1000 rpm for 5 min at room temperature, and then stored at −80° C. until analysis.

Catalysis of 2MeGln Hydrolysis by GLS1 Glutaminase.

The procedure was adapted from an existing protocol. To a reaction mixture in a 1.5 mL microcentrifuge tube containing 10 mM rac-2MeGln or L-Gln-[13]C2 in 100 mM phosphate pH 7.4 buffer made in 20% atom $^{18}$O water, recombinant GLS1 (final concentration: 5 ng/mL) was added. The tubes were incubated in a preheated thermomixer at 37° C. and periodically shaken at 600 rpm (30 s on, 30 s off). 5 μL aliquots were collected in triplicate every 5 min and immediately diluted with 195 μL of cold 60% ACN containing 10 μM Glu-d5 and Gln-d5 as internal standards in a 96 well plate. After collecting all samples, the plate was shaken at 1000 rpm for 5 min at room temperature, and then stored at −80° C. Before analysis the plate was thawed and 10 μL aliquots of the extracted reaction mixtures were diluted with 190 μL of 90% acetonitrile.

The quantification of the newly formed 2MeGlu in the presence of the preexisting trace amounts was performed in the following way. Peak area ratio of Glu-$^{13}$C2 to Glu-$^{13}$C2$^{18}$O was calculated in all samples containing Glu-$^{13}$C2. The mean ratio value was then applied to calculate the hypothetical peak area of the newly formed 2MeGlu based on the directly measured 2MeGlu-$^{18}$O peak area. The ratio of the newly formed 2MeGlu peak area and the total 2MeGlu peak area was applied to calculate the concentration of the newly formed 2MeGlu from the total 2MeGlu concentration determined directly using the calibration curve.

Astrocyte Transport and Metabolism of 2MeGlu.

Primary astrocytes from C57Bl/6 mouse brain were cultured in complete astrocyte growth medium at 37° C. at 5% $CO_2$ on 96 well plates. Cells were exposed to 1 mM compound in 100 μL medium for 2 h at 37° C. Supernatants were collected, centrifuged at 2,500 g for 10 min at 4° C. 10 μL aliquots were diluted with 190 μL 60% ACN containing 10 μM Glu-d5 and Gln-d5. Cells were quickly washed with 250 μL cold PBS twice and suspended in 200 μL of 60% ACN containing 10 μM Glu-d5 and Gln-d5. All samples were shaken at 1,000 rpm for 5 min and then stored at −80° C.

Neuronal Transport and Metabolism of 2MeGln.

The procedure was adapted from an existing protocol. Wild-type (WT) C57BL/6J mating pairs were housed according to Stanford IACUC protocol. On day P0, pups were euthanized and brains dissected in cold HBSS (without $Ca^{2+}$ or $Mg^{2+}$). The forebrain was microdissected to isolate the cortex and hippocampus. These brain regions were minced in cold HBSS before trypsinization at 37° C. for 9 minutes, followed by trituration, through 2 glass polished Pasteur pipettes. The resulting cell suspension was passed through a 100 μm filter to isolate single cells which were sedimented at 250 g for 5 minutes. The cell pellet was then resuspended in complete Neural Basal Media (Neural Basal Media+Glutamax+B-27 Plus Supplement+Pen/Strep)+10% FBS, counted using a hemocytometer and plated at 1×10$^6$ cells per mL into a 24 well plate (1 mL per well) coated with poly-D-lysine and laminin. Cultures were grown at 37° C./5% $CO_2$ in a tissue culture incubator. Media was exchanged 50% on day 1 in vitro (1 DIV) with fresh complete Neural Basal Media without FBS and thereafter every other day with the same media. On 3 DIV the media was spiked with 2 μM AraC to limit glial growth. On 10 DIV the media was completely replaced with 500 μL Neural Basal Media containing B-27 Plus Supplement+Pen/Strep without added Glutamax but instead containing 1 mM substrate at 37° C. for 2 h. The supernatants were collected, centrifuged at 16,000 g for 5 min at 4° C. 10 μL aliquots were diluted with 190 μL 60% ACN containing 5 μM Glu-d5 and Gln-d5. The cells were washed with 500 μL PBS twice and suspended in 200 μL of 60% ACN containing 5 μM Glu-d5 and Gln-d5. All samples were shaken at 800 rpm for 5 min and then stored at −80° C. until analysis.

In Vivo Animal Studies.

Behavioral tests were performed on 2 month-old, male, C57Bl/6 mice. We selected male mice because SBFNL historical controls are male mice. First, we assessed safety and tolerability of acute exposure to our novel chemicals through the following sequence of tests immediately following IP injection: maximum tolerated dose with novel cage observation at 100, 300, or 900 mg/kg, and then SHIRPA, activity chamber, and then hot plate latency using 100 or 30 mg/kg IP in different drug naïve mice. Second, we investigated the impact of chronic exposure to 10 mg/kg (3-times lower dose than that with minimal acute impact on locomotor activity) daily IP injection starting one week prior to assessment of locomotion in the activity chamber and elevated plus maze (week 1), or learning and memory with Y maze (week 2), Morris water maze (weeks 2 and 3), and then fear conditioning (week 4) according to established protocols, including not counterbalancing the escape platform location. Animals were dosed daily from 3 to 5 PM after the conclusion of each behavioral testing session. While the time from first dose for each behavioral test is different, our experimental protocol allows for efficient testing of chronic effects of novel compounds.

Materials.

rac-2-Methylglutamic acid (cat. no. M0229), and 4-oxo-pentanoic acid (cat. no. L0042) were obtained from TCI America. rac-4-Hydroxypentanoic acid (as sodium salt, cat. no. EN300-176456) and rac-4-aminopentanoic acid (as hydrochloride, cat. no. EN300-81918), were obtained from Enamine. LC-MS-grade acetonitrile (cat. no. A955), formic acid (cat. no. A117) and trifluoroacetic acid (cat. no. A116) were obtained from Fisher Scientific. Isotopically labeled L-glutamic acid (2,3,3,4,4-d5, cat. no. DLM-556; 1,2-13C2, cat. no. CLM-2024) and L-glutamine (2,3,3,4,4-d5, cat. no. DLM-1826; 1,2-13C2, cat. no. CLM-2001) were purchased from Cambridge Isotope Laboratories. HPLC-grade ammonium formate (cat. no. 60-020-36) was obtained from Fluka.

C57Bl/6 mouse brain primary astrocytes were purchased from Lonza, Basel, Switzerland (cat. no. M-ASM-330). Astrocytes were cultured in medium (cat. no. CC-3187) and supplemented with growth factors (cat. No CC-4123) to make a complete astrocyte growth medium. The second passage of astrocytes cultured in complete astrocyte growth medium at 37° C. and 5% $CO_2$ was used for experiments. Recombinant human GLS1 (cat. no. SRP0516) was purchased from Sigma. Recombinant human GS (cat. no. ab222354) was purchased from Abcam.

Chemical Characterization of Key Compounds.

(R)-2MeGlu: $^1$H NMR ($D_2O$, 500 MHz): δ 2.48 (m, 2H), 2.13 (m, 2H), 1.52 (s, 3H). $^{13}$C{$^1$H} NMR ($D_2O$, 126 MHz): δ 177.1, 175.7, 60.7, 31.9, 29.0, 22.1. >99% pure (UPLC-ELSD), 95% e.e. (chiral LC-MS) (S)-2MeGlu: $^1$H NMR ($D_2O$, 500 MHz): δ 2.49 (m, 2H), 2.15 (m, 2H), 1.53 (s, 3H). $^{13}$C{$^1$H} NMR ($D_2O$, 126 MHz): δ 176.9, 175.5, 60.6, 31.8, 28.9, 22.0. >99% pure (UPLC-ELSD), 95% e.e. (chiral LC-MS) rac-2MeGln: $^1$H NMR ($D_2O$, 500 MHz): δ 2.38 (m, 2H), 2.10 (m, 2H), 1.52 (s, 3H). $^{13}$C{$^1$H} NMR ($D_2O$, 126 MHz): δ 177.7, 176.0, 60.9, 32.7, 29.9, 22.2. >97% pure (UPLC-ELSD).

Protein Concentration Determination.

500 μL of the synaptosome preparation was centrifuged (8,000 g for 4 min at 4° C.) and the supernatant was discarded. The pellet was suspended in 200 μL of RIPA buffer and incubated in ice for 90 min. The suspension was then sedimented (14,000 g for 10 min at 4° C.) and the supernatant used to determine the total protein concentration using Pierce BCA Protein Assay Kit and Biotek Epoch microplate spectrophotometer by measuring absorbance at 562 nm.

LC-MS/MS analysis, HILIC conditions.

LC-MS/MS HILIC analysis was performed using Agilent 6470 Triple Quadrupole LC/MS System with Agilent 1290

Infinity II LC module. Prior to analysis all samples were filtered through a Multiscreen Solvinert 0.45 μm PTFE filter plate to a polypropylene 0.5 mL 96-well plate. 2.5 μL of the sample was injected onto an Acquity UPLC BEH Amide column (2.1×50 mm, 1.7 μm particle size, Waters, part no. 186004800) equipped with an Acquity UPLC In-Line Filter (Waters, part no. 205000343), thermostatted at 40° C. The sample was eluted at a flow rate of 0.6 mL min$^{-1}$ with one of three gradient methods. Method 1 was developed for rapid quantification of all investigated compounds in relatively diluted biological matrices (synaptosome extract, cell extracts, in vitro reaction supernatants), and used lower-pH buffer A (5 mM ammonium formate in water containing 0.1% formic acid, pH 3.2) and buffer B (5 mM ammonium formate in 95:5 (v/v) acetonitrile-water containing 0.1% formic acid) with the following gradient: 0.0-2.5 min: linear gradient from 10% to 27.5% A; 2.51-3.0 min: hold 45% A; 3.01-3.5 min: hold at 10% A. Method 2 was a modified version of Method 1 for accurate quantification of small amounts of 2MeGlu in brain tissue homogenate, where two isomeric analytes were found to partially overlap with the peak of interest and interfere with quantification. It used the same buffer system and a longer gradient method: 0.0-5.0 min: linear gradient from 0% to 32.5% A; 5.01-6.0 min: hold 0% A. The mass spectrometer was operated in multiple reaction monitoring (MRM) positive mode with capillary voltage set to 3.5 kV, nebulizing gas held at 250° C., and superheated sheat gas held at 300° C. In experiments where isotopically labeled internal standard was added, results were corrected accordingly.

LC-MS/MS Analysis, Chiral Conditions.

LC-MS/MS chiral analysis was performed using Agilent 6470 Triple Quadrupole LC/MS System with Agilent 1290 Infinity II LC module. Prior to analysis all samples were filtered through a Multiscreen Solvinert 0.45 μm PTFE filter plate to a polypropylene 0.5 mL 96-well plate. 1.0 μL of sample was injected onto an CROWNPAK CR-I(+) column (3.0×150 mm, 5 μm particle size, Daicel, part no. 53784) equipped with an Acquity UPLC In-Line Filter (Waters, part no. 205000343), thermostatted at 20° C. The sample was eluted isocratically at a flow rate of 0.4 mL min$^{-1}$ with buffer C (96:4 ACN/water v/v, 0.1% TFA; parameters varied in the optimization experiments). The mass spectrometer was operated in multiple reaction monitoring (MRM) positive mode with capillary voltage set to 3.5 kV, nebulizing gas held at 250° C., and superheated sheat gas held at 300° C.

Synaptosome Preparation.

Cerebral hemispheres from a C57BL/6 mouse were homogenized in 3 mL of Buffer S using pre-chilled 5 mL Potter-ELV tissue grinder (800 rpm, 8 strokes). The crude homogenate was diluted with Buffer S to the total volume of 4 mL and centrifuged at 1,000 g for 10 min at 4° C. The supernatant was collected and sedimented (10,000 g for 20 min at 4° C.). The supernatant was discarded and the pellet washed by resuspension-centrifugation (8,000 g for 4 min at 4° C.) with Buffer S (4 mL, ×1) and Buffer KRP (2 mL, ×3). The resulting pellet was resuspended in 3 mL of Buffer KRP and filtered on Ultrafree-CL 5 μm PVDF centrifugal device (1,000 g for 4 min at 4° C.). The filtrate was diluted to 15 mL with ice cold Buffer KRP and kept on ice. The synaptosome preparation was used immediately in the following experiments.

Synaptosomal Neurotransmitter Uptake Assay.

96-well plate experiments: 250 μL aliquots of the synaptosome suspension were transferred to two 0.8-mL 96 well plates, one on ice (0° C. samples only) and one in a thermoblock (37° C. samples only), and equilibrated for 10 min. 5 μL of a test compound (0.5 mM; final concentration: 10 μM) in Buffer KRP or Buffer KRP blank were added 10, 20 or 30 min before the incubation termination. "0 min" samples were prepared by placing the test compound solution in a separate pre-chilled V-shape bottom 2-mL 96 well plate; at the end of incubation 200 μL aliquots of all samples were transferred to the 2-mL 96 well plate and centrifuged (2,500 g for 15 min at 4° C.) immediately. The resulting pellets were rinsed with Buffer KRP, followed by centrifugation, twice, then resuspended in 200 μL of 60% ACN containing 2.5 μM Glu-d5 as internal standard and stored at −80° C. until analysis.

Pharmacokinetics on 2MeGlu and 2MeGln in Mice.

C57BL/6 mice (Jackson Laboratory cat. no. 000664) were administered 100 mg/kg IP. At the times indicated, mice were deeply anesthetized by isoflurane, blood was collected by cardiac puncture and left to clot on ice, and then animals were perfused with cold PBS until viscera turned pale and blood ceased flowing from the inferior vena cava. Whole brain was promptly dissected and one half frozen at −80° C. until homogenization in ice cold PBS (pH 7.4) using a probe ultrasonic homogenizer (Branson Sonifier 450, Power: 5, Cycle: 30%, time: 10 s) on ice. The lysate was centrifuged (2,500 g for 15 min at 4° C.) and the supernatant was assayed using Pierce BCA Protein Assay Kit (23225) using BioTek Epoch plate spectrophotometer by recording absorbance at 562 nm. Two or three 10 μL aliquots of the homogenate were transferred to a 96 well plate and extracted with 190 μL of 60% acetonitrile in water containing 10 μM GABA-d6 or 10 μM Glu-d5 and Gln-d5 as internal standards. 40 μL aliquots of the extracts were then diluted with 120 μL of acetonitrile and prepared for LC-MS/MS analysis. Brain and serum half-lives were calculated using the 'PKNCA' package for R. Endogenous levels of Glu, Gln and GABA were determined in the brains of mice used in the pharmacokinetics experiment. MRM transitions specific for Glu, Gln and GABA were monitored simultaneously.

Invivo Animalstudies; MaximumToleratedDose(MTD) and Behavioralstudies.

Animals: Two month-old, naïve male C57Bl/6 mice from Jackson Laboratory (Stock ID #000664) were group-housed in a Stanford University animal facility with 12:12 hour light/dark cycle (8:30 am light off 8:30 am light on) and had free access to water and food. All behavioral tests were conducted during the animal dark-cycle. All procedures followed the National Institute of Health guidelines and were approved by the Institutional Administrative Panel on Laboratory Animal Care (APLAC).

Dosing: (R)-2MeGlu (30, 100, 300, or 900 mg/kg), (S)-2MeGlu (30, 100, 300, or 900 mg/kg), rac-2MeGln (30, 100, 300, or 900 mg/kg) and vehicle (PBS) were administered at 10 ml/kg IP dosing volume. Three mice were dosed once with the assigned drug (100, 300, or 900 mg/kg) or vehicle and immediately placed in a new cage for novel cage observation. Subsequently, six mice were dosed once with the assigned drug (30 or 100 mg/kg) or vehicle and tested by SHIRPA, activity chamber, and then hot plate tests.

Novel Cage Observation:

The mouse was dosed and immediately placed in the center of a clean, Innovive disposable rat cage with bedding (dimensions: 17"L×13.4"W×7.8"H) and allowed to move freely while being tracked automatically. Mice were monitored with Ethovision XT tracking software for the distance moved and average velocity during the 60-minute trial. They were returned to their home cage after the test. A new cage was used for each mouse.

Hot Plate Test:

Hot Plate apparatus (IITC Inc. Model 39) was set to 55° C.±0.2. On testing day, mice were placed on the surface of the hot plate and covered by a transparent glass cylinder (25 cm high and 12 cm diameter). A 30 second cutoff time was assigned. A remote foot-switch pad was used to control the start/stop/reset function. Latency time was recorded when hind paw licking or jumping off first occurred.

SHIRPA:

The SHIRPA preliminary screen designed by Rogers et al. (1997) was modified and used to assess the general health and behavioral traits of the mice for the initial five minutes after drug administration. The test was conducted in three different testing locations: A cylindrical clear plastic viewing jar (15 cm height×10 cm diameter), a polycarbonate cage (Arena) with 10 cm×10 cm squares on the floor, and a 1 cm×1 cm wire grid. The test began by placing the mouse in the clear plastic viewing jar for 60 seconds, and the behavioral parameters were monitored and recorded. The mouse was then transferred to an open-top arena by releasing them from 25 cm above the floor of the arena. Upon completion of monitoring the parameters inside the arena, the mouse was removed from the arena by the tail. Behavioral parameters monitored were according to Portmann et al. (2014).

Activity Chamber Open Field:

Assessment was made in an Open Field Activity Arena (Med Associates Inc., St. Albans, VT. Model ENV-515) mounted with three planes of infrared detectors within a specially designed sound-attenuating chamber (Med Associates Inc., St. Albans, VT. MED-017M-027). The arena was 43 cm (L)×43 cm (W)×30 cm (H) and the sound-attenuating chamber was 74 cm (L)×60 cm (W)×60 cm (H). The mice were placed in the corner of the testing arena and allowed to explore the arena for 60 min while being tracked automatically. Parameters measured include distance moved, velocity, rearing, and times spent in the periphery and center of the Arena. Periphery was defined as the zone 5 cm away from the arena wall. The Arena was cleaned with a 1% Virkon solution at the end of the trial. The novel cage observation (vide supra) and activity chamber open field assessment are not performed in a similar manner in our laboratory, and do not represent the same behavioral outcome. The novel cage protocol is conducted on the benchtop in a lighted room using a clean home cage, and tests habituation using video recording and scoring of behavioral performance. Moreover, the novel cage allows the tester to visualize any other side effects such as seizure or repetitive jumping. The activity chamber is in an enclosed box, and the test is done in the dark, without bedding, and in a sound isolating chamber. The activity chamber measures distance moved using infrared beams and without video recordings.

In Vivo Animal Studies; Chronic Efficacy Study Using C57Bl/6J Mice

Animal: Two month-old, naïve male C57Bl/6 mice from Jackson Laboratory (Stock ID #000664) were used in the study. The animals were housed as described above.

Dosing: (R)-2MeGlu (10 mg/kg), (S)-2MeGlu (10 mg/kg), rac-2MeGln (10 mg/kg), and vehicle (PBS) were administered IP at 10 ml/kg dosing volume daily. The first dose was administered one week prior to behavioral tests and continued for four weeks during the behavioral testing.

Activity Chamber Open Field: The assessment took place in an Open Field Activity Arena as described above for 30 min. The Arena was cleaned with a 1% Virkon solution at the end of the trial. Activity chamber open field assessment was conducted after one week of exposure to compounds or vehicle.

Elevated Plus Maze: The maze was made of acrylonitrile butadiene styrene (ABS) plastic and had two open arms and two close arms that were 30 cm long and 5 cm wide. The center area where the open and close arms meet was 5 cm×5 cm. The open arms had 2 mm lips at the edges, and the closed arms had 15 cm opaque walls. The maze was elevated 50 cm and surrounded by privacy blinds during the test. The maze was illuminated to 7 lux using red light throughout the test. Each mouse was released in the center of the maze and given 5 min to explore the maze. Duration and frequency in each zone of the maze were recorded using Ethovision (Noldus Information Technology, Wageningen, the Netherlands) tracking software. The maze was cleaned with a 1% Virkon solution at the end of the trial. Elevated plus maze was conducted after one week of exposure to compounds or vehicle.

Y Maze Spontaneous Alternation: The Y maze is made of plastic with 3 arms in a "Y" shape. The arms are labelled as Arm A, B, and C; Arm A is 20.32 cm (L)×5 cm (W) 12.7 cm (H), Arm B and C are 15.24 cm (L)×5 cm (W), and 12.7 cm (H). The test is based on the willingness of rodents to explore a novel environment and designed to measure spontaneous alternations in rodents. Each mouse was placed in the center of the maze facing Arm B. The first entry was excluded from data analysis because the animals were led to the initial arm entry by the experimenter. Using an overhead camera, the number of arm entries and alternations were recorded for 5 minutes. An arm entry is when all four paws enter into a new arm of the maze. The apparatus was cleaned with 1% Virkon. Parameters recorded were % alternation and the total number of entries into arms. The Y maze test was conducted after two weeks of exposure to compounds or vehicle.

Morris Water Maze: During the Hidden Platform Training (HPT), mice were given 2 trials, with 1-minute inter-trial-intervals (ITIs) in a circular water tank (172 cm diameter) filled with opaque water at 22.0±1.5° C. Nontoxic tempera paint was used to make the water opaque. A circular platform (17 cm diameter) was submerged 1 cm below the water's surface and placed in one of the four quadrants of the pool (Quadrant 2). The release locations into the pool were randomly chosen to prevent spatial bias and the platform was also relocated during reversal training. We conducted 3 days of training with 2 trials each day for a total of the 6 trials prior to probe 1 (Days 1 to 3). Specifically, mice were given a maximum of 60 s to find the submerged platform per trial. The experimenter guided the mice to the platform if they failed to find it within the 60 s. After remaining on the platform for 15 s, mice were removed from the platform and placed in a dry cage with a paper towel. This process was repeated for 3 days. On the following day (~24 hours after the last training trial), the platform was removed from the pool, and a 60 s probe trial was conducted. After acquiring the data for the probe trial, the platform was replaced at the same location, and the mice were given additional two trials of training. Three days (~72 hours) after the last training trial, a second probe trial was conducted. The platform was relocated to a new quadrant (Quadrant 4) after the second probe trial, and the animals were trained in Reversal Hidden Platform Training (RHPT). The procedures for RHPT were identical to HPT and were conducted for 3 days (Days 7 to 9). A third probe trial was conducted on the following day (~24 hr). The platform was relocated to Quadrant 1 upon completion of the third probe trial. A ping pong ball was erected from the submerged platform and the mice were given two trials of Visible Platform Training to ensure they lacked gross sensorimotor deficit and visual impairment.

The escape latency, distance moved, duration in zones, and velocity of the animals were recorded using Ethovision XT (Noldus Information Technology, Wageningen, Netherlands). The Morris water maze test was conducted during two to three weeks of exposure to compounds or vehicle.

Fear Conditioning: Coulbourn Instruments (Holliston, MA, USA) fear conditioning system and FreezeFrame software were used for analysis. The experiment consisted of 1 day of training, 1 day of contextual testing, and 1 day of cued testing. The training and contextual testing chambers were identical with similar context. The walls were made of aluminum. The floor was a gray metal grid through which the US was delivered, and the chambers used yellow color house light and were scented with mint extract to produce a unique smell in the chambers. The chambers were cleaned with a 10% simple green solution (Sunshine Makers, Inc.) between each mouse. The cued testing chambers were circular-shaped, made of plastic, used blue color house light, and were scented with vanilla extract to create a unique context different from training and contextual testing. This chamber was cleaned with 70% ethanol between each mouse. Both chambers were mounted within specially designed sound-attenuating chambers. Each chamber had speakers mounted on the wall and included an exhaust fan and camera. On Day 1 training, mice were placed individually into a training chamber for 200 seconds. A tone (20 seconds, 80 dB, 2 kHz) was presented to the mouse, followed by an electrical shock (intensity 0.5 mA, 2 seconds) 18 seconds after the end of the tone (Misane et al. 2005, Burman 2014, Lugo et al. 2014). This procedure was repeated two times with a 60 second interval from the end of the shock to the next tone. The mouse was removed from the chamber and returned to the home cage 60 seconds after the last shock. On Day 2, the mice were placed back into the training chamber without any tone or shock for contextual memory testing for 15 minutes. On Day 3, the mice were placed into the cued testing chamber with just tones (20 seconds, 80 dB, 2 kHz) presented 3 times with 80 second intervals after 200 seconds of habituation. Overall, the mice received the tone and shock pairings only on the training day. An overhead camera was used to record mice freezing behavior. The fear conditioning test was conducted after four weeks of exposure to compounds or vehicle.

We have shown when studying the cognitive enhancement in normal, young control mice, overtraining of the animals will lead to saturation of behavioral learning, making it very difficult to display pharmacological improvements in behavioral paradigms. We therefore chose less training trials per day and less number of training days in the Morris water maze to increase the likelihood of observing drug effects. Likewise, the fear conditioning task, we chose lower shock intensity and lower number of tone and shock (2×) pairings to create a greater opportunity to observe pharmacologic activity.

Receptor functional & binding assays.

Functional assays of all $GABA_A$, NMDA (GluN2A-GluN2D) and AMPA (GluA2) receptor subunits were performed by SB Drug Discovery as a part of their CNS discovery panel using FLIPR technology. Briefly, receptor-expressing HEK 293 cell lines were incubated in a red membrane potential dye in HEPES:HBSS pH 7.4 buffer and the fluorescence ($\lambda_{ex}$: 488, $\lambda_{ex}$: 510-570) was monitored over time as the test compounds and/or reference compounds were added to the solution. In agonist assay, only test compounds were added. In positive allosteric modulator assay, cells were preincubated with test compounds and then low concentration (approximately $EC_{20}$) of an appropriate agonist was added. In antagonist assay, cells were preincubated with test compounds and then high concentration (approximately $EC_{80}$) of an appropriate agonist was added. For $GABA_A$ assays, GABA was used as the agonist, picrotoxin was used as the reference antagonist and allopregnanolone was used as the reference positive allosteric modulator (PAM). For NMDA assays, a mixture of glutamate, glycine and $CaCl_2$ was used as the agonist, MK801 was the reference antagonist and pregnenolone sulfate or GNE 9278 were used as reference PAMs. For AMPA assays, glutamate was used as the agonist, CNQX was the reference antagonist and cyclothiazide was used as the reference PAM. All compounds were tested at 7 concentration points in triplicate and EC50/IC50 was determined where applicable. Functional $GABA_B$ assay was performed by Eurofins Discovery (Cerep) using $Ca^{2+}$-dependent fluorimetry in RBL cells expressing human $GABA_B$ (B1/B2) receptor. All compounds were tested at a single concentration of 100 uM in triplicate.

Nonspecific AMPA, kainate and NMDA binding assays were performed by Eurofins Discovery (Cerep) using rat cerebral cortex membranes and radiolabeled [³H]AMPA, [³H]kainic acid and [³H]CGP 39653, respectively. All compounds were tested at a single concentration of 100 uM in triplicate. mGluR1, mGluR2, mGluR5 and $GABA_B$ binding assays were performed by Eurofins Discovery. mGluR1 assay was performed using rat cerebellum membranes and radiolabeled [³H]quisqalic acid. mGluR2 assay was performed using recombinant Chem-1 cells and [³H] LY341495. mGluR5 and $GABA_B$ binding assays were performed using recombinant CHO-K1 cells and [³H]CGP-54626 and [³H]quisqalic acid, respectively. All compounds were tested at a single concentration of 100 uM in triplicate. Cancer Cells Proliferation Assay.

Cancer cell proliferation assays on MDA-MB-231, SK-OV-3 and MCF-7 cell lines were performed by BPS Bioscience Inc., San Diego, CA. Potential inhibitors were tested in triplicate in 1 nM-100 μM concentration range with cisplatin as control compound. The incubation time was set to 72 h and the cell proliferation was assayed with the CellTiter-Glo assay from Promega.
GLS1 Inhibition Assay.

GLS1 inhibition assays were performed using GLS1 Inhibitor Screening Assay Kit from BioVision Inc, Milpitas, CA. Potential inhibitors were tested in 0.5 μM-1 mM concentration range using initial reaction rate measurement.

TABLE 2

EC50 in mM determined in functional agonist receptor assays. Top test compound concentration was 100 μM (glutamate receptors) or 1 mM (GABA receptors). Assays were performed by SB Drug Discovery using FLIPR technology in stably receptor expressing cells.

| receptor | species | (R)-2MeGlu | (S)-2MeGlu |
|---|---|---|---|
| GluN2A | human | ND | ND |
| GluN2B | human | ND | ND |
| GluN2C | human | ND | ND |
| GluN2D | human | ND | ND |
| GluA2 | human | ND | ND |
| $GABA_A$ α1β1γ2 | human | ND | ND |
| $GABA_A$ α1β2γ2 | human | ND | ND |
| $GABA_A$ α1β3γ2 | human | ND | ND |
| $GABA_A$ α2β1γ2 | human | ND | ND |
| $GABA_A$ α2β2γ2 | human | 0.66 | 0.53 |
| $GABA_A$ α2β3γ2 | human | 0.622 | 0.342 |
| $GABA_A$ α3β1γ2 | human | 0.742 | 0.782 |
| $GABA_A$ α3β2γ2 | human | 1.043 | 0.961 |

TABLE 2-continued

EC50 in mM determined in functional agonist receptor assays. Top test compound concentration was 100 μM (glutamate receptors) or 1 mM (GABA receptors). Assays were performed by SB Drug Discovery using FLIPR technology in stably receptor expressing cells.

| receptor | species | (R)-2MeGlu | (S)-2MeGlu |
|---|---|---|---|
| GABA$_A$ α3β3γ2 | human | 0.959 | 0.725 |
| GABA$_A$ α4β1γ2 | human | 0.87 | 0.704 |
| GABA$_A$ α4β2γ2 | human | 1.246 | 1.025 |
| GABA$_A$ α4β3γ2 | human | >1.000 | >1.000 |
| GABA$_A$ α4β3δ | human | ND | ND |
| GABA$_A$ α5β1γ2 | human | ND | ND |
| GABA$_A$ α5β2γ2 | human | ND | ND |
| GABAA α5β3γ2 | human | ND | ND |
| GABAA α6β1γ2 | human | 0.772 | 0.28 |
| GABAA α6β2γ2 | human | ND | ND |
| GABAA α6β3γ2 | human | >1.000 | 0.998 |

TABLE 3

EC50 in mM determined in functional positive allosteric modulator receptor assays. Top test compound concentration was 100 μM (glutamate receptors) or 1 mM (GABA receptors). Assays were performed by SB Drug Discovery using FLIPR technology in stably receptor expressing cells.

| receptor | species | (R)-2MeGlu | (S)-2MeGlu |
|---|---|---|---|
| GluN2A | human | ND | ND |
| GluN2B | human | ND | ND |
| GluN2C | human | ND | ND |
| GluN2D | human | ND | ND |
| GluA2 | human | ND | ND |
| GABA$_A$ α1β1γ2 | human | ND | ND |
| GABA$_A$ α1β2γ2 | human | ND | ND |
| GABA$_A$ α1β3γ2 | human | ND | ND |
| GABA$_A$ α2β1γ2 | human | ND | ND |
| GABA$_A$ α2β2γ2 | human | ND | ND |
| GABA$_A$ α2β3γ2 | human | ND | ND |
| GABA$_A$ α3β1γ2 | human | ND | ND |
| GABA$_A$ α3β2γ2 | human | ND | ND |
| GABA$_A$ α3β3γ2 | human | ND | ND |
| GABA$_A$ α4β1γ2 | human | ND | ND |
| GABA$_A$ α4β2γ2 | human | ND | ND |
| GABA$_A$ α4β3γ2 | human | ND | ND |
| GABA$_A$ α4β3δ | human | ND | ND |
| GABA$_A$ α5β1γ2 | human | ND | ND |
| GABA$_A$ α5β2γ2 | human | ND | ND |
| GABA$_A$ α5β3γ2 | human | ND | ND |
| GABA$_A$ α6β1γ2 | human | ND | ND |
| GABAA α6β2γ2 | human | ND | ND |
| GABAA α6β3γ2 | human | ND | ND |

TABLE 4

IC50 in mM determined in functional antagonist receptor assays. Top test compound concentration was 100 μM (glutamate receptors) or 1 mM (GABA receptors). Assays were performed by SB Drug Discovery using FLIPR technology in stably receptor expressing cells.

| receptor | species | (R)-2MeGlu | (S)-2MeGlu |
|---|---|---|---|
| GluN2A | human | 0.069 | ND |
| GluN2B | human | ND | ND |
| GluN2C | human | ND | ND |
| GluN2D | human | ND | ND |
| GluA2 | human | ND | ND |
| GABA$_A$ α1β1γ2 | human | ND | ND |
| GABA$_A$ α1β2γ2 | human | ND | ND |
| GABA$_A$ α1β3γ2 | human | ND | ND |
| GABA$_A$ α2β1γ2 | human | ND | ND |
| GABA$_A$ α2β2γ2 | human | ND | ND |

TABLE 4-continued

IC50 in mM determined in functional antagonist receptor assays. Top test compound concentration was 100 μM (glutamate receptors) or 1 mM (GABA receptors). Assays were performed by SB Drug Discovery using FLIPR technology in stably receptor expressing cells.

| receptor | species | (R)-2MeGlu | (S)-2MeGlu |
|---|---|---|---|
| GABA$_A$ α2β3γ2 | human | ND | ND |
| GABA$_A$ α3β1γ2 | human | ND | ND |
| GABA$_A$ α3β2γ2 | human | ND | ND |
| GABA$_A$ α3β3γ2 | human | ND | 0.978 |
| GABA$_A$ α4β1γ2 | human | ND | ND |
| GABA$_A$ α4β2γ2 | human | ND | ND |
| GABA$_A$ α4β3γ2 | human | ND | ND |
| GABA$_A$ α4β3δ | human | ND | ND |
| GABA$_A$ α5β1γ2 | human | ND | ND |
| GABA$_A$ α5β2γ2 | human | ND | ND |
| GABA$_A$ α5β3γ2 | human | ND | ND |
| GABA$_A$ α6β1γ2 | human | ND | ND |
| GABAA α6β2γ2 | human | ND | ND |
| GABAA α6β3γ2 | human | ND | ND |

TABLE 5

Summary of binding inhibition assays. All compounds were tested at 100 μM in triplicate. Values indicate % of radioligand binding inhibition by test compounds. Assays were performed by Eurofins Discovery using radiolabeled ligands and human receptor expressing cells or rat brain membrane preparations.

| receptor | species | (R)-2MeGlu | (S)-2MeGlu |
|---|---|---|---|
| GABA$_B$ nonsel | rat | 5 | 5 |
| GABA$_B$ (B1a/B2) | human | 18 | 6 |
| GABA$_B$ (B1b/B2) | human | 13 | 14 |
| mGluR1 | rat | −3 | 6 |
| mGluR2 | human | −3 | 25 |
| mGluR5 | human | −20 | 11 |
| mGluR5 | human | −2 | −4 |
| NMDA nonspec | rat | 8 | 3 |
| AMPA nonspec | rat | 15 | 12 |
| kainate nonspec | rat | 18 | 20 |

TABLE 6

Summary of functional assays. All compounds were tested at 100 μM in triplicate. Values indicate % of agonist response. Assays were performed by Eurofins Discovery using Ca$^{2+}$-dependent fluorimetry and human receptor expressing cells.

| receptor | species | (R)-2MeGlu | (S)-2MeGlu |
|---|---|---|---|
| GABA$_B$ (B1/B2) | human | 0 | 0 |

REFERENCES

1. Bak, L. K., Schousboe, A. & Waagepetersen, H. S. The glutamate/GABA-glutamine cycle: aspects of transport, neurotransmitter homeostasis and ammonia transfer. J. Neurochem. 98, 641-653 (2006).
2. Bouché, N. & Fromm, H. GABA in plants: just a metabolite? Trends in Plant Science vol. 9 110-115 (2004).
3. Rumping, L. et al. Identification of a Loss-of-Function Mutation in the Context of Glutaminase Deficiency and Neonatal Epileptic Encephalopathy. JAMA Neurol. 76, 342-350 (2019).
4. Häberle, J. et al. Congenital glutamine deficiency with glutamine synthetase mutations. N. Engl. J. Med. 353, 1926-1933 (2005).

5. Pearl, P. L. et al. Clinical spectrum of succinic semi-aldehyde dehydrogenase deficiency. Neurology 60, 1413-1417 (2003).

6. Lapalme-Remis, S. et al. Natural history of succinic semialdehyde dehydrogenase deficiency through adulthood. Neurology 85, 861-865 (2015).

7. Jakobs, C. et al. Urinary excretion of gamma-hydroxybutyric acid in a patient with neurological abnormalities. The probability of a new inborn error of metabolism. Clinica Chimica Acta vol. 111 169-178 (1981).

8. Chambliss, K. L. et al. Two exon-skipping mutations as the molecular basis of succinic semialdehyde dehydrogenase deficiency (4-hydroxybutyric aciduria). Am. J. Hum. Genet. 63, 399-408 (1998).

9. Allen, P., Sommer, I. E., Jardri, R., Eysenck, M. W. & Hugdahl, K. Extrinsic and default mode networks in psychiatric conditions: Relationship to excitatory-inhibitory transmitter balance and early trauma. Neurosci. Biobehav. Rev. 99, 90-100 (2019).

10. Froestl, W. An historical perspective on GABAergic drugs. Future Med. Chem. 3, 163-175 (2011).

11. Spatazza, J., Mancia Leon, W. R. & Alvarez-Buylla, A. Transplantation of GABAergic interneurons for cell-based therapy. Prog. Brain Res. 231, 57-85 (2017).

12. Konya, Y., Bamba, T. & Fukusaki, E. Extra-facile chiral separation of amino acid enantiomers by LC-TOFMS analysis. J. Biosci. Bioeng. 121, 349-353 (2016).

13. Hollingsworth, E. B. et al. Biochemical characterization of a filtered synaptoneurosome preparation from guinea pig cerebral cortex: cyclic adenosine 3':5'-monophosphate-generating systems, receptors, and enzymes. The Journal of Neuroscience vol. 5 2240-2253 (1985).

14. Gajera, C. R. et al. Mass synaptometry: High-dimensional multi parametric assay for single synapses. J. Neurosci. Methods 312, 73-83 (2019).

15. Pamiljans, V., Krishnaswamy, P. R., Dumville, G. & Meister, A. Studies on the Mechanism of Glutamine Synthesis; Isolation and Properties of the Enzyme from Sheep Brain*. Biochemistry vol. 1 153-158 (1962).

16. Kagan, H. M., Manning, L. R. & Meister, A. Stereospecific synthesis of alpha-methyl-L-glutamine by glutamine synthetase. Biochemistry 4, 1063-1068 (1965).

17. Gaisler-Salomon, I. et al. Glutaminase-deficient mice display hippocampal hypoactivity, insensitivity to pro-psychotic drugs and potentiated latent inhibition: relevance to schizophrenia. Neuropsychopharmacology 34, 2305-2322 (2009).

18. Meister, A. [27] Glutamine synthetase from mammalian tissues. in Methods in Enzymology vol. 113 185-199 (Academic Press, 1985).

19. Kvamme, E., Torgner, I. A. A. & Svenneby, G. [30] Glutaminase from mammalian tissues. in Methods in Enzymology vol. 113 241-256 (Academic Press, 1985).

20. Cluntun, A. A., Lukey, M. J., Cerione, R. A. & Locasale, J. W. Glutamine Metabolism in Cancer: Understanding the Heterogeneity. Trends Cancer Res. 3, 169-180 (2017).

21. Gross, M. I. et al. Antitumor activity of the glutaminase inhibitor CB-839 in triple-negative breast cancer. Mol. Cancer Ther. 13, 890-901 (2014).

22. Yang, L. et al. Metabolic shifts toward glutamine regulate tumor growth, invasion and bioenergetics in ovarian cancer. Mol. Syst. Biol. 10, 728 (2014).

23. Page, L. B. & Sidd, J. J. Medical management of primary hypertension. 2. N. Engl. J. Med. 287, 1018-1023 (1972).

24. Black, D. G., Heagerty, A. M., Bing, R. F., Thurston, H. & Swales, J. D. Effects of treatment for hypertension on cerebral haemorrhage and infarction. BMJ vol. 289 1145-1145 (1984).

25. Djurisic, M., Brott, B. K., Saw, N. L., Shamloo, M. & Shatz, C. J. Activity-dependent modulation of hippocampal synaptic plasticity via PirB and endocannabinoids. Mol. Psychiatry 24, 1206-1219 (2019).

26. Rogers, D. C. et al. Behavioral and functional analysis of mouse phenotype: SHIRPA, a proposed protocol for comprehensive phenotype assessment. Mamm. Genome 8, 711-713 (1997).

27. Bader, P. L. et al. Mouse model of Timothy syndrome recapitulates triad of autistic traits. Proc. Natl. Acad. Sci. U.S.A 108, 15432-15437 (2011).

28. Portmann, T. et al. Behavioral Abnormalities and Circuit Defects in the Basal Ganglia of a Mouse Model of 16p11.2 Deletion Syndrome. Cell Reports vol. 7 1077-1092 (2014).

29. Faizi, M. et al. Comprehensive behavioral phenotyping of Ts65Dn mouse model of Down Syndrome: Activation of $\beta$1-adrenergic receptor by xamoterol as a potential cognitive enhancer. Neurobiology of Disease vol. 43 397-413 (2011).

30. Faizi, M. et al. Thy1-hAPPLond/Swe+ mouse model of Alzheimer's disease displays broad behavioral deficits in sensorimotor, cognitive and social function. Brain Behav. 2, 142-154 (2012).

31. Mah, G. T., Tejani, A. M. & Musini, V. M. Methyldopa for primary hypertension. Cochrane Database Syst. Rev. CD003893 (2009).

32. Mzengeza, S., Venkatachalam, T. K. & Diksic, M. Asymmetric radiosynthesis of alpha-[11C]methyl-L-tryptophan for PET studies. Nucl. Med. Biol. 22, 303-307 (1995).

33. Chugani, H. T. et al. α-[11C]-Methyl-L-tryptophan—PET in 191 patients with tuberous sclerosis complex. Neurology 81, 674-680 (2013).

34. Gal, A. E., Avakian, S. & Martin, G. J. A Synthesis of dl-a-Methylglutamic Acid and Some Derivatives. J. Am. Chem. Soc. 76, 4181-4182 (1954).

35. Takenishi, T. & Simamura, O. The Syntheses from Levulinic Acid. A Possible Use of Some 2-Methyl-5-oxopyrrolidine-2-carboxylic Esters as Plasticizers. BCSJ 27, 207-209 (1954).

36. Pfister, K. et al. a-Methyl-a-amino Acids. I. Homologs of Glutamic Acid, Methionine and Diaminopimelic Acid. J. Am. Chem. Soc. 77, 697-700 (1955).

37. Fonda, M. L. Glutamate decarboxylase. Substrate specificity and inhibition by carboxylic acids. Biochemistry 11, 1304-1309 (1972).

38. Fonda, M. L. & DeGrella, R. F. Inactivation of glutamate decarboxylase by bromopyruvate. Biochem. Biophys. Res. Commun. 56, 451-458 (1974).

39. Grant, P. L., Basford, J. M. & John, R. A. An investigation of transient intermediates in the reaction of 2-methylglutamate with glutamate decarboxylase from *Escherichia coli*. Biochem. J 241, 699-704 (1987).

40. Gould, S. J., Guo, J., Geitmann, A. & Dejesus, K. Nucleoside intermediates in blasticidin S biosynthesis identified by the in vivo use of enzyme inhibitors. Can. J. Chem. 72, 6-11 (1994).

41. Bolz, C. et al. Comparison of enzymatic properties and small molecule inhibition of y-glutamyltranspeptidases from pathogenic and commensal bacteria. Biol. Chem. 398, 341-357 (2017).

42. Haldeman, S., Huffman, R. D., Marshall, K. C. & McLennan, H. The antagonism of the glutamate-induced and synaptic excitations of thalamic neurones. Brain Res. 39, 419-425 (1972).

43. Piggott, S. M., Kerkut, G. A. & Walker, R. J. Structure-activity studies on glutamate receptor sites of three identifiable neurones in the sub-oesophageal ganglia of *Helix aspersa*. Comp. Biochem. Physiol. C 51, 91-100 (1975).

44. Shank, R. P. & Freeman, A. R. Agonistic and antagonistic activity of glutamate analogs on neuromuscular excitation in the walking limbs of lobsters. J. Neurobiol. 7, 23-36 (1976).

45. Dudel, J. Aspartate and other inhibitors of excitatory synaptic transmission in crayfish muscle. Pflugers Arch. 369, 7-16 (1977).

46. Bloomfield, S. A. & Dowling, J. E. Roles of aspartate and glutamate in synaptic transmission in rabbit retina. 1. Outer plexiform layer. J. Neurophysiol. 53, 699-713 (1985).

47. Kern, H. L. & Ho, C.-K. Transport of Dicarboxylic Amino Acids in the Rat Lens. Ophthalmic Res. 6, 166-174 (1974).

48. Balcar, V. J., Schousboe, A., Spoerri, P. E. & Wolff, J. R. Differences between substrate specificities of l-glutamate uptake by neurons and glia, studied in cell lines and primary cultures. Neurochem. Int. 10, 213-217 (1987).

49. Ganel, R. & Crosson, C. E. Modulation of human glutamate transporter activity by phorbol ester. J. Neurochem. 70, 993-1000 (1998).

50. Miralles, A. & Olmos, G. [3H]kainic acid binding sites in chick cerebellar membranes. Comp. Biochem. Physiol. C 93, 321-325 (1989).

51. Mori, M. & Shiio, I. Glutamate Transport and Production in *Brevibacterium flavum*. Agric. Biol. Chem. 47, 983-990 (1983).

52. Campbell, G. L., Bartel, R., Freidman, H. S. & Bigner, D. D. Effect of glutamate analogues on brain tumor cell lines. J. Neurochem. 45, 1186-1192 (1985).

53. Roberts, P. J. & Anderson, S. D. Stimulatory effect of L-glutamate and related amino acids on [3H]dopamine release from rat striatum: an in vitro model for glutamate actions. J. Neurochem. 32, 1539-1545 (1979).

54. Preuss, H. G. The effects of alpha-methylglutamate on ammonium excretion and renal ammonia production in rats. Toxicol. Appl. Pharmacol. 54, 454-461 (1980).

55. Ichida, S. et al. Effects of neurotransmitter candidates on 45Ca uptake by cortical slices of rat brain: stimulatory effect of L-glutamic acid. Brain Res. 248, 305-311 (1982).

56. Kemp, M. C., Jane, D. E., Tse, H. W. & Roberts, P. J. Agonists of cyclic AMP-coupled metabotropic glutamate receptors in adult rat cortical slices. Eur. J. Pharmacol. 309, 79-85 (1996).

57. Proceedings of the British Pharmacological Society. 10-12 Sep. 1980. Abstracts. Br. J. Pharmacol. 72, 487P-590P (1981).

58. Izumi, Y., Tatsumi, S., Imaida, M., Fukuda, Y. & Akabori, S. The preparation of optically active alpha-C-substituted glutamic acid. Bull. Chem. Soc. Jpn. 38, 1338-1340 (1965).

59. Obrecht, D. et al. A novel synthesis of (R)- and (S)-α-alkylated aspartic and glutamic acids: α-alkylated aspartic succinimides as new type of β-turn type II and II' mimetics. Tetrahedron 51, 10883-10900 (1995).

60. Islam, M. M. et al. Binding of C5-dicarboxylic substrate to aspartate aminotransferase: implications for the conformational change at the transaldimination step. Biochemistry 44, 8218-8229 (2005).

61. Colson, P. J. & Hegedus, L. S. Asymmetric synthesis of .alpha.-alkyl-.alpha. amino acids from chromium-carbene-complex-derived .beta.-lactams. J. Org. Chem. 58, 5918-5924 (1993).

62. Tang, G., Tian, H. & Ma, D. Asymmetric Strecker reaction of y-keto acids. Facile entry to a-substituted and α,γ-disubstituted glutamic acids. Tetrahedron 60, 10547-10552 (2004).

63. Tsubogo, T., Kano, Y., Ikemoto, K., Yamashita, Y. & Kobayashi, S. Synthesis of optically active, unnatural a-substituted glutamic acid derivatives by a chiral calcium-catalyzed 1,4-addition reaction. Tetrahedron Asymmetry 21, 1221-1225 (2010).

64. Bera, K., Satam, N. S. & Namboothiri, I. N. N. Enantioselective Synthesis of Quaternary α-Amino Acids via I-tert-Leucine-Derived Squaramide-Catalyzed Conjugate Addition of α-Nitrocarboxylates to Enones. J. Org. Chem. 81, 5670-5680 (2016).

65. Holden, J. T., Utech, N. M. & Garth Reid, K. α-Methyl-1-glutamic acid uptake by high affinity dicarboxylic amino acid transport system in *Streptococcus faecalis*. Biochimica et Biophysica Acta (BBA)—Biomembranes 394, 55-64 (1975).

66. Vandenberg, R. J., Mitrovic, A. D., Chebib, M., Balcar, V. J. & Johnston, G. A. Contrasting modes of action of methylglutamate derivatives on the excitatory amino acid transporters, EAAT1 and EAAT2. Mol. Pharmacol. 51, 809-815 (1997).

67. Yin, J. et al. Otud7a Knockout Mice Recapitulate Many Neurological Features of 15q13.3 Microdeletion Syndrome. Am. J. Hum. Genet. 102, 296-308 (2018).

68. Min, S.-W. et al. Critical role of acetylation in tau-mediated neurodegeneration and cognitive deficits. Nat. Med. 21, 1154-1162 (2015).

69. Evans, A. K. et al. Beta-adrenergic receptor antagonism is proinflammatory and exacerbates neuroinflammation in a mouse model of Alzheimer's Disease. Neurobiol. Dis. 146, 105089 (2020).

Example 2

Enantiomers of 4-Aminopentanoic Acid Act as
False GABAergic Neurotransmitters and Impact
Mouse Behavior Imbalance in the metabolic pathway linking excitatory and inhibitory neurotransmission has been implicated in multiple psychiatric and neurologic disorders. In example 1, we described enantiomer-specific effects of 2-methylglutamate, which is not decarboxylated to the corresponding methyl analogue of gamma-aminobutyric acid (GABA): 4-aminopentanoic acid (4APA). Here we tested the hypothesis that 4APA also has enantiomer-specific actions in brain. Mouse cerebral synaptosome uptake (nmol/mg protein over 30 min) of (R)-4APA or (S)-4APA was time- and temperature dependent; however, the R enantiomer had greater uptake, reduction of endogenous GABA concentration, and release following membrane depolarization than did the S enantiomer. (S)-4APA exhibited some weak agonist (GABA$_A$ α4β3δ, GABA$_A$ α5β2γ2, and GABA$_B$ B1/B2) and antagonist (GABA$_A$ α6β2γ2) activity while (R)-4APA showed weak agonist activity only with GABAA α5β2γ2. Both 4APA enantiomers (100 mg/kg IP) were detected in mouse brain 10 min after injection, and by one hour had reached concentrations that were stable over six hours; both enantiomers were cleared rapidly from mouse serum over six hours. Two-month old mice had no mortality following 100 to 900 mg/kg IP of each 4APA enantiomer but ded have similar dose-dependent reduction in distance moved in a novel cage. Neither enantiomer at 30 or 100 mg/kg impacted outcomes in twenty-three measures of well-being, activity chamber, or withdrawal from hotplate. Our results demonstrate that enantiomers of 4APA are active in the brain, and that (R)-4APA can act as a novel false neurotransmitter of GABA.

Here, we have investigated the enantiomer-specific neurochemical and pharmacological properties of 4APA in vitro in mouse cerebral synaptosomes and in vivo in young adult mice (FIG. 17).

Materials and Methods

All mouse procedures followed National Institutes of Health guidelines and were approved by Stanford's Institutional Administrative Panel on Laboratory Animal Care (APLAC; approval number 31890).

(rac)-4-Aminopentanoic acid (as hydrochloride, cat. no. EN300-81918), (R)-4-aminopentanoic acid (as hydrochloride, cat. no. BBV-38374677, optical rotation value +9.2°), and (S)-4-aminopentanoic acid (as hydrochloride, cat. no. BBV-38375018, optical rotation value −7.4°) were obtained from Enamine. Per the manufacturer's certificate of analysis, these optical rotation values were measured at 21° C., 589 nm, and 0.5 g/100 ml $H_2O$.

LC-MS-grade acetonitrile (cat. no. A955), formic acid (cat. no. A117) and trifluoroacetic acid (cat. no. A116) were obtained from Fisher Scientific. Isotopically labeled GABA (GABA-2,2,3,3,4,4-d6, cat. no. 615587) was purchased from Sigma. HPLC-grade ammonium formate (cat. no. 60-020-36) was obtained from Fluka.

Solutions were prepared exactly as previously described (Wawro et al., 2021): Buffer S (isotonic buffered sucrose solution) was 0.32 M sucrose, 1 mM EDTA, 5 mM Tris-HCl pH 7.4. Buffer KRP (normal Krebs-Ringer phosphate buffer) was 118.0 mM NaCl, 4.65 mM KCl, 1.23 mM $CaCl_2$, 1.18 mM $KH_2PO_4$, 3.54 mM $MgSO_4$, 15.64 mM $Na_2HPO_4$, 10 mM glucose. Buffer K-KRP (high-potassium Krebs-Ringer phosphate buffer) was 84.3 mM NaCl, 40.5 mM KCl, 1.23 mM $CaCl_2$, 1.18 mM $KH_2PO_4$, 3.54 mM $MgSO_4$, 15.64 mM $Na_2HPO_4$, 10 mM glucose.

Absolute Configuration of 4APA Enantiomers.

The optical rotation of (R)-4APA has been reported as both positive (Otsuka et al. 1990; Mayol et al. 2016) and negative (Stenlake et al. 1955; Okamoto et al. 1979). The absolute configuration of the purchased 4APA was assigned by the manufacturer based on the optical rotation noted above; however, to clarify any ambiguity we measured X-ray diffraction of a crystal obtained from bulk (+)-4APA, assigned the absolute configuration using the diffraction data, and further analyzed using chiral LCMS to confirm the major enantiomer of the bulk sample. We found that the X-ray diffraction measurement agreed with the assignment made by the manufacturer. (+)-4APA was recrystallized from methanol/isopropanol mixture. The diffraction data were collected using Bruker D8 Venture diffractometer equipped with a PHOTON II detector. The measurement was done at 100 K with Cu Kα radiation. The crystal obtained from bulk (+)-4APA was the R enantiomer and matched the bulk of the sample. The crystallographic data were deposited at the Cambridge Crystallographic Data Centre under the deposition number CCDC 2025613.

Chemical Characterization of Enantiomers (R)-4APA·HCl: 1H NMR (D20, 500 MHz): 3.43 (h, J=6.7 Hz, 1H), 2.55 (m, 2H), 2.01 (m, 1H), 1.87 (m, 1H), 1.32 (d, J=6.6 Hz, 3H). $^{13}C[^1H]$NMR ($D_2O$, 126 MHz): δ 177.1, 47.1, 29.8, 28.9, 17.3. 97% e.e. (chiral LC-MS)

(S)-4APA·HCl: $^1H$ NMR ($D_2O$, 500 MHz): 3.43 (h, J=6.7 Hz, 1H), 2.54 (m, 2H), 2.01 (m, 1H), 1.87 (m, 1H), 1.32 (d, J=6.6 Hz, 3H). $^{13}C[^1H]$ NMR ($D_2O$, 126 MHz): δ 177.1, 47.1, 29.8, 28.9, 17.2, 95% e.e. (chiral LC-MS).

Synaptosomes.

Mouse cerebral synaptosomes were prepared exactly according to published methods (Gajera et al. 2019; Wawro et al. 2021). Briefly, for each biological replicate, the cerebral hemispheres from one C57BL/6 mouse were combined and homogenized in 3 mL of Buffer S using pre-chilled 5 mL Potter-ELV tissue grinder (800 rpm, 8 strokes). The crude homogenate was diluted with Buffer S to 4 mL and sedimented at 1,000 g for 10 min at 4° C. The supernatant was sedimented (10,000 g for 20 min at 4° C.) and the pellet washed by resuspension-centrifugation (8,000 g for 4 min at 4° C.) with Buffer S (4 mL, ×1) and Buffer KRP (2 mL, ×3). The resulting pellet was resuspended in 3 mL of Buffer KRP and filtered on Ultrafree-CL 5 μm PVDF centrifugal device (1,000 g for 4 min at 4° C.). The filtrate was diluted to 15 mL with ice cold Buffer KRP and kept on ice. The synaptosome preparation was used immediately. Total protein concentration was determined with Pierce BCA Protein Assay Kit.

Synaptosome uptake and high potassium-induced release assays were performed as described in Example 1. Uptake assays used 250 μL aliquots of the synaptosome suspension transferred to a pre-chilled 0.8 mL 96 well plate. 5 μL of a test compound solution (0.5 mM; final concentration: 10 μM to compare directly to our previous work was added to each well and incubated at 0° C. or 37° C. After 10, 20 or 30 min, samples were chilled on ice and immediately sedimented (2,500 g for 15 min at 4° C.) and washed with Buffer S (0.5 mL, ×2). Resulting pellets were resuspended in 200 μL of 60% ACN containing 5 μM GABA-d6 and stored at −80° C. until analysis. Potassium-induced release assay used 500 μL aliquots of the synaptosome suspension transferred to pre-chilled microcentrifuge tubes. 2.5 μL of a test compound solution (20 mM; final concentration: 100 μM) in Buffer KRP was added to each tube and incubated for 15 min at 37° C., briefly chilled on ice, and then immediately sedimented (8,000 g for 4 min at 4° C.) and washed with Buffer KRP, followed by centrifugation, twice. The resulting pellets were resuspended in 500 μL of Buffer KRP or Buffer K-KRP and incubated for 5, 10 or 15 min at 37° C., sedimented (8,000 g for 4 min at 4° C.), and washed with Buffer KRP. Resulting pellets were resuspended in 400 μL of 60% ACN containing 2.5 μM GABA-d6 as internal standard and stored at −80° C. until analysis.

Pharmacokinetics.

Thirty-nine 2 to 3 month-old C57BL/6 male mice (Jackson Laboratory cat. no. 000664) were administered a single IP injection (100 mg/kg) of R-4APA (n=18), S-4APA (n=18), or vehicle (n=3). At each timepoint (10 min, 30 min, 1 h, 2 h, 4 h, 6 h for test compounds; 10 min for vehicle), mice were deeply anesthetized by isoflurane, blood was collected by cardiac puncture and left to clot on ice, and then perfused with cold PBS. Whole brain was promptly dissected and one half frozen at −80° C. until homogenization in ice cold PBS (pH 7.4) using a probe ultrasonic homog-enizer (Branson Sonifier 450, Power: 5, Cycle: 30%, time: 10 s) on ice. The lysate was sedimented (2,500 g for 15 min at 4° C.) and the supernatant assayed using Pierce BCA Protein Assay Kit (23225). Two or three 10 μL aliquots of the homogenate were transferred to a 96 well plate and extracted with 190 μL of 60% acetonitrile in water contain-ing 10 μM GABA-d6 as internal standard for stable isotope dilution assay of endogenous GABA and 4APA enantiomers. L-Glu-d5 was used as internal standard for assay glutamate exactly as previously described by us. Forty μL aliquots of the extracts were then diluted with 120 μL of acetonitrile and prepared for LC-MS/MS analysis. Brain and serum half-lives were calculated using the 'PKNCA' package for R.
LC-MS/MS.

LC-MS/MS HILIC analysis was performed using Agilent 6470 Triple Quadrupole LC/MS System with Agilent 1290 Infinity II LC module. All samples were filtered through a Multiscreen Solvinert 0.45 μm PTFE filter plate to a poly-propylene 0.5 mL 96-well plate. 2.5 μL was injected onto an Acquity UPLC BEH Amide column (2.1×50 mm, 1.7 μm particle size, Waters, part no. 186004800) equipped with an Acquity UPLC In-Line Filter (Waters, part no. 205000343) at 40° C. A gradient elution protocol (flow rate of 0.6 mL min$^{-1}$) was developed to isolate the 4APA peak from two isomeric compounds in brain tissue homogenate. It used buffer A (5 mM ammonium formate, 5 mM formic acid in water, pH 3.6) and buffer B (5 mM ammonium formate, 5 mM formic acid in 95:5 (v/v) acetonitrile-water), and the following gradient 0.0-2.5 min: linear gradient from 5% to 30% A; 2.51-3.0 min: hold 40% A; 3.01-3.5 min: hold at 5% A. The mass spectrometer was operated in multiple reaction monitoring (MRM) positive mode with capillary voltage set to 3.5 kV, nebulizing gas held at 250° C. and superheated sheat gas held at 300° C. Results were corrected for isoto-pically labeled internal standard.
LC-MS/MS Analysis, Chiral Conditions.

LC-MS/MS chiral analysis was performed using Agilent 6470 Triple Quadrupole LC/MS System with Agilent 1290 Infinity II LC module. Prior to analysis all samples were filtered through a Multiscreen Solvinert 0.45 μm PTFE filter plate to a polypropylene 0.5 mL 96-well plate. 1.0 μL of sample was injected onto a CROWNPAK CR-I(+) column (3.0×150 mm, 5 μm particle size, Daicel, part no. 53784) equipped with an Acquity UPLC In-Line Filter (Waters, part no. 205000343), thermostatted at 20° C. The sample was eluted isocratically at a flow rate of 0.4 mL min$^{-1}$ with buffer C (96:4 ACN/water v/v, 0.1% TFA; parameters varied in the optimization experiments). The mass spectrometer was operated in multiple reaction monitoring (MRM) positive mode with capillary voltage set to 3.5 kV, nebulizing gas held at 250° C. and superheated sheat gas held at 300° C.
Receptor Functional & Binding Assays.

All receptor assays were performed exactly as described in Example 1. Functional assays of all GABA$_A$, NMDA (GluN2A-GluN2D) and AMPA (GluA2) receptor subunits were performed by SB Drug Discovery as a part of their CNS discovery panel using FLIPR technology. All com-pounds were tested at 7 concentrations in triplicate and EC50/IC50 was determined where applicable. Functional GABA$_B$ assay was performed by Eurofins Discovery (Cerep) using Ca$^{2+}$-dependent fluorimetry in RBL cells expressing human GABA$_B$ (B1/B2) receptor. All com-pounds were tested at a single concentration of 100 uM in triplicate. Nonspecific AMPA, kainate and NMDA binding assays were performed by Eurofins Discovery (Cerep) using rat cerebral cortex membranes and radiolabeled [$^3$H]AMPA,

[$^3$H]kainic acid and [$^3$H]CGP 39653, respectively. All com-pounds were tested at a single concentration of 100 uM in triplicate. mGluR1, mGluR2, mGluR5 and GABA$_B$ binding assays were performed by Eurofins Discovery. All com-pounds were tested at a single concentration of 100 uM in triplicate.
Mouse Behavior.

Exploratory behavioral tests were performed exactly as previously described by us using 2-month-old C57Bl/6 male mice, Example 1. First, we assessed safety and tolerability of acute exposure to 4APA enantiomers in 22 mice by novel cage observation at 100, 300, or 900 mg/kg IP compared to vehicle (PBS) IP (n=3 or 4 mice per group without sample calculation, based on our previous study. Next, we evaluated 24 drug naïve mice with a 23-measure battery of neurologic dysfunction in mice (SHIRPA) (Rogers et al., 2001), auto-mated activity chamber assessment, and hot plate latency acutely following 30 or 100 mg/kg IP compared to vehicle IP (n=4 or 5 mice per group). No exclusion criteria were predetermined and no randomization was performed to allocate subjects in the study.
Statistics.

Statistical analysis and graphing were performed with GraphPad Prism (San Diego, CA). Data were analyzed with two-way analysis of variance (ANOVA) with α=0.05. D'Agostino and Pearson normality test showed normally distributed data (P>0.05). As noted below in the figure legends, ordinary two way ANOVA used Sidak's multiple comparisons test, and repeated measures two way ANOVA used Tukey's multiple comparisons test. Outliers (greater than 3 SD from mean) were not identified and no data points were excluded.
Results Both enantiomers of 4APA initially were evaluated for neurotransmitter-like properties in mouse cerebral synapto-somes exactly according to methods of example 1. Uptake experiments revealed that both enantiomers of 4APA were transported into mouse cerebral synaptosomes, but at dif-ferent rates. By 30 min at 37° C., (R)-4APA synaptosome concentration averaged 9.3±0.6 nmol/mg protein (n=3) while (S)-4APA synaptosome concentration was only 22.8±0.8% of (R)-4APA (P<0.0001) and the concentration of rac-4APA was 78.5±3.8% of (R)-4APA (P<0.0001) (FIG. 18). Following preincubation with compound or vehicle, synaptosomes were incubated in buffer with 5 mM or 40 mM K$^+$ for 15 min to induce membrane depolarization. Under these conditions, synaptosomes preincubated with vehicle had 9.5±0.2 nmol GABA/mg protein (n=3) and released 53.6+2.7% of their GABA with 40 mM K+(P<0.0001) (FIG. 18). Synaptosomes had significantly reduced total GABA concentration varying from 3.8±0.5, 6.0±0.6, or 4.4±0.4 nmol/mg protein (n=3 per group, P<0.0001), following preincubation with (R)-4APA, (S)-4APA, or rac-4APA, respectively, and the synaptosomal GABA retained following preincubation with 4APA enan-tiomers was significantly released by K+-induced membrane depolarization for all three compounds (n=3 per group, P<0.05) (FIG. 19). Synaptosome Glu concentration was not significantly changed by preincubation with rac-4APA. Syn-aptosome concentration of (R)-4APA or rac-4APA also was significantly reduced by K+-induced membrane depolariza-tion: 55.3±6.8% for (R)-4APA (n=3, P<0.01) and 62.2±8.6% for rac-4APA (n=3, P<0.001). K+-induced membrane depo-larization did not significantly reduce synaptosome concen-tration of (S)-4APA (FIG. 19B). Together, these data suggest that while (R)-4APA and (S)-4APA had a similar overall effect on synaptosomes the R enantiomer had faster uptake, displaced more GABA, and had greater release following membrane depolarization.

We have shown that 2MeGlu and 4APA are metabolically disconnected in brain because 2MeGlu, in contrast to L-Glu, is not decarboxylated in mouse synaptosomes or in vivo. Furthermore, oxidative deamination of 4APA into 4-oxo-pentanoic acid, the methyl analogue of succinic semialde-hyde, does not occur in mouse cerebral synaptosomes incubated with rac-4APA. We therefore determined the pharmacokinetics of (R)-4APA and (S)-4APA in serum and brain following a single 100 mg/kg intraperitoneal (IP) injection of compound (FIG. 20). Vehicle injected mice had background levels of 4APA of 3.5±1.1 pmol/L in serum and 4.4±0.9 pmol/mg protein in brain. Both enantiomers of 4APA were cleared rapidly from serum with two-phases of exponential decline, an initial rapid phase over 10 to 30 minutes followed by a slower decline in concentration over the remaining 5.5 hr. Both enantiomers of 4APA also were detectable in brain by 10 min following IP injection, and by 1 hour had reached concentrations that were stable out to 6 hr. Together, these data show rapid clearance of both 4APA enantiomers from blood and their retention as well as apparent metabolic stability in brain for up to 6 hr.

We next explored the pharmacodynamics of 4APA enan-tiomers against a broad panel of glutamate and GABA receptors in both binding and functional assays (summarized in Table 7). We deliberately assayed 4APA enantiomers for activity against both glutamate and GABA receptors in case of receptor class switching caused by insertion of methyl group, as occurs with α-methyldopamine. (S)-4APA exhib-ited some selective but weak agonist (GABA$_A$ α4β3δ, GABA$_A$ α5β2γ2, and GABA$_B$ B1/B2) and antagonist (GABA$_A$ α6R2γ2) activity with a few GABA$_A$ and GABA$_B$ $_{17}$ $_{18}$ receptor isoforms. (R)-4APA showed weak agonist activity only with GABA$_A$ α5β2γ2. Neither enan-tiomer of 4APA showed activity with glutamate receptors.

Investigators at the Stanford Behavioral and Functional Neuroscience Laboratory (SBFNL), who were blinded to the identity of the compounds being tested, performed a broad-based screen of safety and tolerability followed by tests of learning and memory, exactly the same as the behavioral screen of 2MeGlu. All behavioral assessments were per-formed with 2 month-old, healthy, drug naïve C57Bl/6 male mice. Initial behavioral assessments followed single IP injection of compound or vehicle. To assess tolerability, mice were injected with a single dose (100, 300, or 900 mg/kg IP; n=3 per group) of (R)-4APA or (S)-4APA and then immediately assessed by novel cage observation (FIG. 21) as well as for survival over the next 10 days; no mouse died during the 10 days of observation. Distance moved in the novel cage was significantly decreased immediately follow-ing injection of either (R)-4APA or (S)-4APA in a dose- and time-dependent manner, indicating marked reduction in response to novelty/locomotor activity while remaining alert and responsive, similar to what we observed with (R)-2MeGlu and (S)-2MeGlu (FIG. 21A). The dose effect of R and S enantiomers was not significantly different; however, the duration of reduced movement in the novel cage test was longer for the R enantiomer. Only 300 and 900 mg/kg (R)-4APA-dosed mice were significantly different from vehicle at 10 minutes post injection (P<0.05 for both) (FIG. 21B) and were not significantly different from vehicle until 13 and 42 minutes post injection, respectively.

Next, we performed a behavioral test battery called SHIRPA (a 23 measure behavioral screen of neurologic dysfunction in mice), activity chamber open field assess-ment, and then withdrawal from hot plate exactly as previ-ously described using new groups of 2 month-old, drug naïve, wild type C57Bl/6 male mice following a single injection of 100 or 30 mg/kg IP of one of the two enan-tiomers or vehicle (n=4-5 per group). Again, there was no mortality in any of the treatment groups. Furthermore, at these doses there was no significant difference between mice exposed to either dose of either enantiomer and vehicle for any of the 23 SHIRPA measures, any of the activity chamber measures, or latency to withdrawal from hotplate.

Although enantiomers of 4APA have been synthesized previously, conflicting absolute configuration has been reported (see Methods); for this reason, we directly deter-mined the absolute configuration of 4APA enantiomers used here. We are aware of no data on enantiomer-specific biological activity of 4APA. (R)-4APA and (S)-4APA entered the mouse brain following IP injection and achieved similar relatively constant brain concentrations from 2 to 6 hr post injection despite exponential decline in serum con-centration over this same period. These results indicated that each enantiomer of 4APA was similarly retained by brain over this period of time, and are in contrast to results stated but not shown by others for 400 mg/kg IP of racemic 4APA (see Callery et al. 1982). This discrepancy likely is related to our more sensitive and specific method of detection of pmol/mg protein concentrations of 4APA enantiomers in mouse brain. Both enantiomers were taken up in a time- and temperature-dependent manner into mouse cerebral synaptic particles, consistent with in vivo data showing retention in brain. However, in mouse synaptosomes uptake of (R)-APA was 4- to 5-fold faster than for (S)-4APA while uptake of racemic 4APA was in between the two enantiomers.

Once incorporated into synaptosomes, (S)-4APA dis-placed approximately 30% of endogenous GABA while (R)-4APA and racemic 4APA each displaced about 55% of endogenous GABA. The intrasynaptosomal concentrations of R and racemic 4APA were about double that of the S enantiomer, and approximately 50% to 60% of all four compounds (endogenous GABA, (R)-APA, (S)-4APA, and rac-4APA) were released by high concentration of potas-sium ion. Together, these data support a model where each enantiomer of 4APA crosses the blood-brain barrier, is taken up into GABAergic terminals, and is incorporated into synaptic vesicles partially displacing endogenous GABA; but (R)-APA is taken up faster and achieves greater synap-tosomal concentration than (S)-4APA.

The rationale for including both GABAergic and gluta-matergic receptors in our study was the observation that α-methyldopamine switches receptor class and interacts with noradrenergic receptors. We are unaware of molecular modeling data that investigated the potential impact on receptor binding of methyl substitution of GABA to form 4APA. (S)-4APA had limited activity and (R)-4APA had weak activity at only one of a broad panel GABA and glutamate receptors. Taken together, these data support (R)-4APA as a GABAergic false neurotransmitter, meaning that it is stored and released like a neurotransmitter but has minimal activity at receptors. We are unaware of any other GABAergic false neurotransmitter. Given that enantiomers of 4APA selectively replaced GABA in mouse synapto-somes, we hypothesize that they are substrates for GABA transporters, e.g. GAT-1 and GAT-3; however, their speci-ficity and affinity for GABA vs. other transporters will be the focus of future experiments.

Our survey of mouse behavior showed that both enan-tiomers of 4APA are safe up to 900 mg/kg IP and had a clear dose-dependent pharmacologic effect on locomotion/exploration of novelty in young healthy mice. At the same dose, the enantiomers had similar overall impact on locomotion/exploration with similar timing of onset; however, the effect of the R enantiomer lasted longer than S. While this action of 4APA enantiomers can be useful in some clinical settings, like induction for a procedure or imaging session, they also have value as diagnostics or therapeutics because of their prolonged half life in brain and unique properties as false neurotransmitters, as occurred with α-methyldopa and α-methyltryptophan. Enantiomers of 4APA have use as molecular imaging agents for GABAergic neurons, treatment of diseases that derive in part from imbalance of excitatory vs. inhibitory neurotransmission, including mood disorders, psychosis, Alzheimer's disease, and Parkinson's disease.

TABLE 7

Summary of glutamate and GABA receptor interaction assays.
'↑' or '↓' arrow indicates agonist
or antagonist activity, respectively. Interactions with
EC50 or IC50 below 100 µM are marked with an arrow.
Interactions weaker than that or not determined are marked as "—".

| receptor name | receptor type | assay type | (R)-4APA | (S)-4APA |
| --- | --- | --- | --- | --- |
| GluN2A | ionotropic | functional | — | — |
| GluN2B | ionotropic | functional | — | — |
| GluN2C | ionotropic | functional | — | — |
| GluN2D | ionotropic | functional | — | — |
| GluA2 | ionotropic | functional | — | — |
| mGluR1 | metabotropic | binding | — | — |
| mGluR2 | metabotropic | binding | — | — |
| mGluR5 | metabotropic | binding | — | — |
| NMDA nonspecific | ionotropic | binding | — | — |
| AMPA nonspecific | ionotropic | binding | — | — |
| kainite nonspecific | ionotropic | binding | — | — |
| GABAA α1β1γ2 | ionotropic | functional | — | — |
| GABAA α1β2γ2 | ionotropic | functional | — | — |
| GABAA α1β3γ2 | ionotropic | functional | — | — |
| GABAA α2β1γ2 | ionotropic | functional | — | — |
| GABAA α2β2γ2 | ionotropic | functional | — | — |
| GABAA α2β3γ2 | ionotropic | functional | — | — |
| GABAA α3β1γ2 | ionotropic | functional | — | — |
| GABAA α3β2γ2 | ionotropic | functional | — | — |
| GABAA α3β3γ2 | ionotropic | functional | — | — |
| GABAA α4β1γ2 | ionotropic | functional | — | — |
| GABAA α4β2γ2 | ionotropic | functional | — | — |
| GABAA α4β3γ2 | ionotropic | functional | — | — |
| GABAA α4β3δ | ionotropic | functional | — | ↑ |
| GABAA α5β1γ2 | ionotropic | functional | — | — |
| GABAA α5β2γ2 | ionotropic | functional | ↑ | ↑ |
| GABAA α5β3γ2 | ionotropic | functional | — | — |
| GABAA α6β1γ2 | ionotropic | functional | — | — |
| GABAA α6β2γ2 | ionotropic | functional | — | ↓ |
| GABAA α6β3γ2 | ionotropic | functional | — | — |
| GABAB (B1/B2) | metabotropic | binding | — | — |
| GABAB (B1a/B2) | metabotropic | binding | — | — |
| GABAB (B1b/B2) | metabotropic | binding | — | — |
| GABAB (B1/B2) | metabotropic | functional | — | ↑ |

Example 3

S-2MeGlu Dose-Dependently Rescues Motor Function In Vivo

At both the individual neuron and network levels, balanced excitatory (E, mostly glutamatergic) and inhibitory (I, mostly GABAergic) neurotransmission is critical to brain function and neuron health. Experimental and observational data support E-I imbalance as a mechanism of neurodegeneration in Alzheimer's disease (AD) and Parkinson's disease (PD) with most showing increased E neurotransmission in aged human brain and cerebrum of transgenic mouse models of AD. Indeed, one of the few FDA-approved treatments for AD is memantine, an uncompetitive antagonist for a specific subclass of ionotropic glutamate receptors. Moreover, several groups are developing novel pharmacologic tools to restore E-I balance in PD, focused mostly on allosteric modulators of a subclass of metabotropic glutamate receptors. These agents have activity in rodent models of PD with some evidence of neuroprotection, perhaps by suppressing dysregulated excitatory input, and in the non-human primate 1-methyl-4-phenyl-1,2,3,6-tetrahydropyridine (MPTP) model as an adjunct to dopamine replacement therapy.

Despite these impressive gains, receptor-specific agents have inherent disadvantages: there are dozens of glutamate receptors making it difficult to identify the most effective receptor subclass to target; receptor expression is highly adaptable to specific targeting leading to reduced effectiveness over time; memantine is the only approved drug in its class; and this approach neglects the potential contributions of GABAergic neurotransmission. We have invented a group of small molecules that are the first glutamatergic or GABAergic false neurotransmitters. False neurotransmitters are handled like endogenous or "true" neurotransmitters, including displacement of endogenous neurotransmitter in synaptic vesicles, but upon release false neurotransmitters fail to activate receptors. Our novel compounds provide a unique mode of action to rebalance E-I neurotransmission in AD and PD, and other brain diseases, by altering neurotransmitter metabolism rather than targeting specific receptors.

We created the first glutamatergic false neurotransmitter (S-2-methylglutamate or S-2MeGlu) and the first GABAergic false neurotransmitters (R-4 aminopentanomic acid (4APA) and S-4APA; these two enantiomers have different activity profiles). Others have substituted a methyl group at the 2 position on amino acid precursors of neurotransmitters with great clinical success, e.g., on L-dihydroxyphenylalanine to create Aldomet that was once a mainstay for control of hypertension and is still used today in gestational hypertension, and on L-tryptophan to produce a false neurotransmitter that has been used as a neuroimaging agent for the serotonergic system in human brain.

The data summarized below shows that S-2MeGlu dose-dependently rescues motor function in two different mouse models of PD and cognitive improvement in a mouse model of AD, and that R-4APA rescues motor function in a transgenic mouse model of PD.

MPTP Model of PD:

Five groups of mice were treated with 40 mg/kg/d MPTP IP on days 1 and 2 and two concentrations of two test agents IP from days −5 to day 14 (FIG. 22). One group received vehicle, two groups received 5 or 50 mg/kg/d S-2MeGlu, and two groups received 5 or 50 mg/kg/d R-4APA. MPTP mice had significantly reduced body weight on days 3 and 4 (P<0.01) compared to mice that received no MPTP. The high-precision fine motor kinematic protocol quantifies over 100 indices of gait and balance and integrates them into an overall kinematic score; higher score indicates greater impairment. Following unblinding, S-2MeGlu at 50 mg/kg/d, but not R-4APA, significantly rescued the motor deficit from MPTP. Mice were sacrificed on day 15 and striatal dopamine as well as its major metabolites were quantified by HPLC with electrochemical detection. Compared to the Vehicle/Vehicle group, all MPTP groups had an approximately 70% reduction in striatal dopamine (P<0.0001 for each) but no significant difference between MPTP/Vehicle and any of the MPTP/test agent groups. These data show S-2MeGlu dose-dependent rescue of MPTP-induced motor deficits without alteration of dopaminergic injury.

Transgenic α-Synuclein Mouse Model:

Line 61 mice overexpress human α-synuclein under control of the mouse Thy-1 promoter. The transgene is X-linked so females have variable transgene expression; for this reason, we focused on male mice. Motor function in Line 61 mice was measured using a tapered beam with video recording and scored as either (i) completely traversed the beam in <120 seconds or (ii) fell off the beam or did not complete the task in 120 seconds. Wild type (WT) mice had significantly better motor performance (approximately 85% completely traversed the beam in <120 seconds) than Line 61 mice (not shown). S-2MeGlu or R-4APA were administered as described above for seven days prior to testing (FIG. 23); there was no change in body weight or deaths. Categorical data from the tapered beam task were unblinded and analyzed by X square test (P<0.005). Line 61 mice treated with high dose S-2MeGlu or either dose of R-4APA had improved motor function similar to WT mice. There was no significant change by immunohistochemistry in α-synuclein accumulation in brains of Line 61 mice treated with S-2Me-Glu or R-4APA compared to vehicle. These results show a similar S-2MeGlu dose-dependent rescue in motor function in Line 61 mice as was observed in the MPTP model. Unlike the MPTP model, similar improvement in motor function was observed with both doses of R-4APA in Line 61 mice.

Transgenic Aβ Model of AD:

Cerebral Aβ accumulation is a core feature of AD. Since memantine, a glutamate receptor subtype antagonist is an approved treatment for people with AD, we tested whether our false glutamatergic neurotransmitter might be therapeutic in a transgenic model of AD. Four month old Line 41 male mice were treated with S-2MeGlu at 10 mg/kg/d IP for 6 weeks with behavior tested using activity chamber, Y maze, novel object and novel place recognition, Morris water maze, and fear conditioning. There was no difference in body weights or any deaths during the 6-week experiments. After unblinding, S-2MeGlu only rescued performance in the Y maze (P<0.05, FIG. 24). There was no change in Aβ accumulation by immunohistochemistry in Line 41 mice treated with S-2MeGlu. These data suggest that S-2MeGlu will dose-dependently improve working memory in people with AD.

Neurodegeneration:

We employed a standard technique of ex vivo experimentation to determine the efficacy of 2MeGlu, 2MeGln, and 4APA to prevent neurodegeneration. Mouse hippocampal slice cultures were prepared and then exposed to one of the three test compounds at either 5 or 50 μM for one hour. Then media was changed to contain either 2 or 5 μM kanic acid (KA) for 24 hr. KA causes dose dependent neurodegeneration in hippocampal neurons by activating its receptor and triggering excessive excitatory neurotransmission that is completely blocked by the ionotropic glutamate receptor subtype NMDA antagonist, memantine. After 24, the amount of neurodegeneration was assayed with propidium iodide staining. Increasing the dose of KA led to greater neurodegeneration at 5 μM than at 2 μM.

At the lower dose of KA, the higher dose of 2MeGlu or 2MeGln (50 μM) substantially reduced neurodegeneration by approximately one-half (FIG. 25). Neither dose of 2MeGlu or 2MeGln was neuroprotective at the higher dose of KA. 4APA was not neuroprotective in this model at either 5 or 50 μM. These data are important because they demonstrate dose-dependent prevention of neurodegeneration from excessive excitatory neurotransmission by the false glutamatergic neurotransmitter, 2MeGlu, and the metabolically linked 2MeGln, but not by the false GABAergic neurotransmitter, 4APA. In addition, the data are important because they provide an initial estimate of the effective concentration needed to block neurodegeneration. Pharmacokinetic work in animal models determines the dose required to obtain effective concentrations in brain, and be followed by clinical trials to establish safety and determine effectiveness in people with Parkinson's disease, Alzheimer's disease, and other neurologic diseases thought to derive from imbalance of excitatory and inhibitory neurotransmission.

Example 4

Imaging

Four adult mice (M1 to M4) were injected with radiolabeled 2MeGlu either with 2.5 mg of non-radioactive 2MeGlu (M1) or without cold spike (M2 to M4), and then imaged by PET. $^{11}C$-2MeGlu showed a rapid rise in brain radioactivity (3% ID/g) that mostly cleared within the first 10 minutes, and is likely related to labeled compound in blood. Longer time points showed about 0.5% of the injected dose was retained throughout the brain for up to 40 minutes following injection, with greater apparent brain retention in the non-spiked injections. These results reflect rapid radiotracer delivery into brain and then slower clearance over time.

The preceding examples merely illustrate the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of altering balance of excitatory to inhibitory neurotransmission by a method comprising:

administering an effective dose of an agent that provides enantiomeric selective metabolism modulation in the GABA shunt or glutamate-glutamine cycle.

2. The method of claim 1, wherein the agent is an enantiomer of 2-methyl-glutamine (2-MeGln).

3. The method of claim 1, wherein the agent is an enantiomer of 2-methyl-glutamate (2-MeGlu).

4. The method of claim 1, wherein the agent is racemic 2-methyl-glutamine.

5. The method of claim 1, wherein the agent is enantiomerically pure (S)-2-MeGlu.

6. The method of claim 1, wherein the agent is an enantiomer of 4-aminopentanoic acid (4-APA).

7. The method of claim 6, wherein the agent is enantiomerically pure (R)-4-APA.

8. The method of claim 1, wherein the agent is a false neurotransmitter that reduces glutaminergic neural activity.

9. The method of claim 1, wherein the agent is a false neurotransmitter that reduces GABAergic neural activity.

10. The method of claim 1, wherein administration is provided in vivo to an individual in need thereof.

11. The method of claim 10, wherein the individual suffers from Parkinsons disease.

12. The method of claim 11, wherein the compound is (S)-2-MeGlu or (R)-4-APA.

13. The method of claim 10, wherein the individual suffers from Alzheimer's disease.

14. The method of claim 13, wherein the compound is (S)-2-MeGlu.

15. A pharmaceutically acceptable formulation for use in the method of claim 1, comprising an effective dose of the agent that provides enantiomeric selective metabolism modulation in the GABA shunt or glutamate-glutamine cycle, and a pharmaceutically acceptable excipient.

\* \* \* \* \*